United States Patent
Smith et al.

(10) Patent No.: US 11,542,267 B2
(45) Date of Patent: Jan. 3, 2023

(54) CRYPTATE COMPOUNDS

(71) Applicants: Australian Nuclear Science and Technology Organisation, Lucas Heights (AU); The Australian National University, Australian Capital Territory (AU)

(72) Inventors: Suzanne Virginia Smith, Kirrawee DC (AU); Eskender Mume, Rockdale (AU); Gary James Perkins, Beverly Hills (AU)

(73) Assignees: Australian Nuclear Science and Technology Organisation, Lucas Heights (AU); The Australian National University, Australian Capital Territory (AU)

( * ) Notice: Subject to any disclaimer, the term of this patent is extended or adjusted under 35 U.S.C. 154(b) by 0 days.

(21) Appl. No.: 16/900,335

(22) Filed: Jun. 12, 2020

(65) Prior Publication Data
US 2020/0308182 A1    Oct. 1, 2020

Related U.S. Application Data

(63) Continuation of application No. 14/129,855, filed as application No. PCT/AU2012/000817 on Jul. 6, 2012, now Pat. No. 10,717,741.

(30) Foreign Application Priority Data

Jul. 7, 2011    (AU) ................ 2011902708

(51) Int. Cl.
| | | |
|---|---|---|
| C07D 487/08 | (2006.01) | |
| A61K 49/00 | (2006.01) | |
| A61K 51/04 | (2006.01) | |

(52) U.S. Cl.
CPC ........ *C07D 487/08* (2013.01); *A61K 49/0021* (2013.01); *A61K 49/0052* (2013.01); *A61K 51/0482* (2013.01)

(58) Field of Classification Search
CPC ............ A61K 2123/00; A61K 2121/00; A61K 49/00; A61K 49/0021; A61K 51/00; A61K 51/0482; A61K 49/0052; A61P 9/00; A61P 37/06; A61P 37/02; A61P 35/00; A61P 31/04; A61P 25/00; C07D 487/08
USPC .......... 424/1.11, 1.49, 1.65, 1.69, 1.73, 1.81, 424/1.85, 1.89, 9.1, 9.2, 9.3, 9.4, 9.5, 9.6; 534/7, 10–16; 514/1, 1.1; 530/300
See application file for complete search history.

(56) References Cited

U.S. PATENT DOCUMENTS

| | | |
|---|---|---|
| 4,497,737 A | 2/1985 | Sargeson et al. |
| 5,652,361 A | 7/1997 | Simon et al. |
| 6,869,589 B1 * | 3/2005 | Smith ................ A61K 51/1072 424/1.65 |
| 10,717,741 B2 * | 7/2020 | Smith .................. C07D 487/08 |
| 2010/0196271 A1 | 8/2010 | Conti et al. |
| 2014/0219915 A1 | 8/2014 | Smith et al. |

FOREIGN PATENT DOCUMENTS

| | | |
|---|---|---|
| WO | WO-2000040585 A1 | 7/2000 |
| WO | WO-2010063069 A1 | 6/2010 |

OTHER PUBLICATIONS

Cai et al, Current Radiopharmacueticals, vol. 4, No. 1, pp. 68-74 (Year: 2011).*
Cai et al, Bioconjugate Chem., vol. 21, No. 8, pp. 1417-1424 (Year: 2010).*
Bottomley et al., "The Synthesis and Structure of Encapsulating Ligands: Properties of Bicyclic Hexamines," Aust. J. Chem., vol. 47, pp. 143-179, (1994).
Cai et al., "An improved synthesis and biological evaluation of a new cage-like bifunctional chelator, 4-((8-amino-3,6,10,13,16,19-hexaazabicyclo[6.6.6]icosane-1-ylamino)methyl)benzoic acid for $^{64}$Cu radiopharmaceuticals," Nuclear Medicine and Biology, vol. 37, pp. 57-65, (2010).
Cai et al., "Synthesis of a novel bifunctional chelator AmBaSar based on sarcophagine for peptide conjugation and $^{64}$Cu radiolabelling," Dalton Trans., pp. 5395-5400, (2009).
Di Bartolo et al., "Synthesis of a new cage ligand, SarAr, and its complexation with selected transition metal ions for potential use in radioimaging," J. Chem. Soc., Dalton Trans., pp. 2303-2309, (2001).
Dittrich et al., "Long tailed cage amines: Synthesis, metal complexation, and structure," Dalton Transactions, vol. 39, pp. 3433-3448, (2010).
Huang et al., "Biological Stability Evaluation of the α2ß1 Receptor Imaging Agents: Diamsar and DOTA Conjugated DGEA Peptide," Bioconjugate Chem., vol. 22, pp. 256-263, (2011).
International Search Report for PCT/AU2012/000817 dated Oct. 3, 2012.
Liu, et al., "Efficient Preparation and Biological Evaluation of a Novel Multivalency Bifunctional Chelator for $^{64}$Cu Radiopharmaceuticals," Chem. Eur. J., vol. 17, pp. 10222-10225, (2011).

(Continued)

*Primary Examiner* — D. L. Jones
(74) *Attorney, Agent, or Firm* — Dechert LLP

(57) ABSTRACT

Disclosed herein is a method for coupling a first compound having the formula (I) with a second compound that contains a carbonyl group. Also disclosed herein are compounds that can be formed by this method, and uses for such compounds.

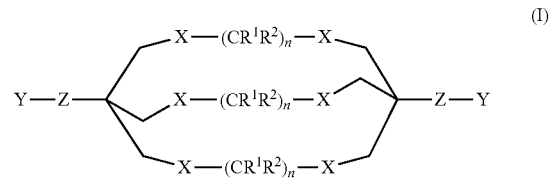

28 Claims, No Drawings

(56) References Cited

OTHER PUBLICATIONS

Mume et al., "Investigating the binding properties of porous drug delivery systems using nuclear sensors (radiotracers) and positron annihilation lifetime spectroscopy—Predicting conditions for optimum performance," Dalton Transactions, vol. 40, pp. 6278-6288, (2011).

Smith, S.V. "Sarar technology for the application of Copper-64 in biology and materials science," The Quarterly Journal of Nuclear Medicine and Molecular Imaging, vol. 52, No. 2, pp. 193-202, (2008).

Wei et al., "$^{64}$Cu-Labeled CB-TE2A and diamsar-conjugated RGD peptide analogs for targeting angiogenesis: comparison of their biological activity," Nuclear Medicine and Biology, vol. 36, pp. 277-285, (2009).

\* cited by examiner

CRYPTATE COMPOUNDS

CROSS-REFERENCE TO RELATED APPLICATIONS

This application is a continuation of U.S. patent application Ser. No. 14/129,855, filed Dec. 27, 2013, which is the national stage of International (PCT) Patent Application Serial No. PCT/AU2012/000817, filed Jul. 6, 2012, which claims the benefit of and priority to Australian patent application 2011902708, filed Jul. 7, 2011; the entire contents of U.S. patent application Ser. No. 14/129,855 and Australian patent application 2011902708 are hereby incorporated by reference.

FIELD OF THE INVENTION

The present invention relates to new methods for synthesising cryptand and/or cryptate compounds, and to new cryptand and/or cryptate compounds.

BACKGROUND TO THE INVENTION

The synthesis of cryptate compounds incorporating nitrogen or sulphur atoms was reported by Sargeson et al in the late 70s to early 80s. As shown in Scheme 1, these compounds can be prepared via a simple metal template process, capitalising on the inertness of Co(III) metal complexes. Reduction of the Co(III) complex of 1,8 dinitro-3,6,10,13,16,19-hexaazabicyclo[6.6.6]icosane (Co-"dinosar", compound 2) to produce the Co(II) complex of [3,6,10,13,16,19-hexaazabicyclo-[6.6.6]eicosane-1,8-diamine] ("Co-diamsar") was afforded with excess zinc metal powder in strong acid. The resultant Co-diamsar was then converted to its Co(III) metal complex (compound 3) with hydrogen peroxide prior to removal of the Co(III) to yield the free ligand ("diamsar"). Co(III) can then be removed from the cryptate compound using high concentrations of hydrochloric or hydrobromic acid (at 130 to 150° C.) or using excess cyanide ion, the latter producing the highest yield.

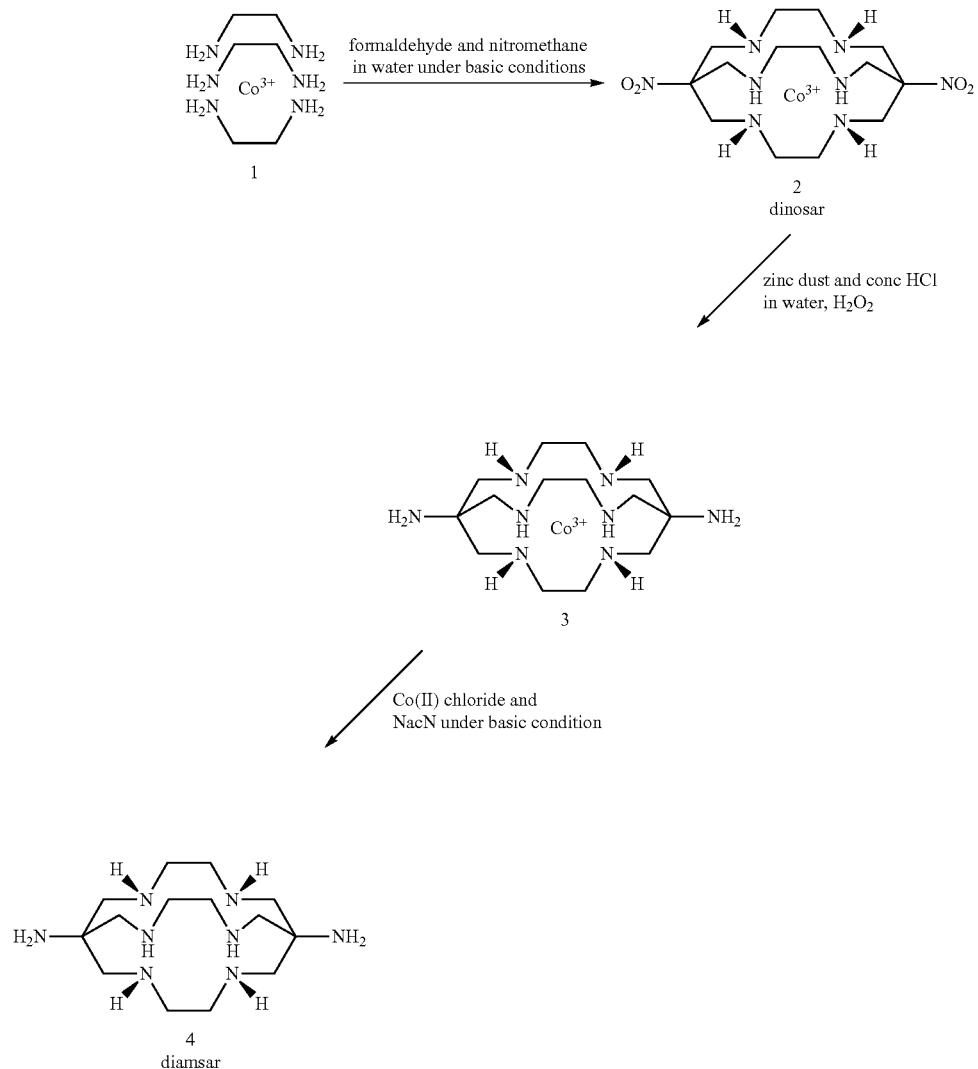

Scheme 1 - Synthesis of diamsar (compound 4)

The Cu(II) complex of diamsar can be used to form other cryptate or cryptand compounds such as 1-N-(4-aminobenzyl)-3,6,10,13,16,19-hexaazabicyclo[6.6.6]eicosane-1,8-diamine ("sarar", compound 8) via the reactions shown in Scheme 2. In this reaction, the Cu(II) acts as a templating metal tying up the secondary amines in a Cu(II) complex, thus reducing the potential for multiple by-products having substituted secondary amines.

make compounds in which diamsar is coupled to molecules other than nitrobenzyl aldehyde.

Sarar can be conjugated to a range of carrier agents, such as molecular recognition units, and used for imaging and therapy. For example, sarar-immunoconjugates have been demonstrated to be useful for $^{64}$Cu PET imaging and radiotherapy. Sarar is able to selectively complex $^{64}$Cu$^{2+}$ rapidly (within minutes) over a wide range of pH (4-9) values. The

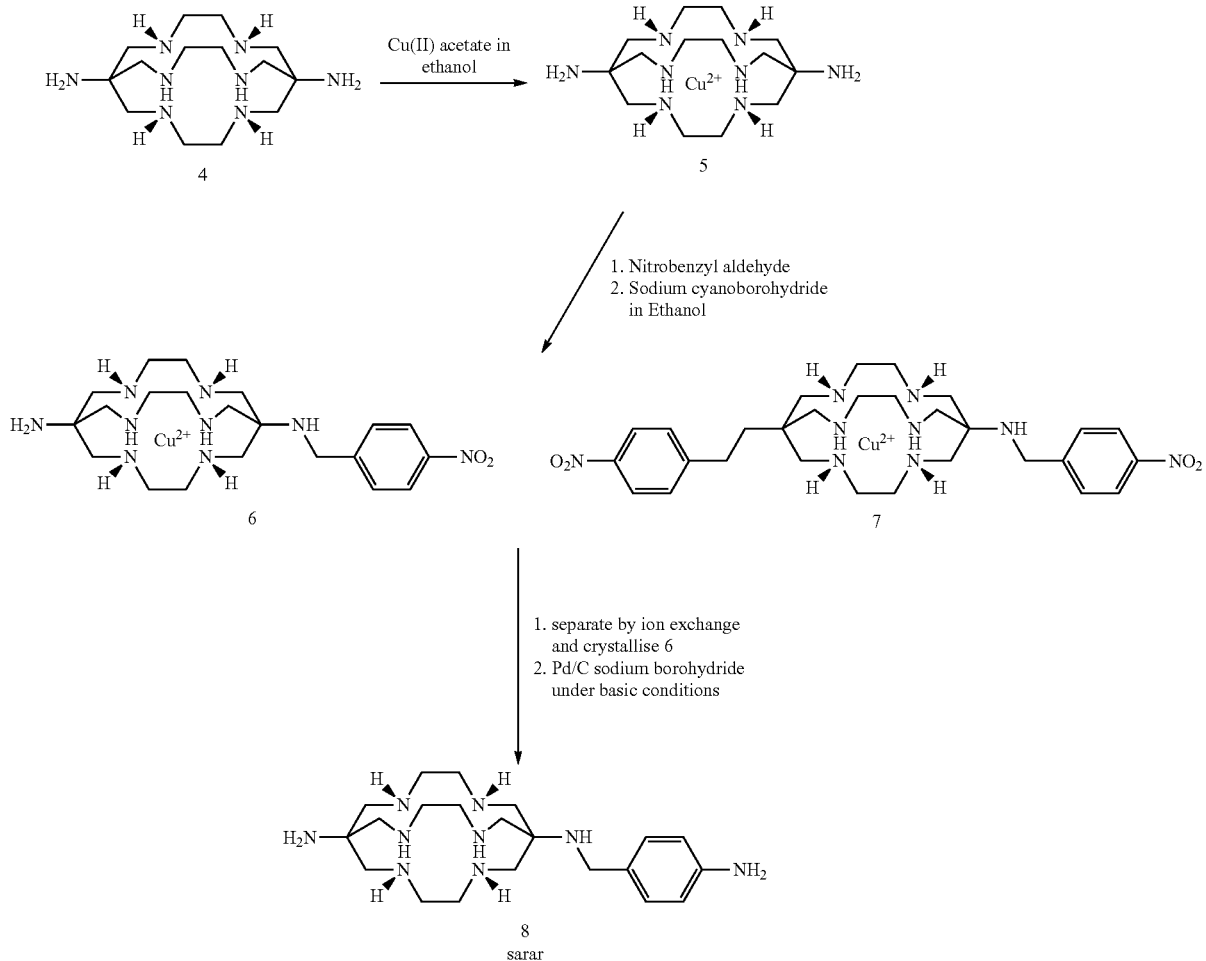

Coupling the Cu(II) complex of diamsar with nitrobenzyl aldehyde via Schiff base condensation in ethanol affords the synthesis of the desired mono-substituted diamsar in reasonable yield (25-30%), which then needs to be separated from the bis-substituted Cu(II) diamsar complex and unreacted Cu(II) diamsar. The separation can be achieved using ion exchange chromatography, but can be challenging. For example, yields are often compromised because of the need to change counter ions and because various forms of the complexes can precipitate on the column. Furthermore, such separations often require many litres of strong acid eluents, which then need to be disposed of. Removal of the Cu(II) is achieved under reducing conditions, for example, using palladium/charcoal and sodium borohydride, which also causes the nitrate to be converted into an aromatic amine. Minor variations of this reaction scheme have been used to $^{64}$Cu PET radiolabelling can take place at room temperature and results in kinetically inert complexes that are stable to excess EDTA challenge. Thus, high specific activity radiopharmaceutical products are easily prepared without the need for specialised skills or infrastructure and without requiring further purification steps.

It would be advantageous to provide alternative methods by which cryptand and/or cryptate compounds can be coupled with other molecules.

SUMMARY OF THE INVENTION

The inventors of the invention the subject of the present application have endeavoured to make new compounds in which a cryptand or cryptate compound is coupled with another molecule. However, they were unable to use prior art reaction mechanisms to make a number of target compounds because of the reducing conditions that are required to remove the templating metal (e.g. Cu(II)) from the cryptate compound in order to form the desired product.

In a first aspect, the present invention provides a method for coupling a first compound having the formula (I):

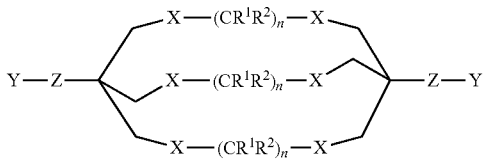

wherein:
each $R^1$ and $R^2$ is independently selected from the group consisting of hydrogen, halogen, $CH_3$, COOH, $NO_2$, $CH_2OH$, $H_2PO_4$, $HSO_3$, CN, C(=O)$NH_2$ and CHO;
n=2, 3 or 4;
each X is independently selected and is NH or S, provided that at least one X is NH;
each Z is an optional spacing group which, when present, is independently selected from the group consisting of optionally substituted $C_1$-$C_{10}$ alkyl, optionally substituted aryl and optionally substituted heterocycle; and
each Y is independently selected from the group consisting of hydrogen, halogen, hydroxyl, nitro, optionally substituted amino, optionally substituted alkyl, optionally substituted aryl, optionally substituted aralkyl, optionally substituted heterocycle, isothiocyanate, cyano, —NH—COCH$_2$Br, —COOR' and —NH—CO—CH=CH—COOR', wherein R' is hydrogen, an optionally substituted alkyl, or an optionally substituted aryl, provided that at least one Y is or contains a primary amine;
with a second compound that contains a carbonyl group (e.g. an aldehyde, ketone, carboxylic acid or ester). The method comprises the steps of:
exposing the compound having the formula (I) to reaction conditions whereby substantially all coupling will occur at the primary amine; and
causing the second compound that contains a carbonyl group to react with and couple to the compound having the formula (I).

The inventors have surprisingly discovered that it is not necessary for cryptand compounds (e.g. diamsar or other compounds of formula (I)) to contain a templating metal (e.g. Cu(II)) in order to cause substantially all of the coupling to occur at only the primary amine(s) of the cryptand compound. The inventors discovered that altering the reaction conditions under which the Schiff base condensation reactions are caused to occur from those conventionally used results in substantially all of the coupling reactions occurring at only the primary amine(s). This discovery was especially unexpected because all prior art in this field teaches either the use of a metal complex or protective groups to deactivate the secondary amines.

The method of the present invention does not require the use of a metal complex or protective groups to deactivate the secondary amine(s), and involves fewer steps than prior art processes for coupling a cryptand (or cryptate) compound of formula (I) with another compound. The method of the present invention can therefore be carried out more quickly and with less expense than prior art processes. The inventors have found that the methods of the present invention can provide an identifiable reduction in the cost in consumables and the time taken in producing the coupled cryptand or cryptate compounds. The inventors have also surprisingly found that the methods of the present invention can result in higher yields of mono-substituted cryptand or cryptate compounds (up to about 45%) when compared with the prior art methods (up to about 30%).

As it is not necessary to remove a templating metal (e.g. Cu(II)) in the method of the present invention, then it is not necessary to subsequently perform the reduction reactions required by the prior art methods to remove the templating metal. As such, coupled cryptand compounds containing functional groups that would have been reduced during such reduction reactions can now be readily synthesised.

The compound of formula (I) may be not complexed with a metal ion. It may be a metal free compound.

The invention also encompasses a product made by the method of the first aspect. The product may be not complexed with a metal ion. It may be metal free.

In an embodiment there is provided a method for coupling a first compound having the formula (Ia):

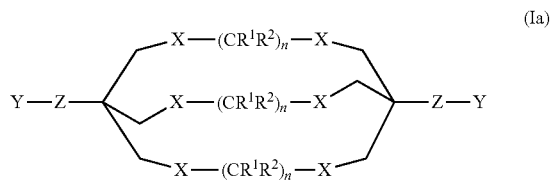

wherein:
each $R^1$ and $R^2$ is hydrogen;
n=2;
each X is NH;
each Z is absent; and
each Y is $NH_2$;
with a second compound that contains an aldehyde group. The method comprises the steps of:
exposing the compound having the formula (Ia) to reaction conditions whereby substantially all coupling will occur at the primary amine; and
causing the second compound that contains an aldehyde group to react with and couple to the compound having the formula (Ia).

The conditions whereby substantially all coupling will occur at the primary amine may comprise pH about 4.5. The reaction may be conducted in a protic solvent, e.g. an aqueous and/or alcoholic solvent.

In another embodiment there is provided a method for coupling a first compound having the formula (Ia):

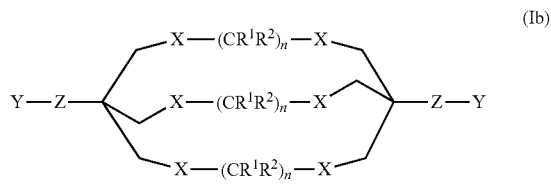

wherein:
each $R^1$ and $R^2$ is hydrogen;
n=2;
each X is NH;
one Z is absent and the other Z is -(p-$C_6H_4$)—$CH_2NH$; and
each Y is $NH_2$;
with a second compound that contains a —COOH group. The method comprises the steps of:
exposing the compound having the formula (Ia) to reaction conditions whereby substantially all coupling will occur at the primary amine attached to -(p-$C_6H_4$)—$CH_2NH$; and
causing the second compound that contains the —COOH group to react with and couple to the compound having the formula (Ib).

Accordingly, in a second aspect, the present invention provides a compound having the formula (II):

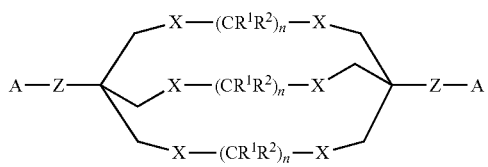

wherein:
each $R^1$ and $R^2$ is independently selected from the group consisting of hydrogen, halogen, $CH_3$, COOH, $NO_2$, $CH_2OH$, $H_2PO_4$, $HSO_3$, CN, C(=O)$NH_2$ and CHO;
n=2, 3 or 4;
each X is independently selected and is NH or S, provided that at least one X is NH;
each Z is an optional spacing group which, when present, is independently selected from the group consisting of an optionally substituted $C_1$-$C_{10}$ alkyl, optionally substituted aryl and optionally substituted heterocycle;
each A is independently selected from the group consisting of hydrogen, halogen, hydroxyl, nitro, optionally substituted amino, optionally substituted alkyl, optionally substituted aryl, optionally substituted aralkyl, optionally substituted heterocycle, isothiocyanate, cyano, —NH—$COCH_2Br$, —COOR', —$NHCR^3R^4R^5$ and —NH—CO—CH=CH—COOR', provided that at least one A is or contains —$NHCR^3R^4R^5$;
R' is selected from the group consisting of hydrogen, optionally substituted alkyl and optionally substituted aryl;
$R^3$ and $R^4$ are independently selected from the group consisting of: H, alkyl and aryl; and
$R^5$ is a functional group or a species containing a functional group that would be reduced under reducing conditions.

The compounds of formula (II) contain $R^5$, which is a functional group or a species containing a functional group that would be reduced under the reducing conditions required by the prior art to remove a templating metal (e.g. Cu(II)) from the coupled cryptate compound. The functional group or species containing the functional group may be reducible by palladium/charcoal or by sodium borohydride or by both. Such compounds would not be possible to directly synthesise via an intermediate in which the coupled cryptate compound contains a templating metal such as Cu(II) because the functional group would be reduced when the templating metal was removed from the coupled cryptate compound. $R^5$ may for example be, or may contain, an alkene, and alkyne, a nitro group, a maleimido group, a phthalimido group or some other reducible group. The compound of formula (II) may be not complexed with a metal ion. It may be a metal free compound. It may be uncomplexed. Alternatively it may be complexed, optionally through one or more Xs of the formula, with a metal atom or metal ion.

In some embodiments, $R^5$ is an optionally substituted alkyl, aryl or heterocycle which is substituted with a functional group that would be reduced under reducing conditions. In particular embodiments $R^5$ is an optionally substituted alkyl, aryl or heterocycle which is substituted with a functional group that would be reduced under reducing conditions, each $R^1$ and $R^2$ is hydrogen, n=2 and each X is NH.

In some embodiments, $R^5$ has the following structure:

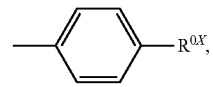

wherein $R^{OX}$ is a functional group that would be reduced under reducing conditions.

In particular embodiments $R^5$ has the structure shown above, each $R^1$ and $R^2$ is hydrogen, n=2 and each X is NH.

In some embodiments, the functional group in $R^5$ is selected from the group consisting of: —$NO_2$, —$N_3$, —C≡CH, —C≡N, —O—$(CR^1R^2)_m$—$NH_2$, —$(CR^1R^2)_m$—SH, —C(=O)—O—$CH_3$, —C(=O)—O—$(CR^1R^2)_m$—$CH_3$,

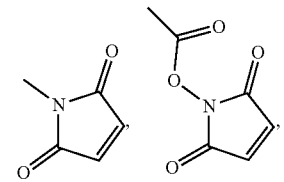

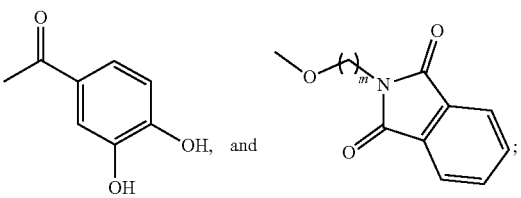

wherein $R^1$ and $R^2$ are as defined above and m is 1 to 8.

In some embodiments, $R^1$, $R^2$, $R^3$ and $R^4$ are H, n is 2 and each X is NH.

The invention also encompasses a compound according to the second aspect (or the third aspect, below) which is made by the method of the first aspect.

In a third aspect, the present invention provides a compound having any one of the following structures:
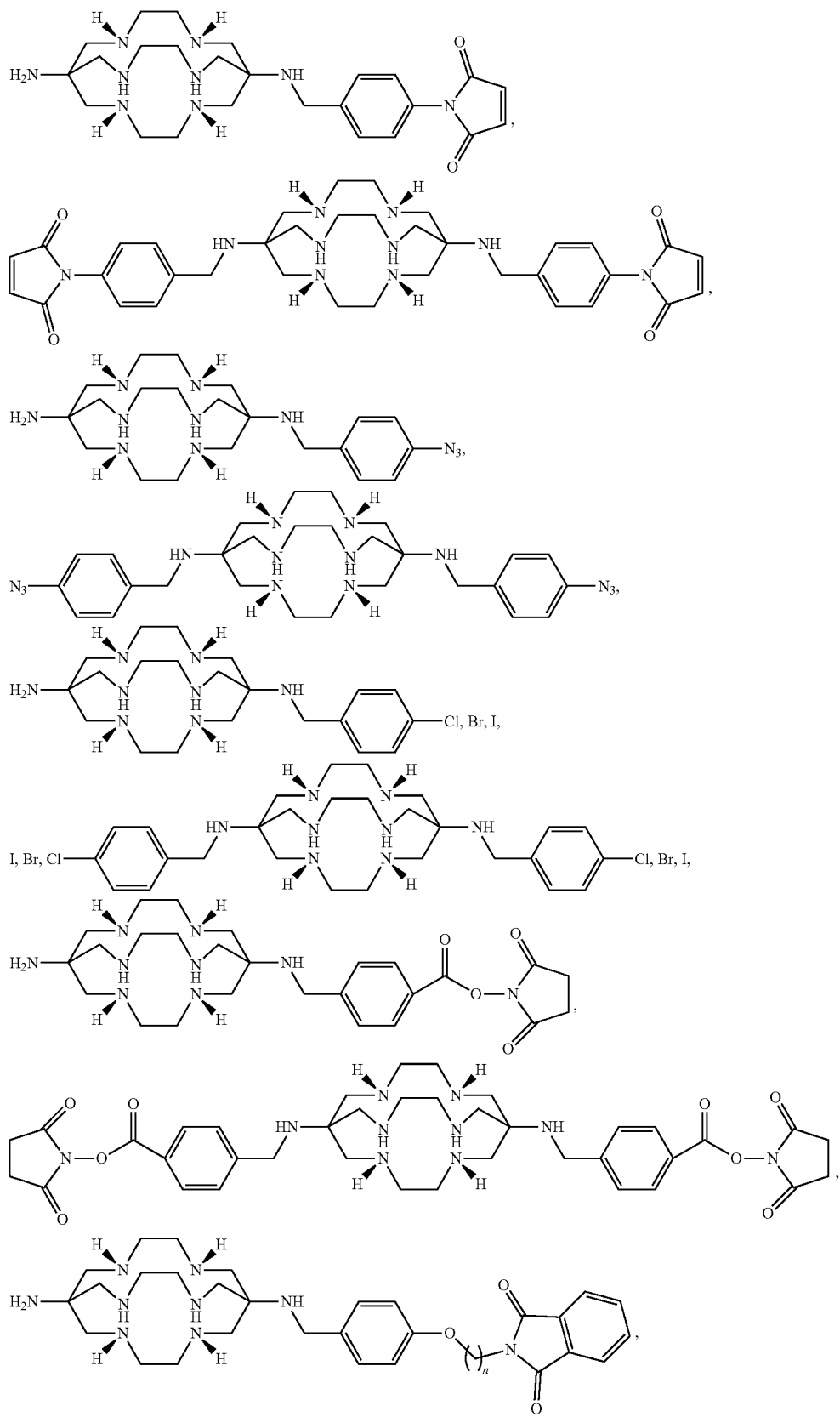

-continued
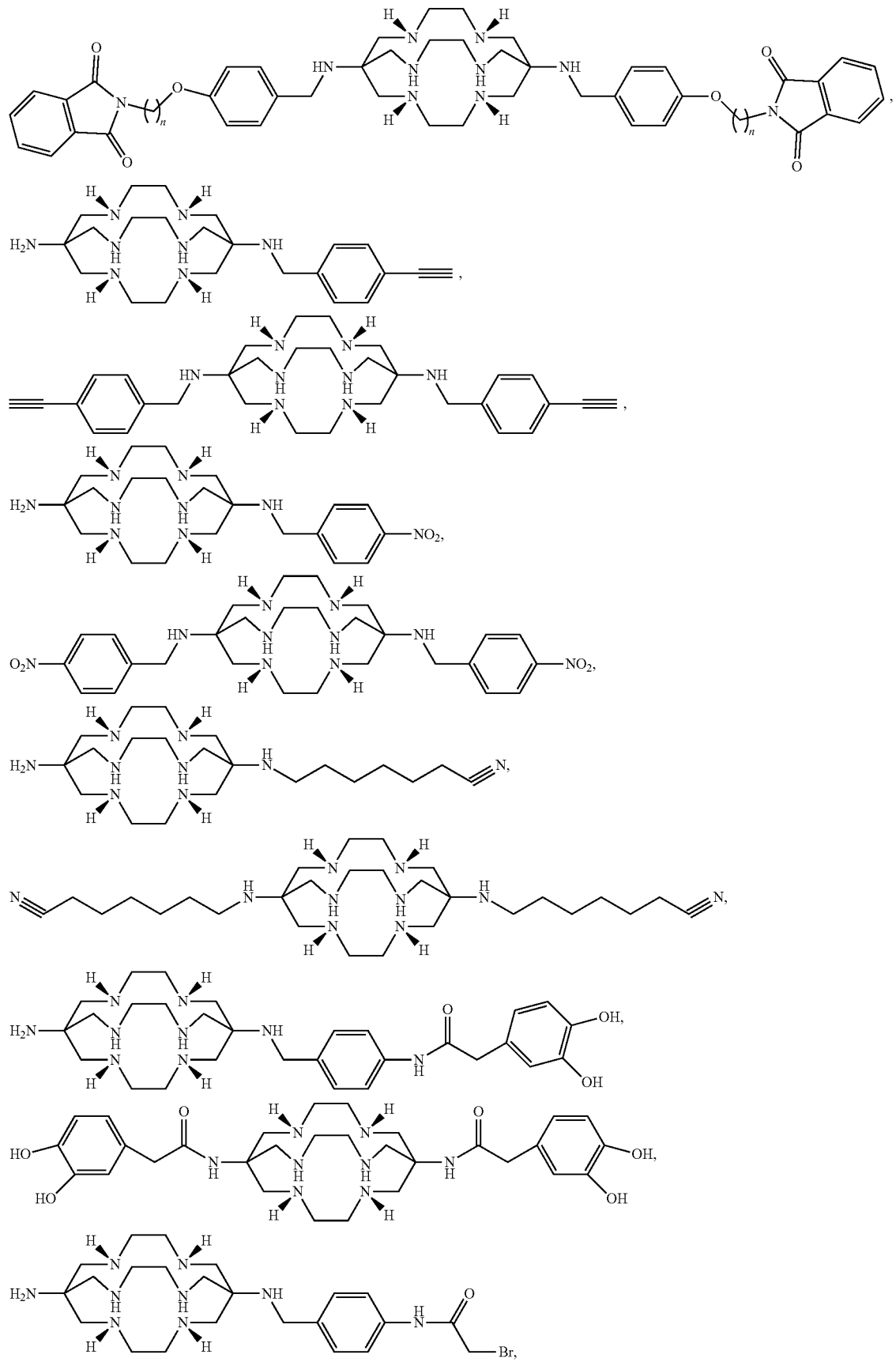

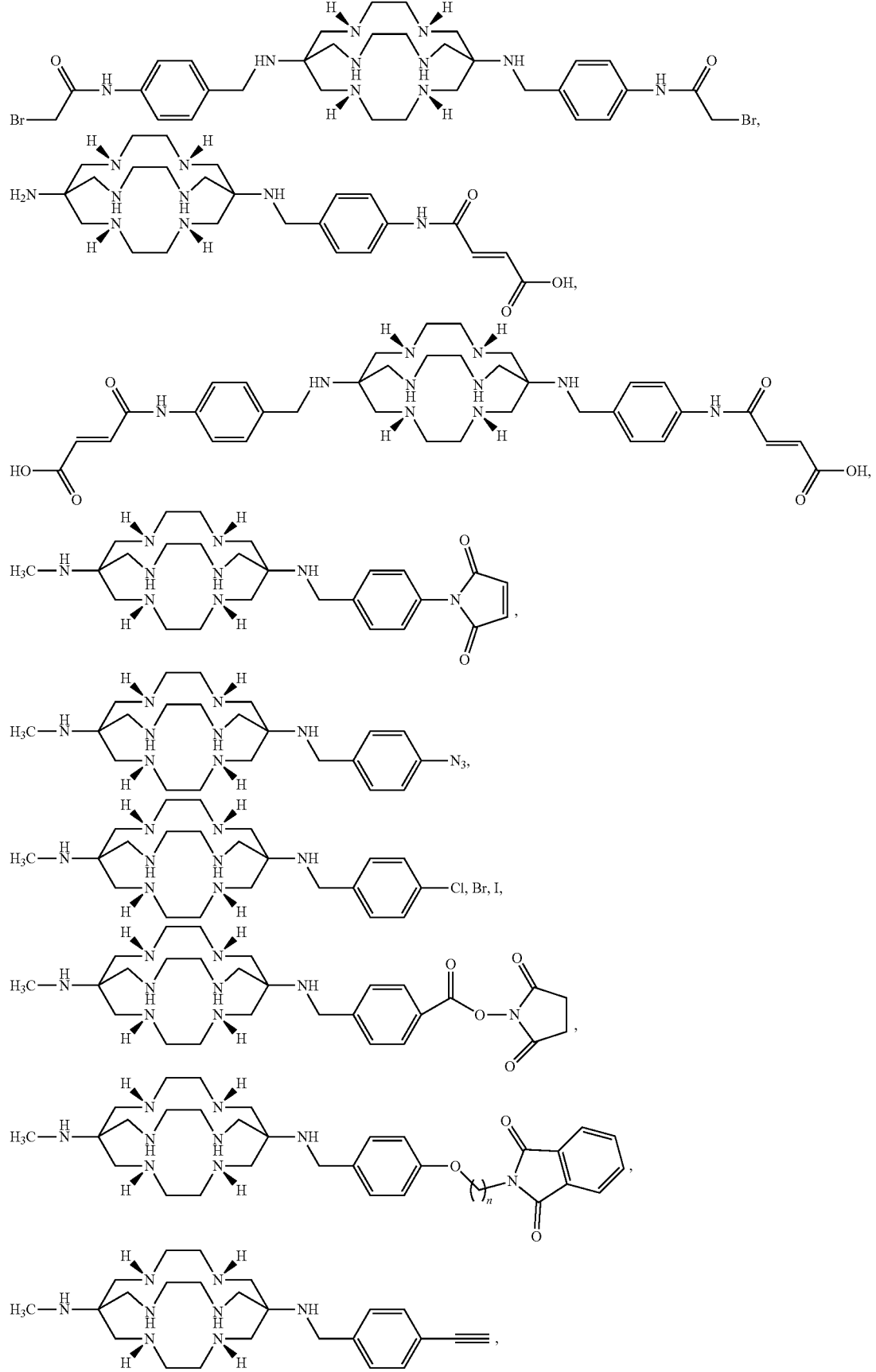

-continued
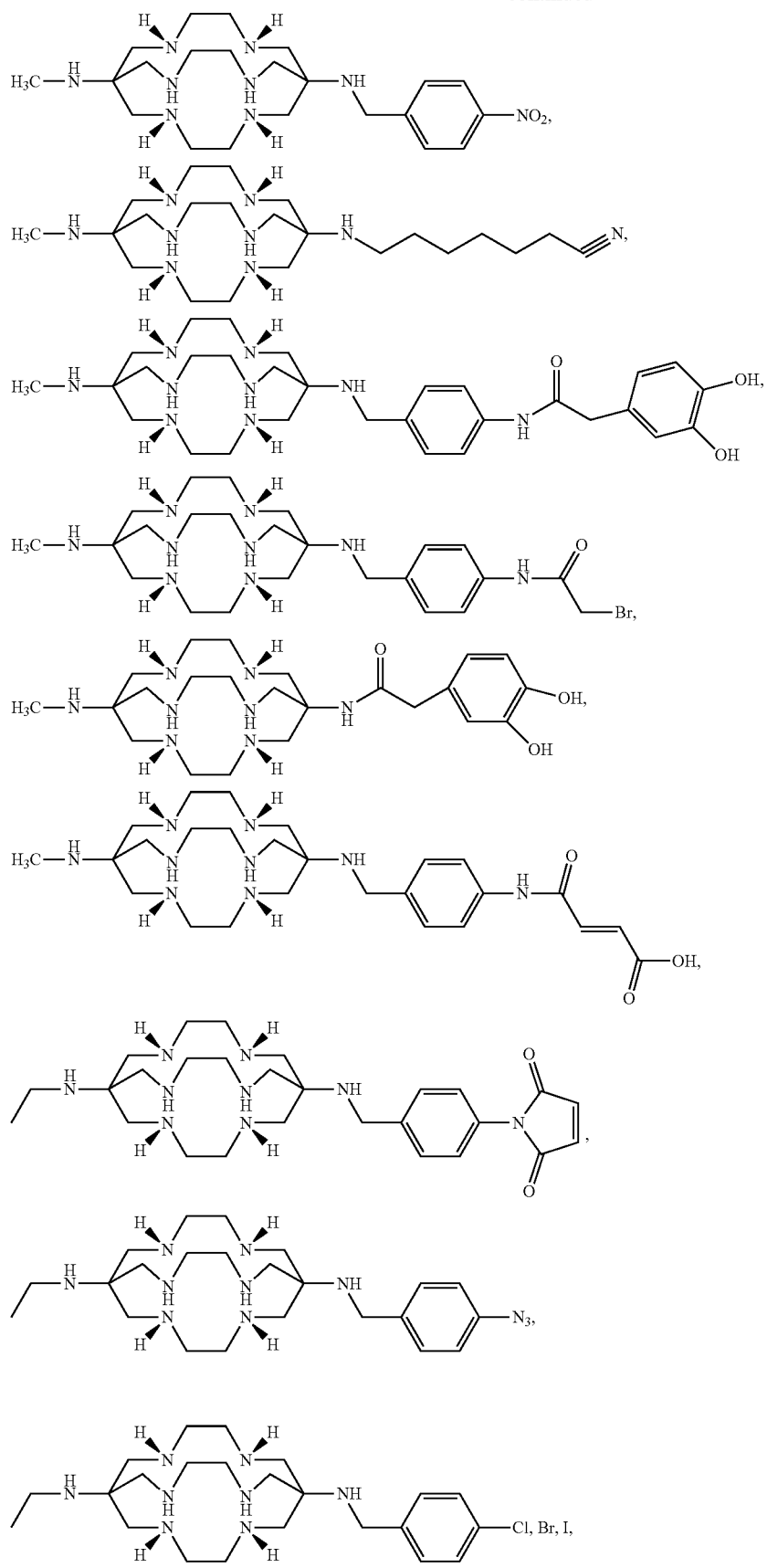

-continued
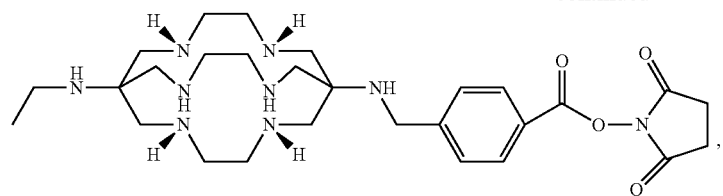
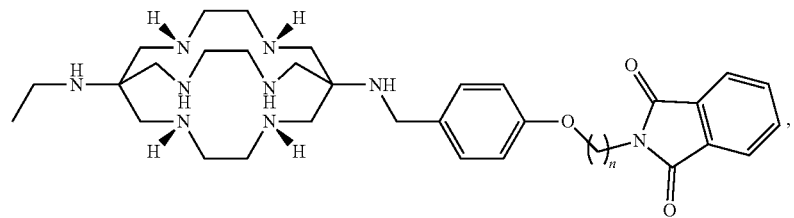
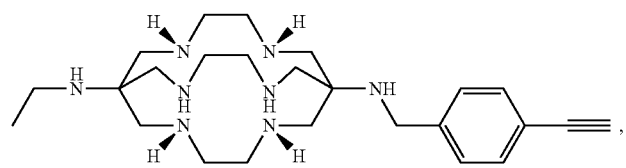
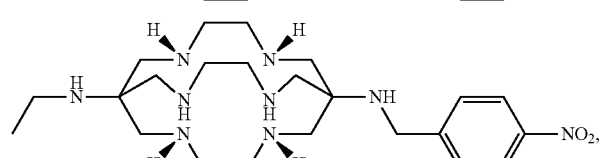
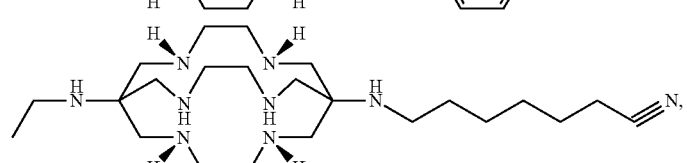
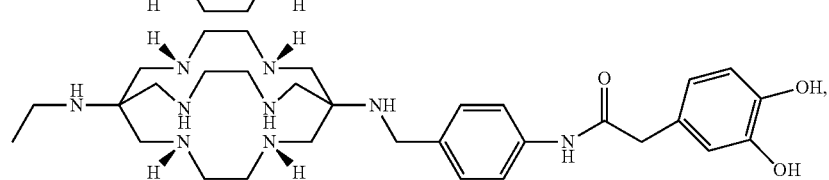
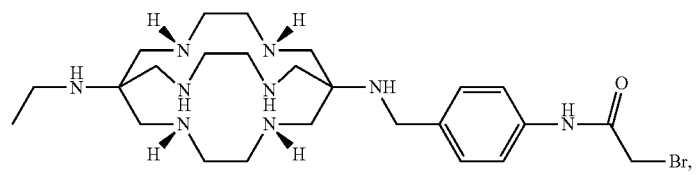
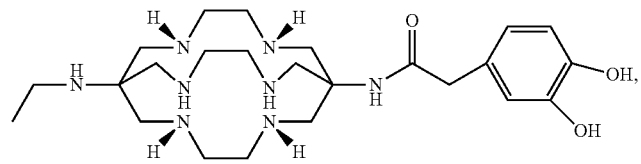
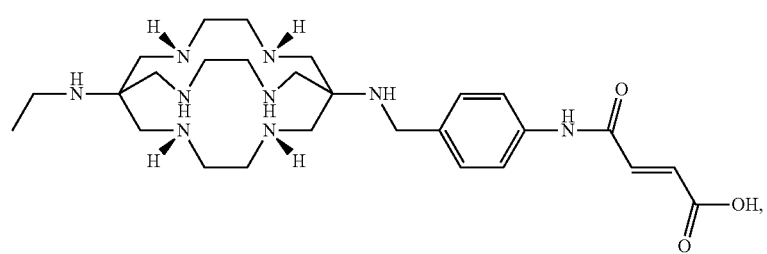

-continued
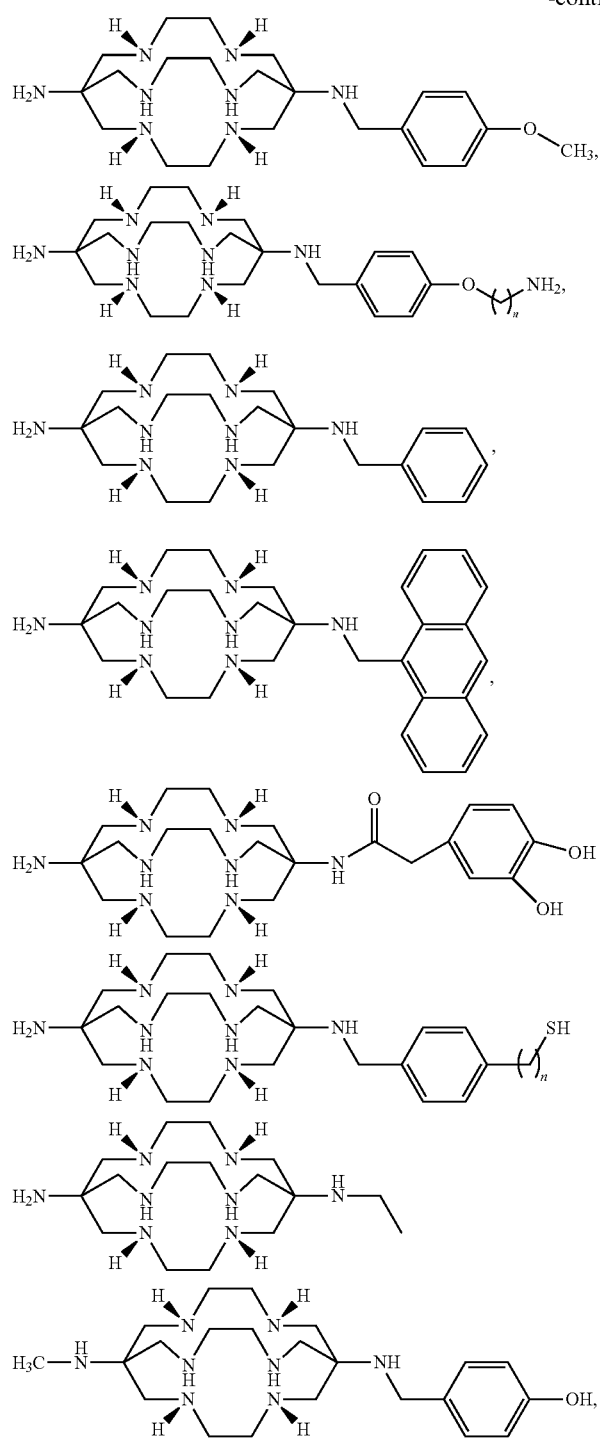
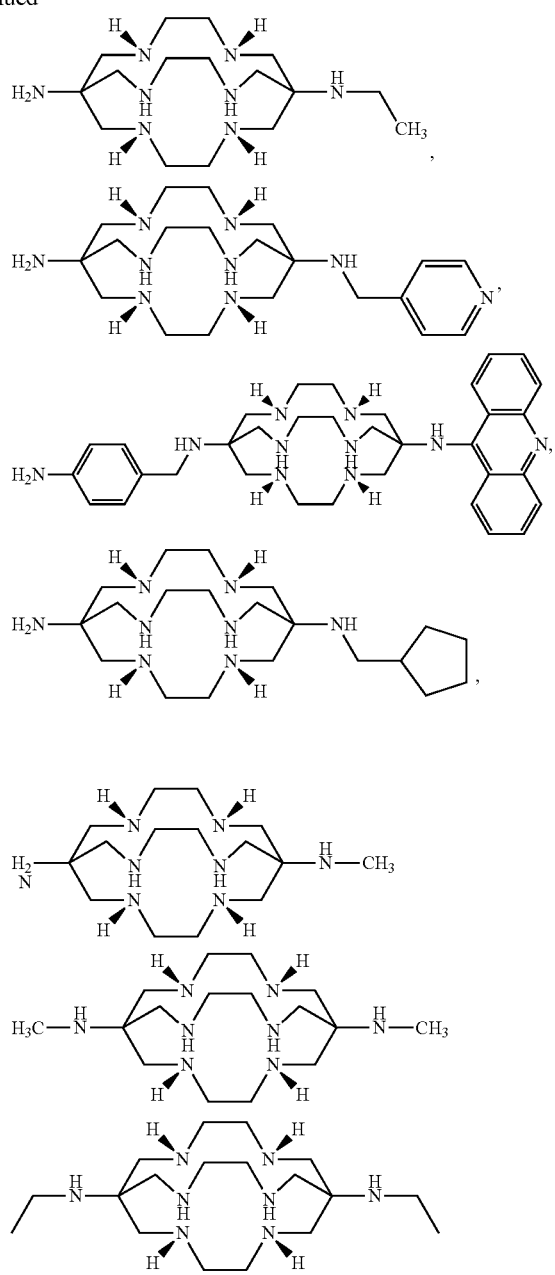
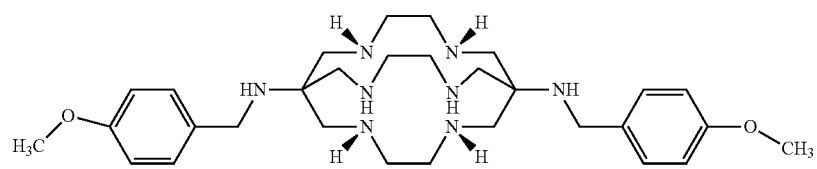

wherein n is an integer of from 1 to 5 and the references to "Cl, Br, I" in the above structures refer to different compounds having a Cl, Br or I atom at the indicated (para) position, or at the meta or ortho position.

The present invention also provides compounds having structures similar to those set out above, but in which ethylene groups linking the chelating atoms in the cryptand compounds are replaced with propylene or butylene groups (i.e. n is 3 or 4 in the compound of formula (I)).

The present invention also provides compounds having structures similar to those set out above, but in which between one and five (e.g. 1, 2, 3, 4 or 5) of the chelating amines in the cryptand compounds are replaced with S (i.e. between 1 and 5 of the X's in the compound of formula (I) is S).

In a fourth aspect, the present invention provides a mono-substituted cryptand or cryptate compound produced by the method of the first aspect of the present invention. An exemplary compound of the fourth aspect of the present invention is:

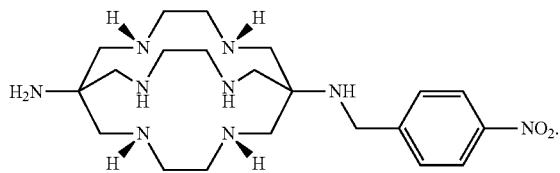

In a fifth aspect, the present invention provides a bis-substituted cryptand or cryptate compound produced by the method of the first aspect of the present invention. An exemplary compound of the fifth aspect of the present invention is:

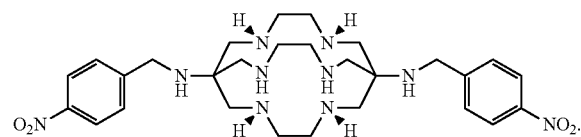

In a sixth aspect, the present invention provides a conjugated compound comprising at least one compound according to the second to fifth aspects of the present invention conjugated to at least one carrier agent (e.g. a molecular recognition unit).

In embodiments of the second to sixth aspects of the invention, the compound is complexed with a metal ion. In other embodiments the compound is not complexed with a metal ion. In particular, if the compound is complexed with a metal ion, it may be complexed to the heteroatoms of the cryptand ring system of the compound.

In a seventh aspect, the present invention provides a pharmaceutical composition comprising a compound according to the second to sixth aspects of the present invention, or a pharmaceutically acceptable salt thereof, and a pharmaceutically acceptable carrier.

In an eighth aspect, the present invention provides a method for diagnosing a disease, a method for radioimaging, or a method for radiotherapy of a disease in a subject. The method comprises administering to the subject an effective amount of a radiolabelled complex of a compound according to the second to sixth aspects of the present invention, or a pharmaceutically acceptable salt thereof, or a pharmaceutical composition according to the seventh aspect of the present invention.

In a ninth aspect, the present invention provides the use of a radiolabelled complex of a compound according to the second to sixth aspects of the present invention, or a pharmaceutically acceptable salt thereof, in the manufacture of a medicament for diagnosing a disease, radioimaging, or radiotherapy of a disease.

In a tenth aspect, the present invention provides a method for diagnosing a disease, a method for imaging, or a method for therapy of a disease in a subject. The method comprises administering to the subject an effective amount of a compound according to the second to sixth aspects of the present invention, or a pharmaceutically acceptable salt thereof, or a pharmaceutical composition according to the seventh aspect of the present invention.

In an eleventh aspect, the present invention provides the use of a compound according to the second to sixth aspects of the present invention, or a pharmaceutically acceptable salt thereof, in the manufacture of a medicament for diagnosing a disease, imaging, or therapy of a disease.

In a twelfth aspect, the present invention provides a kit. The kit comprises a compound according to the second to sixth aspects of the present invention, or a pharmaceutically acceptable salt thereof, in a first container, and a species containing a metal ion in a second container.

DETAILED DESCRIPTION OF THE INVENTION

As discussed above, the present invention provides a method for coupling a first compound having the formula (I):

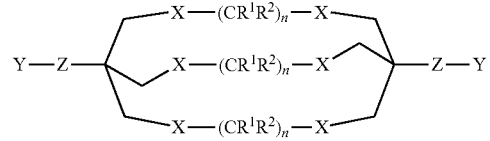

wherein:
each $R^1$ and $R^2$ is independently selected from the group consisting of hydrogen, halogen, $CH_3$, COOH, $NO_2$, $CH_2OH$, $H_2PO_4$, $HSO_3$, CN, C($=$O)$NH_2$ and CHO;
n=2, 3 or 4;
each X is independently selected and is NH or S, provided that at least one X is NH;
each Z is an optional spacing group which, when present, is independently selected from the group consisting of optionally substituted $C_1$-$C_{10}$ alkyl, optionally substituted aryl and optionally substituted heterocycle; and
each Y is independently selected from the group consisting of hydrogen, halogen, hydroxyl, nitro, optionally substituted amino, optionally substituted alkyl, optionally substituted aryl, optionally substituted aralkyl, optionally substituted heterocycle, isothiocyanate, cyano, —NH—COCH$_2$Br, —COOR' and —NH—CO—CH$=$CH—COOR', wherein R' is hydrogen, an optionally substituted alkyl, or an optionally substituted aryl, provided that at least one Y is or contains a primary amine;

with a second compound that contains a carbonyl group. The method comprises the steps of:

exposing the compound having the formula (I) to reaction conditions whereby substantially all coupling will occur at the primary amine; and causing the second compound that contains a carbonyl group to react with and couple to the compound having the formula (I).

The method of the present invention includes a Schiff base condensation in which the compound of formula (I) is coupled with the second compound that contains a carbonyl group (for example, an aldehyde or a ketone) via the formation of an imine. Advantageously, the method of the present invention can be performed in the absence of a templating metal (e.g. Cu(II)) in the cryptand compound. It may be performed using a compound of formula (I) which is not complexed with a metal or metal ion, in particular in which the cryptand ring system of the compound is not complexed with a metal or metal ion. The method also includes an amide formation in which the compound of formula (I) is coupled with the second compound that contains a carbonyl group (for example a carboxylic acid) via the formation of an amide.

When attempting to widen their portfolio of cryptand- and cryptate-based compounds, the inventors attempted to make new series of mono-substituted and bis-substituted derivatives of basic cryptand or cryptate compounds containing a maleimide group. However, the inventors found that they were unable to remove the Cu(II) ion from the cryptate compound without reducing the maleimide group, which rendered the final product inactive. The inventors therefore decided to re-evaluate their methods and surprisingly discovered that by carefully controlling the reaction conditions before and during the Schiff base condensation, it is not actually necessary to have a templating metal (or other organic protecting groups) in order to effectively protect the secondary amine(s) from undergoing further reactions and selectively obtain the desired products.

Without wishing to be bound by theory, the inventors' believe that the primary amines are the least basic of the amines in the compound of formula (I). The inventors surprisingly found that if the condensation reaction, e.g. Schiff base condensation, was suitably slowed down, the secondary amine became inactive (possibly because it became protonated and/or sterically hindered) and the primary amines became the preferential site for coupling of the carbonyl containing compound.

The inventors then conducted a comprehensive investigation into the various reaction conditions that could be applied in order to control the Schiff base condensation reactions (e.g. removal of heat, reduce molar ratios of reactions, use of polar solvent such as water and mildly acidic conditions). The inventors surprisingly found that not only could the desired mono-substituted cryptand compounds be formed in the absence of the Cu(II) metal ion templating agent, but also that production of bis-substituted cryptand compounds was substantially reduced in some cases. Thus, higher yields of some mono-substituted cryptand compounds can be obtained using the methods of the present invention.

In some embodiments, the method comprises the steps of dissolving the compound having the formula (I) in a solvent comprising at least some water to form a solution; and adding to the solution the second compound that contains a carbonyl group. The primary amine and carbonyl groups of these compounds will react with each other to form an imine group and thus couple the compounds. The molar ratio of these the compound of formula (I) to the second compound may be between about 1:0.8 and 1:3, or about 1:1 to 1:3, 1:1.5 and 1:3, 1:2 and 1:3, 1:0.8 and 1:2, 1:0.8 and 1:1.5 or 1:1 and 1:2, e.g. about 1:0.8, 1:0.9, 1:1, 1:1.1, 1:1.2, 1:1.3, 1:1.4, 1:1.5, 1:2, 1:2.5 or 1:3. The reaction may be conducted under a normal air atmosphere. It may be conducted under non-anhydrous conditions.

The solvent may be protic. It may be aqueous. It may be alcoholic. It may be both alcoholic and aqueous. The solvent may, for example be a mixture of water and one or more of ethanol, dimethylformamide, acetonitrile, methanol, isopropanol, tetrahydrofuran and propanol. For example, the solvent may contain between 10% and 50% water. Alternatively the solvent may be water, or may be ethanol. Previously, Schiff base condensation reactions involving compounds similar to those used in the present invention were generally carried out in water-free solvents (such as dry ethanol) or in the presence of molecular sieves to aid in the removal of water produced during the reaction and thus force the equilibrium towards the formation of the imine.

In some embodiments, the solution is mildly acidic. It may have a pH between about 3 and 6.5, or between about 3.5 and 6.5, 4 and 6.5, 4.5 and 6.5, 5 and 6.5, 5.5 and 6.5 or 6 and 6.5. The pH may be about 3, 3.5, 4, 4.5, 5, 5.5, 6 or 6.5.

In some embodiments, the pH of the solution is from about 4 to about 5, or about 3 to 5, 4 to 6.

In some embodiments, the mildly acidic conditions are caused by adding acetic acid, or by adding formic acid, or by adding hydrochloric acid, etc to the solution. In general the mildly acidic conditions may be caused by adding an acid to the solution. The acid may be a mineral acid or may be an organic acid, e.g. a carboxylic acid. In some instances the solution is buffered to the desired pH. In cases where the solvent is ethanol, the acid used to generate the mildly acidic conditions may be an organic acid, e.g. acetic acid. In cases where the solvent is water, the acid used to generate the mildly acidic conditions may be an inorganic acid, e.g. hydrochloric acid.

In some embodiments, a reducing agent (e.g. a borohydride reducing agent such as sodium cyanoborohydride, sodium borohydride or sodium triacetoxyborohydride) is added to the solution. The reducing agent reduces the imine group, generated by coupling of a primary amine of the compound of formula (I) and a compound comprising an aldehyde group, to an amine group, thus resulting in a coupled cryptand or cryptate compound in which the compound of formula (I) is coupled with the second compound via an amine group. The reducing agent may therefore be a selective reducing agent. It may be a mild reducing agent. It may be a reducing agent capable of reducing an imine to an amine without reducing other functional groups present in the initial condensation product formed in the reaction.

Typically, the reducing agent is added to the solution after the compound of formula (I) and the second compound had been given sufficient time to react to form the imine group and thus become coupled. Depending on the particular compounds involved in this reaction, this may take from a few minutes to a few days. Alternatively, the reducing agent may be added to the solution at the same time as (or shortly after, or even before) the compound of formula (I) or second compound is added to the solution.

In some embodiments, the method comprises the further step or steps of separating products of the coupling reaction. That is, separating the unreacted compound having the formula (I), the mono-substituted cryptand compound and, if each Y is or contains a primary amine, the bis-substituted cryptand compound. This separation may, for example be carried out by flash chromatography using eluents consisting of mixtures of methanol, chloroform or dichloromethane, by using a C18 column using eluents with mixtures of methanol, acetonitrile and/or water or by precipitation from water, methanol or ethanol.

Exemplary compounds which can be produced using the method of the present invention include the following:

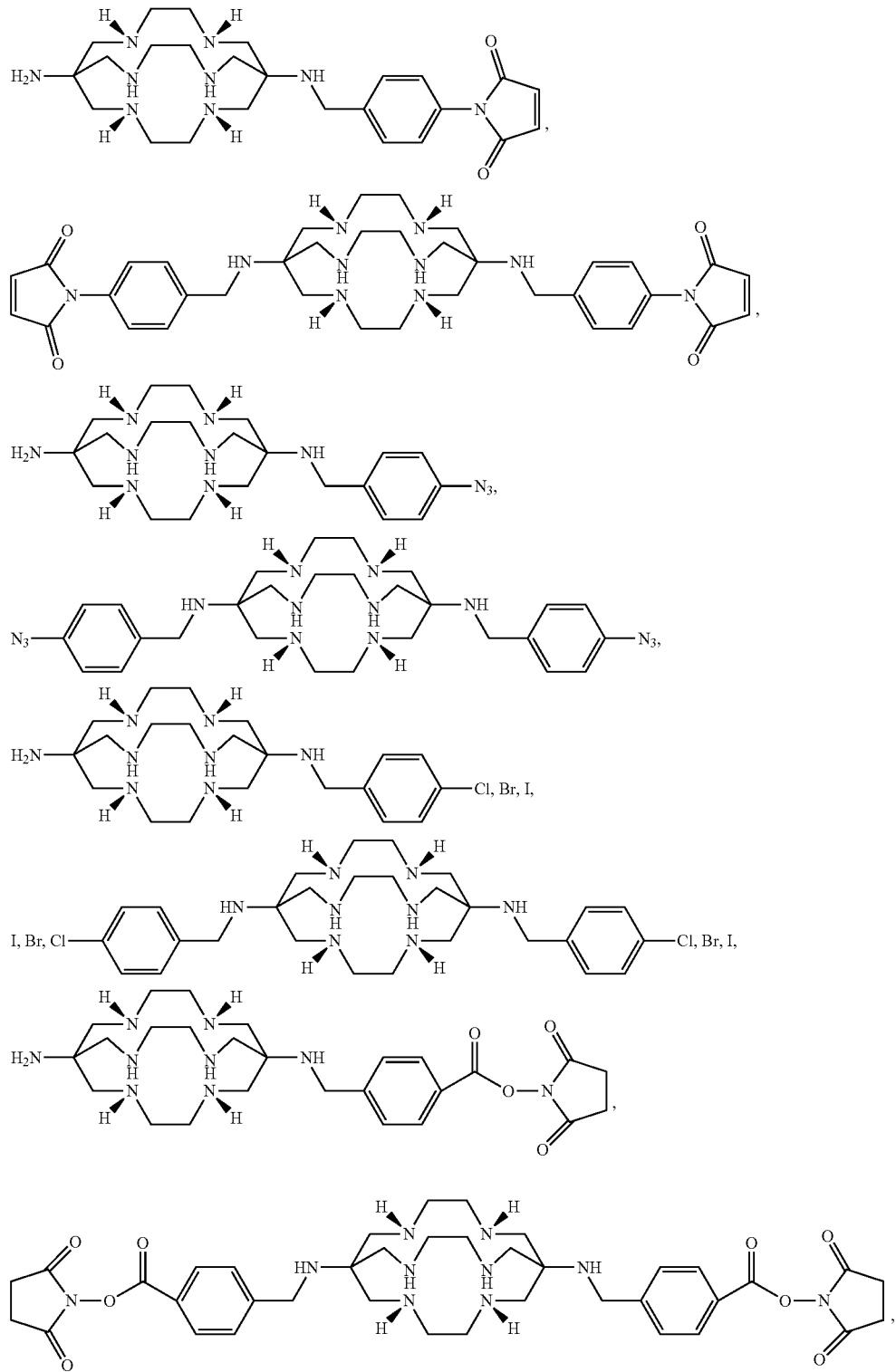

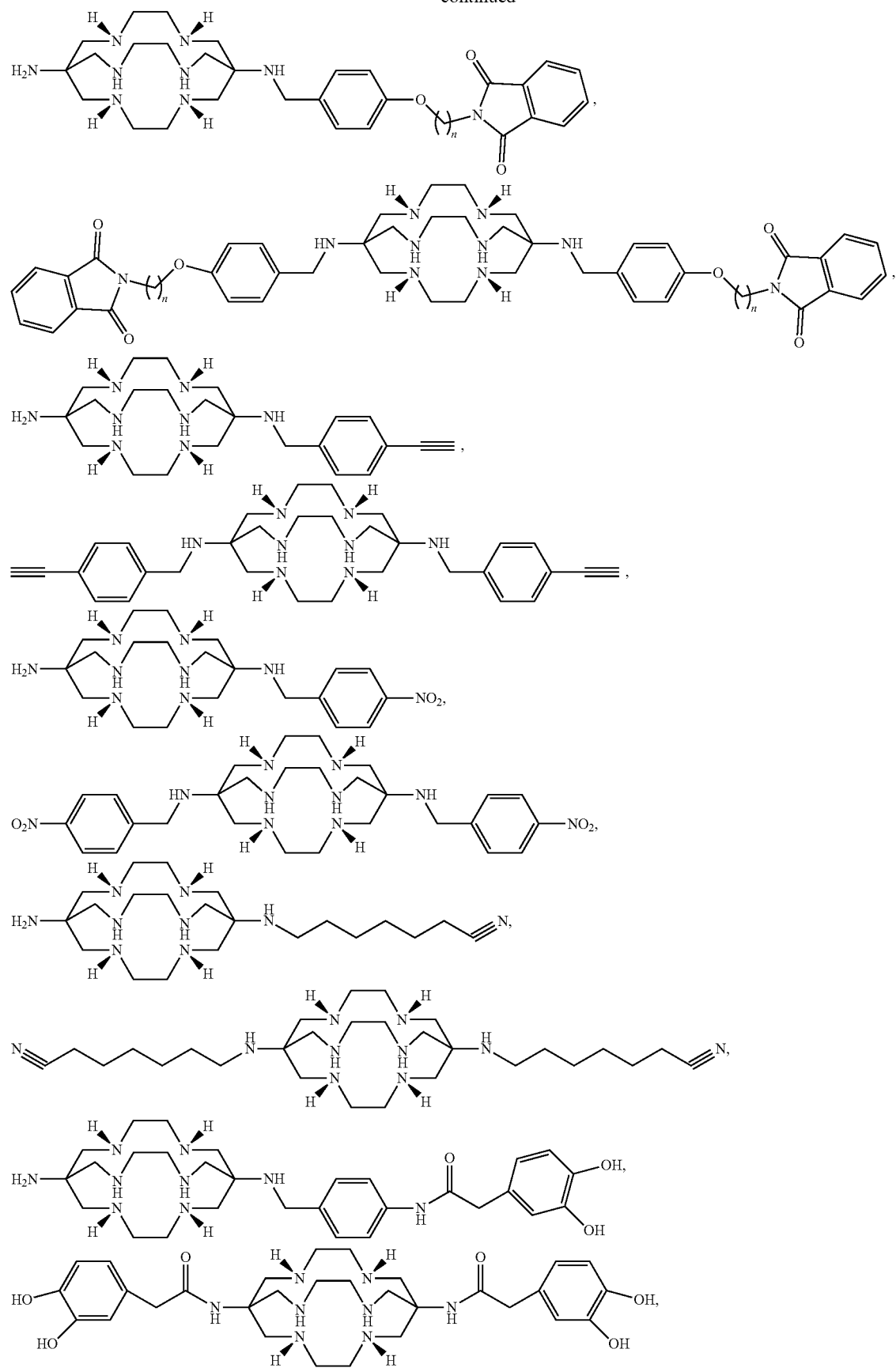

-continued
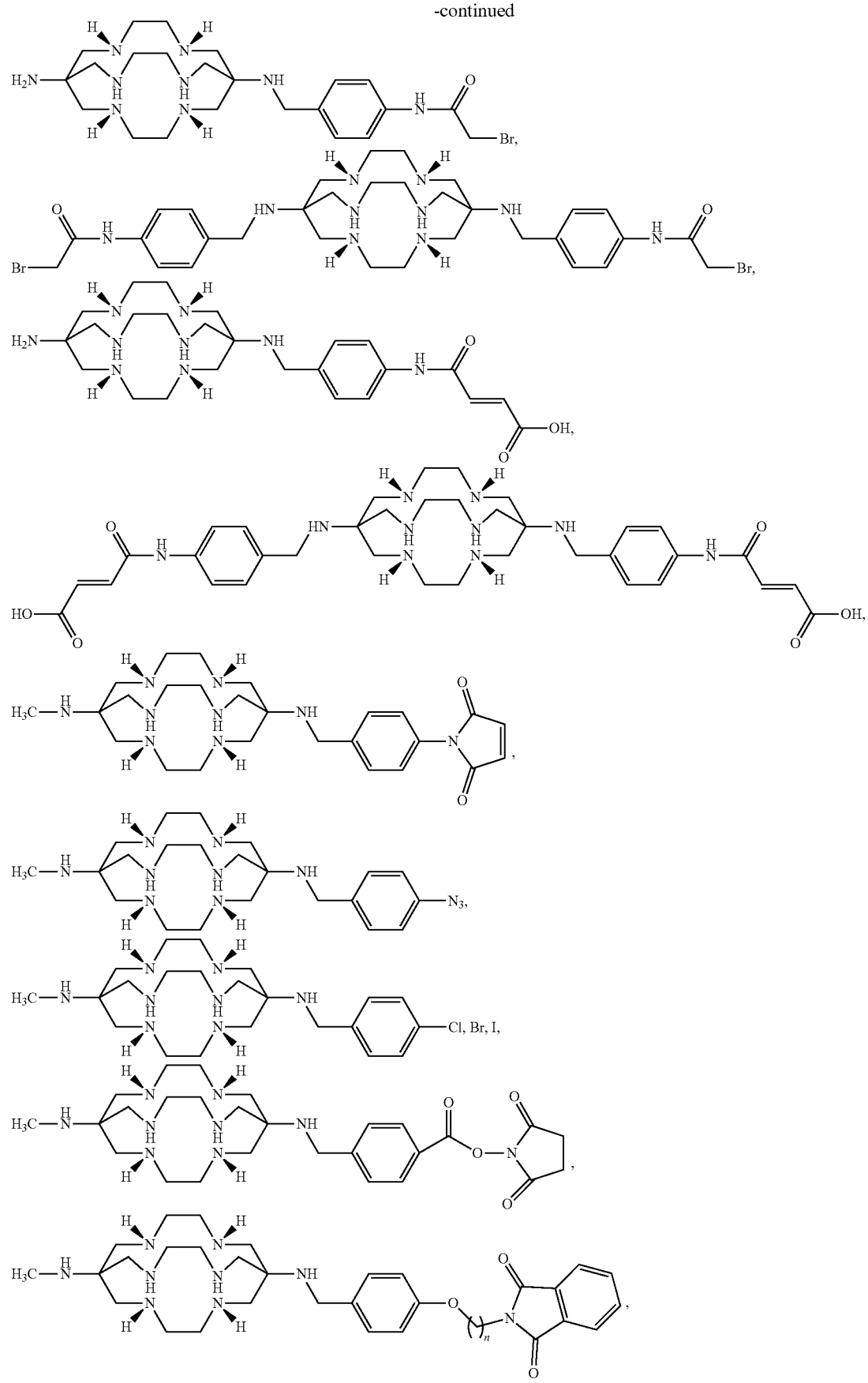

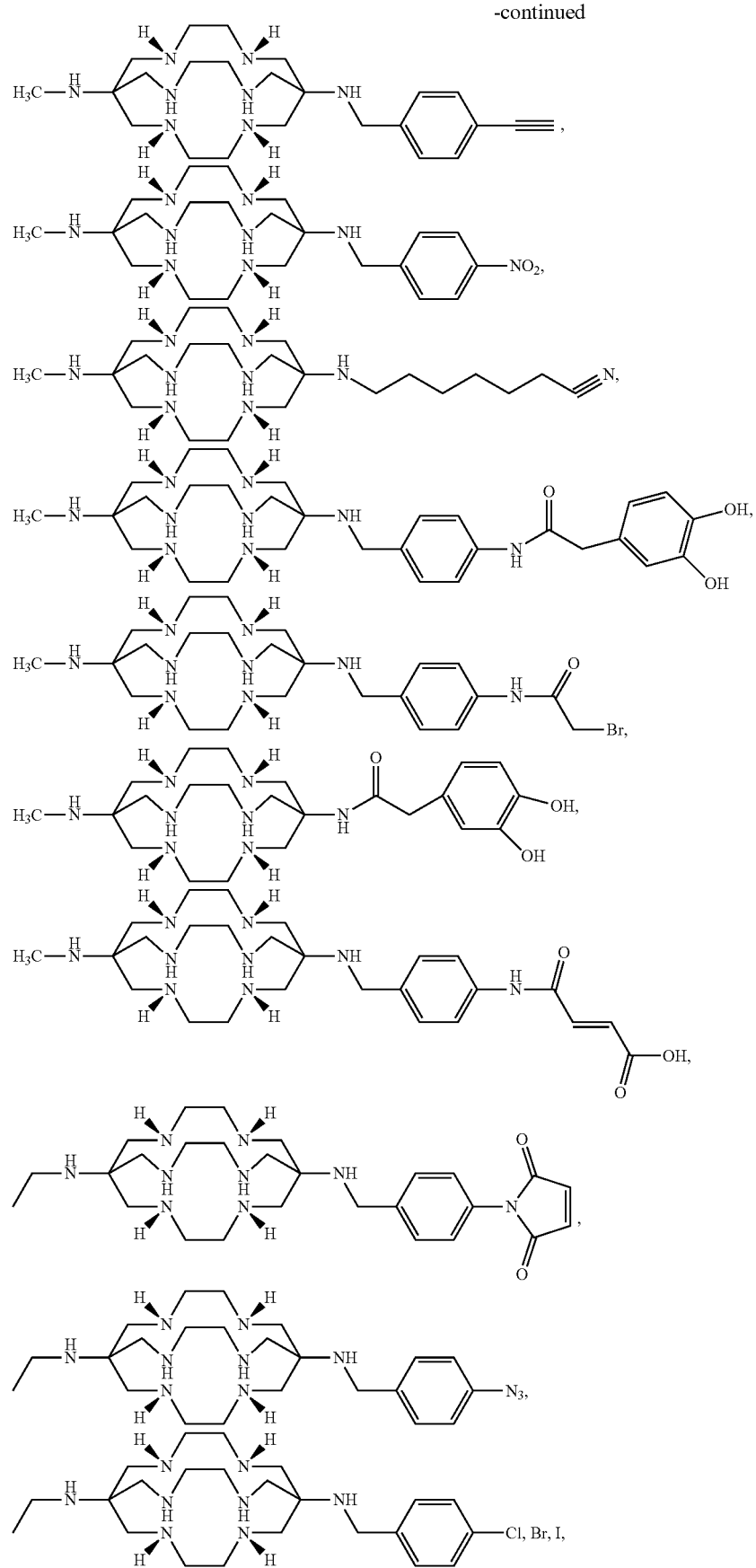

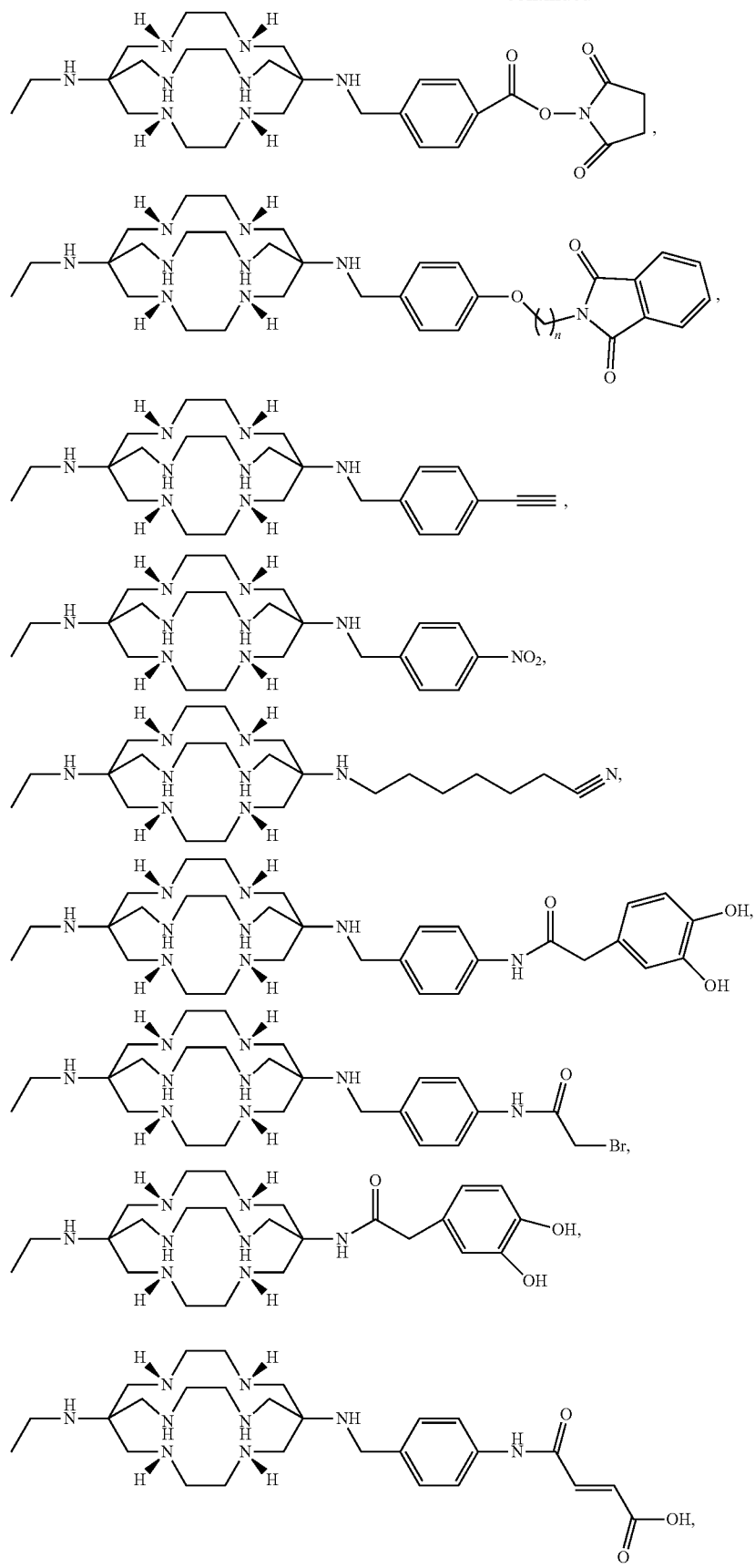

-continued
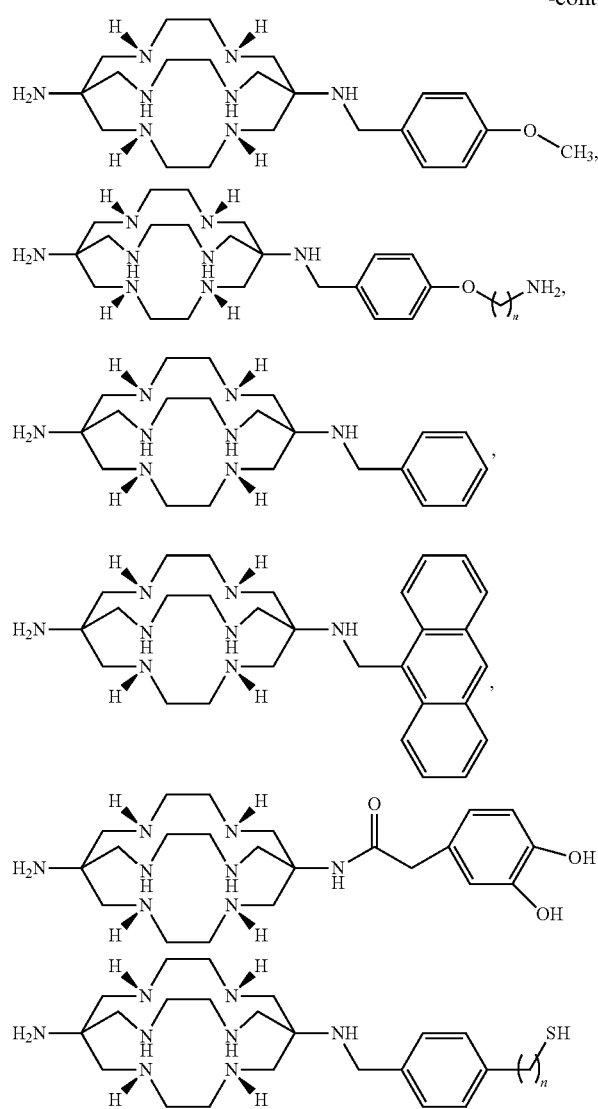
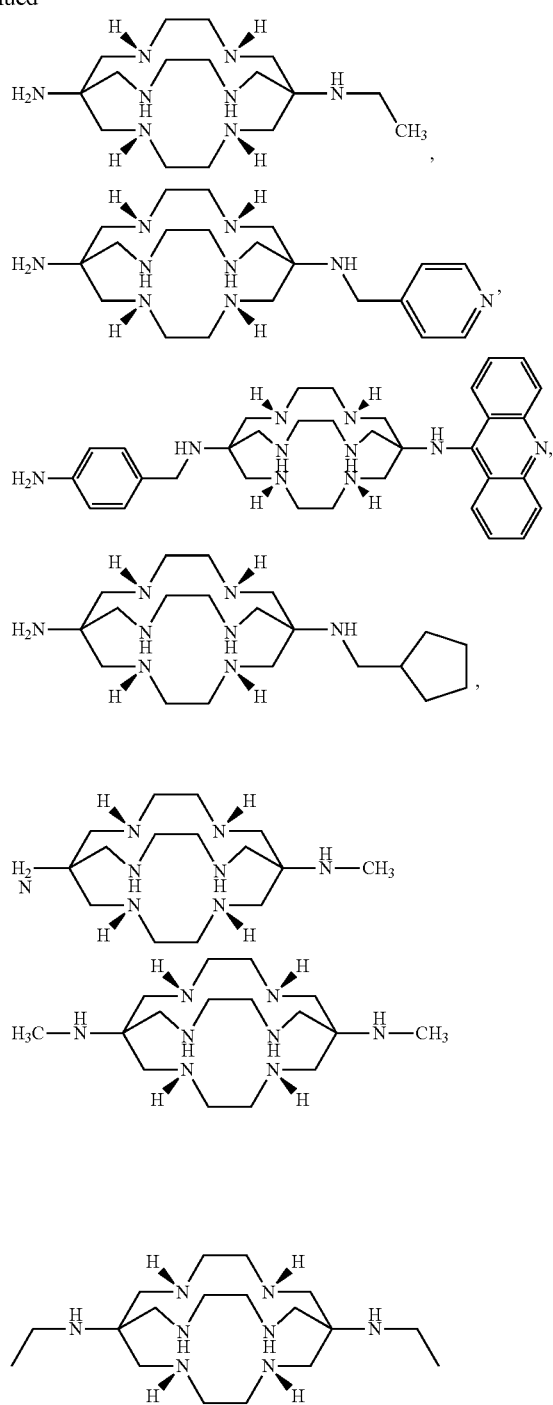
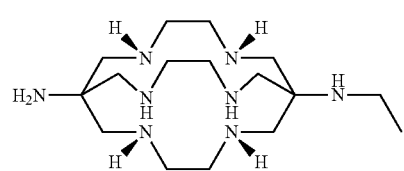
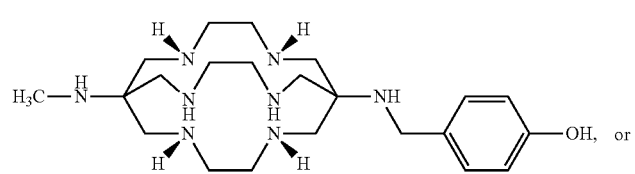

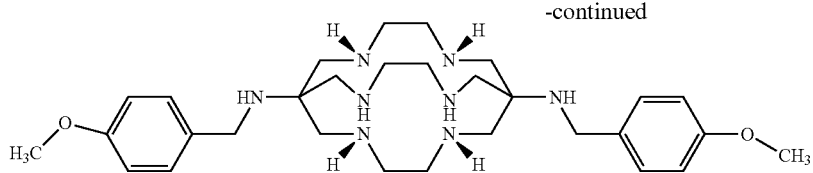

wherein n is an integer of from 1 to 5 (i.e. 1, 2, 3, 4 or 5). Two compounds of particular interest are:

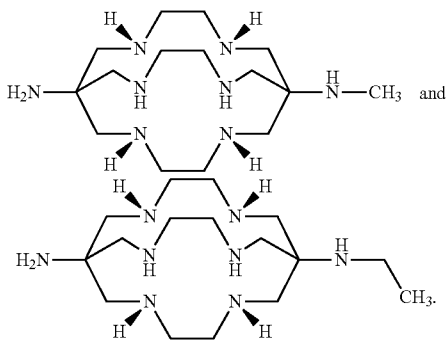

These compounds can be used as the compound of formula (I) in the methods of the present invention to couple with other compounds. The methyl or ethyl group prevents further reaction at the amine (another secondary amine) to which it is bound. Thus, the second compound can only couple with those compounds via the sole primary amine, which results in more of the desired product being obtained.

The synthesis of a number of these compounds will be described in the Examples.

As discussed above, the method of the present invention can be used to produce cryptand- or cryptate-based compounds containing a functional group that would be reduced under reducing conditions. Thus, also provided is a compound having the formula (II):

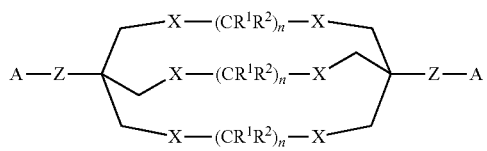

wherein:
each $R^1$ and $R^2$ is independently selected from the group consisting of hydrogen, halogen, $CH_3$, COOH, $NO_2$, $CH_2OH$, $H_2PO_4$, $HSO_3$, CN, C(=O)$NH_2$ and CHO;
n=2, 3 or 4;
each X is independently selected and is NH or S, provided that at least one X is NH;
each Z is an optional spacing group which, when present, is independently selected from the group consisting of an optionally substituted $C_1$-$C_{10}$ alkyl, optionally substituted aryl and optionally substituted heterocycle;
each A is independently selected from the group consisting of hydrogen, halogen, hydroxyl, nitro, optionally substituted amino, optionally substituted alkyl, optionally substituted aryl, optionally substituted aralkyl, optionally substituted heterocycle, isothiocyanate, cyano, —NH—COCH$_2$Br, —COOR', —NHCR$^3$R$^4$R$^5$ and —NH—CO—CH=CH—COOR', provided that at least one A is or contains —NHCR$^3$R$^4$R$^5$;
R' is selected from the group consisting of hydrogen, optionally substituted alkyl and optionally substituted aryl;
$R^3$ and $R^4$ are independently selected from the group consisting of: H, alkyl and aryl; and
$R^5$ is a functional group or a species containing a functional group that would be reduced under reducing conditions.

Compounds having formula (II) contain a functional group that would be reduced under the reducing conditions required by the prior art to remove a templating metal (e.g. Cu(II)) from the coupled cryptate compound, and are therefore not able to be readily produced via prior art processes. This functional group, however, is sufficiently stable under the conditions required to reduce the Schiff base intermediate to the amine group via which the cryptand compound is coupled to $R^5$ (i.e. —NHCR$^3$R$^4$R$^5$). The compounds of formula (II) may contain a functional group that would be reduced in the presence of borohydride or cyanoborohydride.

In some embodiments, $R^5$ is an optionally substituted alkyl, aryl or heterocycle which has a functional group that would be reduced under reducing conditions.

In some embodiments, $R^5$ has the following structure:

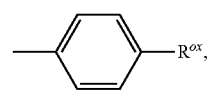

wherein $R^{ox}$ is a functional group that would be reduced under reducing conditions.

In some embodiments, the functional group that would be reduced under reducing conditions is —NO$_2$, —N$_3$, —C≡CH, —C≡N, —O—(CR$^1$R$^2$)$_m$—NH$_2$, —(CR$^1$R$^2$)$_m$—SH, —C(=O)—O—CH$_3$, —C(=O)—O—(CR$^1$R$^2$)$_m$—CH$_3$,

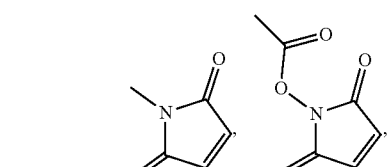

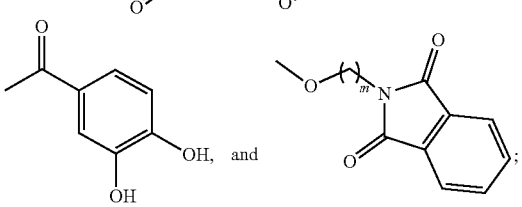

wherein $R^1$ and $R^2$ are as defined above and m is 1 to 8.

In some embodiments, the compound of formula (II) can be conjugated to a carrier agent, such as a molecular recognition unit (as discussed below). It may be coupled via the functional group of $R^5$. In alternative embodiments, the compound of formula (II) may have chemical properties that enable the compound to be localised within specific organs and tissues in a subject following administration of a drug containing the compound to the subject. In some embodiments, the functional group of $R^5$ can provide such chemical properties.

For example, the functional group of $R^5$ may be hydrophobic or may be hydrophilic. Having a hydrophobic entity will encourage clearance of a compound of the present invention that is complexed with a metal ion or metal ion radionuclide through the liver, while a hydrophilic entity will predominantly clear through the kidney. For example the compound Cu-diamsar when administered to balb/s mice is rapidly cleared from the kidneys of the mice, but the compound Cu-sar (which differs from Cu-diamsar in that it lacks the two primary amines on the apical sites of the cryptate cage) is retained for a relatively longer period of time in the kidneys of the balb/s mice.

It stands to reason that modifying the apical sites of the compounds of the present invention will enable the targeting of functional properties of organs such as glomerular filtration of the kidneys, or liver function, or enable the monitoring of enhanced permeability and retention effect (EPR). The latter is the mechanism by which high molecular weight non-targeted drugs and prodrugs accumulate in tissue with increased vascular permeability such as in sites of inflammation and or cancer.

In some embodiments, $R^1$ and $R^2$ in the compound of formula (II) are H.

In some embodiments, each X is NH.

In some embodiments, n is 2.

In some embodiments, $R^1$ and $R^2$ in the compound of formula (II) are H, each X is NH and n is 2.

In embodiments where the compound of formula (II) is formed by a method involving the use of a hydride reducing agent (e.g. a borohydride reducing agent such as sodium cyanoborohydride, sodium borohydride or sodium triacetoxyborohydride), at least one, optionally both, of $R^3$ and $R^4$ is H.

In embodiments where the compound of formula (II) is formed by reacting a cryptand precursor compound with an aldehyde, at least one, optionally both, of $R^3$ and $R^4$ is H.

Also included within the scope of the present invention are prodrugs of the compounds of the present invention. Typically, prodrugs will be functional derivatives of the compounds of the present invention, which are readily converted in vivo to the required compound for the uses described herein. Typical procedures for the selection and preparation of prodrugs are known to those skilled in the art and are described, for instance, in H. Bundgaard (Ed), Design of Prodrugs, Elsevier, 1985.

The phrase "compounds of the present invention" is to be understood to mean the compounds of the second to sixth aspects of the present invention.

Carrier Agents

The compounds of the present invention may be conjugated to a carrier agent to enable them to be carried to a particular location of a subject's body once administered to the subject.

The carrier agent may, for example, be a molecular recognition unit. Molecular recognition units are molecules that recognise a specific antigen or receptor site in the body and, once they have been administered to the subject, can be processed in a predictable manner. For example, some molecular recognition units are capable of binding specifically or preferentially to a tumour or an abnormal cell. Examples of such molecular recognition units comprise one part of specific binding pairs (e.g. antibody/antigen pairs, and the like).

Molecular recognition units include antibodies, proteins, peptides, carbohydrates, nucleic acids, oligonucleotides, oligosaccharides, liposomes, siRNA, RNA, DNA, ssDNA, nucleotides, biomolecular recognition layers, cellular components, dendrimers, polysaccharides, amino acids, enzymes, oligopeptides and steroids. The molecular recognition unit is typically an antibody, protein, peptide, oligonucleotide or oligosaccharide. In particular, the molecular recognition unit is typically an antibody and more typically a monoclonal antibody, its fragments, variable region or nanobody.

In one embodiment, the molecular recognition unit may be a complete antibody or a fragment, variable region or nanobody thereof or an analogue of either of these, provided that the antibody comprises a specific binding region. The antibody may be a humanised monoclonal antibody or a fragment, variable region or nanobody thereof. The antibody may also be a recombinant antibody. The antibody may be specific for any number of antigenic determinants, but is typically specific for one antigenic determinant.

The carrier agent may, for example be a particle or a surface. For example, the carrier agent may be a quantum dot, microparticle, nanoparticle, polymer, micelle, nano gel, micro gel, nanotube or a thin film. Such carrier agents could be used in medical techniques such as electron paramagnetic resonance spectroscopy (EPR) or in drug delivery or stent applications.

In some embodiments, the compounds of the present invention may be conjugated to more than one carrier agent in order to take advantage of the properties of each of the carrier agents. For example, the compounds of the present invention may be conjugated to a nanoparticle and an antibody or peptide. Alternatively, the antibody or peptide may be attached to the particles to assist in the specific targeting.

In some embodiments, the compounds of the present invention may be conjugated to the carrier agent via a linker group (such as an amine, hydroxyl, thiocyanate, isothiocyanate, aldehyde, nitro, maleimide, cyano or azide). The second compound used in the method of the present invention may, for example, include such a linker group. The compound of formula (II) may, for example, be conjugated to a carrier agent via the functional group of $R^5$.

Conjugation of the compounds of the present invention to a carrier agent may, for example, be achieved by reacting the linker group with a thiol, amino, carboxyl, hydroxyl, aldehyde, aromatic or heteroaromatic group present in the carrier agent. For example, a linker group in the form of an amino or hydroxy group may be reacted with a free carboxyl group of the carrier agent. Suitably a coupling agent such as a carbodiimide may be employed to facilitate the conjugation reaction.

The conjugate compounds of the present invention may contain more than one molecule of a compound of the present invention bound to any one carrier agent.

Complexation with a Metal Ion or Metal Ion Radionuclide

The compounds of the present invention may contain a metal ion or a metal ion radionuclide complexed within the cryptand ring system. These compounds may be synthesised by exposing a compound according to the invention which is not complexed with a metal ion to a metal ion so as to complex said compound with the metal ion.

Suitable metal ions or metal ion radionuclides include an ion of Cu, Tc, Ga, In, Co, Re, Fe, Au, Ag, Rh, Pt, Bi, Cr, W, Ni, V, Pb, Ir, Zn, Cd, Mn, Ru, Pd, Hg, Zr, Sc, Rb, Sr and Ti.

The metal ion radionuclides typically comprise metal ions which have at least two oxidation states, most typically an oxidation state of +2, +3, +4 or +5. The radiolabelled metal complex may, for example, contain an ion of $^{48}$V, $^{52}$Fe, $^{52m}$Mn, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{68}$Ga, $^{81}$Rb, $^{83}$Sr, $^{89}$Zr, $^{94m}$Tc, $^{94}$Tc, $^{110}$In, $^{67}$Cu, $^{67}$Ga, $^{111}$In, $^{99m}$Tc, $^{188}$Re, $^{186}$Re, $^{195m}$Pt, $^{191}$Pt and $^{105}$Rh.

Metal complexing of the compounds of the present invention can be accomplished using procedures known in the art. For example, the radiolabelling of compounds of the present invention with $^{64}$Cu can be achieved by adding an aqueous acetate solution of $^{64}$Cu to the compound in an aqueous solution and incubating for less than about 30 minutes at room temperature.

Compounds of the present invention that are conjugated to a carrier agent and complexed with a metal ion or metal ion radionuclide may be prepared either by conjugating a metal complex of a cryptand compound (i.e. a cryptate compound) with a carrier agent or by conjugating the cryptand compound with a carrier agent and then reacting the resultant conjugated compound with a source of the metal ion or metal ion radionuclide.

The present invention thus provides a method for attaching radionuclide metal ions such as $^{48}$V, $^{52}$Fe, $^{52}$Mn, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{68}$Ga, $^{81}$Rb, $^{83}$Sr, $^{89}$Zr, $^{94m}$Tc, $^{94}$Tc, $^{110}$In, $^{67}$Cu, $^{67}$Ga, $^{111}$In, $^{99m}$Tc, $^{188}$Re, $^{186}$Re, $^{195m}$Pt, $^{191}$Pt and $^{105}$Rh and the like to carrier agents such as monoclonal antibodies, receptor specific proteins, peptides or oligonucleotides for in vivo imaging and therapy.

The compounds of the present invention may also be radiolabelled by causing them to contain a non-metal gamma or beta emitting radionuclide (e.g. $^{3}$H or $^{131}$I). Such radiolabelled compounds can be prepared using techniques known in the art.

Non-radionuclide metal ions can be complexed with the compounds of the present invention and subsequently used for diagnosis, imaging or therapy of a disease. For example, compounds of the present invention in which an ion of Mn or Fe is complexed may be useful as MRI agents.

The compounds of the present invention may be provided in the form of a kit comprising a first container that contains a metal ion (optionally a metal ion radionuclide), usually in solution, and a second container that contains an uncomplexed compound of the present invention. The kit could be supplied to radio-chemists, technicians, radiopharmacists, doctors or the like for them to mix the contents of the first and second containers to thereby obtain the complexed compound immediately prior to use.

Pharmaceutical Compositions

The present invention also relates to pharmaceutical compositions comprising the compounds of the present invention, or a pharmaceutically acceptable salt thereof.

A pharmaceutical composition of the present invention comprises a compound of the present invention, or a pharmaceutically acceptable salt thereof, and a pharmaceutically acceptable carrier. Pharmaceutically acceptable salts are those salts which are suitable for use in contact with the tissues of humans and other animals without undue toxicity, irritation, allergic response and the like, and are commensurate with a reasonable benefit/risk ratio. Pharmaceutically acceptable salts are well known in the art.

Suitable pharmaceutically acceptable salts of the compounds of the present invention may be prepared by mixing the compounds of the present invention with a pharmaceutically acceptable acid such as hydrochloric acid, sulphuric acid, methanesulphonic acid, succinic acid, fumaric acid, maleic acid, benzoic acid, phosphoric acid, acetic acid, oxalic acid, carbonic acid, tartaric acid, or citric acid. Suitable pharmaceutically acceptable salts of the compounds of the present invention therefore include acid addition salts.

The compounds of the present invention may be converted to pharmaceutically acceptable salts by way of recognised procedures. For example, S. M. Berge el al. describe pharmaceutically acceptable salts in detail in *J. Pharmaceutical Sciences*, 1977, 66:1-19. The salts can be prepared in situ during the final isolation and purification of the compounds of the invention, or separately by reacting the free base function with a suitable organic acid. Representative acid addition salts further include acetate, adipate, alginate, ascorbate, asparate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

It will be appreciated that other salts (i.e. non-pharmaceutically acceptable salts) could be used if the compounds of the present invention were not being used in a medical application.

When used for the treatment or radioimaging of a disease, the compounds of the present invention, or a pharmaceutically acceptable salt thereof, may be administered alone. However, it is generally preferable that they be administered as pharmaceutical formulations including the compound and a pharmaceutically acceptable carrier or carriers. In general pharmaceutical formulations of the present invention may be prepared according to methods which are known to those of ordinary skill in the art and accordingly may include a pharmaceutically acceptable carrier, diluent and/or adjuvant.

The pharmaceutical formulations typically comprise a formulation in the form of a suspension, solution or other suitable formulation. Physiologically acceptable suspending media together with or without adjuvants may be used. The pharmaceutical formulations are typically in a liquid form and still more typically are in an injectable form. Still more typically, the injectable formulations are dissolved in suitable physiologically acceptable carriers which are recognised in the art.

The carriers, diluents and adjuvants must be "acceptable" in terms of being compatible with the other ingredients of the formulation, and not deleterious to the recipient thereof.

Examples of pharmaceutically and veterinarily acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

For administration as an injectable solution or suspension, non-toxic parenterally acceptable diluents or carriers can include, Ringer's solution, isotonic saline, phosphate buffered saline, ethanol and 1,2-propylene glycol.

Adjuvants typically include emollients, emulsifiers, thickening agents, preservatives, bactericides and buffering agents.

Methods for preparing parenterally administrable compositions are apparent to those skilled in the art, and are described in more detail in, for example, Remington's Pharmaceutical Science, 15th ed., Mack Publishing Company, Easton, Pa.

These formulations can be administered by standard routes, for example, by topical, transdermal, intraperitoneal, intracranial, intracerebroventricular, intracerebral, intravaginal, intrauterine, oral, rectal or parenteral (e.g. intravenous, intraspinal, subcutaneous or intramuscular) routes.

In specific embodiments, the compounds of the present invention, or a pharmaceutically acceptable salt thereof, can be incorporated into biodegradable polymers to allow for sustained release, the polymers being implanted in the vicinity of where drug delivery is desired (e.g. at the site of a tumour) or implanted so that the active agents are slowly released systemically. Osmotic minipumps may also be used to provide controlled delivery of high concentrations of the active agents through cannulae to the site of interest such as directly into, for example, a metastatic growth or into the vascular supply to that tumour.

Methods of Diagnosis, Imaging and Therapy

Compounds of the present invention, or pharmaceutically acceptable salts thereof, may be used in methods of diagnosis, methods of imaging and methods of therapy of diseases such as cardiovascular disease, neurological disease, autoimmune disease, infectious disease and oncology. Specific conditions include rheumatoid arthritis, multiple sclerosis, psoriasis, respiratory syncytical virus infection, lung cancer, lymphoma, colorectal cancer, breast cancer, liver cancer, neuroblastoma, prostate cancer, bladder cancer and cervical cancer and ovarian cancer.

The present invention provides methods for diagnosing a disease, methods for radioimaging, or methods for radiotherapy of a disease in a subject, comprising administering to the subject an effective amount of a radiolabelled compound of the present invention, or a pharmaceutically acceptable salt thereof, or a pharmaceutical composition of the present invention.

The present invention also provides methods for diagnosing a disease, methods for imaging, or methods for therapy of a disease in a subject, comprising administering to the subject an effective amount of a compound of the present invention, or a pharmaceutically acceptable salt thereof, or a pharmaceutical composition of the present invention.

Typically, the compounds of the present invention administered to a subject comprise a coupled cryptand or cryptate compound conjugated to a molecular recognition unit (e.g. monoclonal antibodies, or its fragments, variable regions or nano-bodies, peptides, oligonucleotides, oligosaccharides liposomes, or a part of a specific binding pair). Such conjugated molecules are known to localise with great specificity in certain organs and tissues in a subject after administration. However, as discussed above, compounds of the present invention that are not conjugated to a carrier agent may localise in certain organs or tissues in a subject after administration. For example, compounds of the present invention in which the cryptand or cryptate compound is coupled with an intercalating species may have an affinity to DNA. Such compounds could also be conjugated with a molecular recognition unit that would enable the compound to enter the cell nucleus of a patient in order to intercalate DNA in vivo.

In some embodiments, the methods of therapy of the present invention involve using compounds of the invention which are useful as cytotoxic agents. For example, a radiolabelled compound of the present invention may be used for the treatment of cancer, abnormal cell disorders and the treatment of tumours. In such applications, the radiolabelled compound may be conjugated to a carrier agent to enable it to bind selectively to the tumour or abnormal cell.

The method of therapy will typically involve the administration of an effective amount of a radiolabelled compound of the present invention to a subject. The effective amount or dosage will depend upon the desired amount of radioactivity required for the diagnostic application, balanced with the safety requirement of not exposing the subject, in particular their organs and tissues, to harmful amounts of radiation. Appropriate dosages for any given application may be determined by persons skilled in the relevant art.

Typically the treatment would be for the duration of the condition, and contact times would typically be for the duration of the condition. Further, it will be apparent to one of ordinary skill in the art that the optimal quantity and spacing of individual dosages will be determined by the nature and extent of the condition being treated, the form, route and site of administration, and the nature of the particular condition being treated. It will also be apparent to one of ordinary skill in the art that the optimal course of treatment, such as, the number of doses given per day for a defined number of days, can be ascertained by those skilled in the art using conventional course of treatment determination tests.

When used for the treatment of disease, the compound of the present invention may be administered alone. However, the compound may also be administered in conjunction with other chemotherapeutic treatments conventionally administered to patients for treating the disease. For example, a tumour may be treated conventionally with surgery, and the compound of the present invention administered in order to extend the dormancy of micrometastases and to stabilise and inhibit the growth of any residual primary tumour.

Typically, when used in the treatment of solid tumours, compounds of the present invention may be administered with chemotherapeutic agents such as: adriamycin, taxol, fluorouricil, melphalan, cisplatin, alpha interferon, COMP (cyclophosphamide, vincristine, methotrexate and prednisone), etoposide, mBACOD (methortrexate, bleomycin, doxorubicin, cyclophosphamide, vincristine and dexamethasone), PROMACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide; nitrosoureas including carmustine, lomustine, semustine and streptozocin; alkyl sulfonates including busulfan; triazines including dacarbazine; ethyenimines including thiotepa and hexamethylmelamine; folic acid analogues including methotrexate; pyrimidine analogues including 5-fluorouracil, cytosine arabinoside; purine analogues including 6-mercaptopurine and 6-thioguanine; antitumour antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar.

Compounds of the present invention that are radiolabelled and conjugated to molecular recognition units (especially radiolabelled antibodies) are particularly useful in medicine, for example, in locating specific tissue types and in the therapy of cell disorders. Radiolabelled antibodies can also be used to target metal ions to a specific tissue type, both in vitro and in vivo. Exemplary uses for the compounds of the present invention in therapy will be described below.

Such compounds can, for example, be used to radiolabel monoclonal antibodies specific for colon, ovarian, lymphoma, breast and/or bladder cancer or apoptosis. Another exemplary use is in the radiolabelling of a monoclonal antibody specific for metastasis of colon cancer for diagnosis and therapy.

Compounds of the present invention that are conjugated to a molecular recognition unit in the form of a monoclonal antibody and radiolabelled with $^{67}$Cu (beta and gamma emitter) and $^{64}$Cu (positron and beta emitter) can be used for combined radioimmunoscintography (RIS) (SPECT and PET) and radioimmunotherapy (RIT).

Compounds of the present invention that are coupled with an intercalator, conjugated to a monoclonal antibody and radiolabelled with auger emitting isotopes such as $^{59}$Fe, $^{195m}$Pt or $^{64}$Cu can be delivered to the cell nucleus, where the auger emission can be used to break the DNA.

The present invention also relates to the use of compounds of the present invention as imaging agents in vitro and in vivo. The imaging may, for example, be radioimaging techniques such as positron emission tomography (PET), single-photon emission computed tomography (SPECT) or fluorescence imaging, or imaging techniques not necessarily requiring radioisotopes, such as magnetic resonance imaging (MRI) or fluorescence imaging. Thus, the compounds of the present invention may also be used as MRI agents, PET agents, SPECT agents or fluorescence imaging agents.

For example, in MRI applications, the compound of the present invention is provided with a paramagnetic metal ion (typically Fe (III) or Mn(II)) and may be used as a contrast agent to enhance images. Furthermore, such compounds may be provided in the form of a pharmaceutical formulation, where the compound of the present invention, or a pharmaceutically acceptable salt thereof, is present with a pharmaceutically acceptable carrier, excipient or vehicle.

These imaging agents will localise in specific organs and tissues in a subject following administration. This localised concentration can subsequently be detected. In some embodiments, the imaging agent may simply be a compound of the present invention which has chemical properties that cause it to localise is a specific organ or tissue in a subject. In alternative embodiments, the imaging agent may be a compound of the present invention that is conjugated to a carrier agent.

The methods of diagnosis will typically involve the administration of an effective amount of a compound of the present invention, or a pharmaceutically acceptable salt thereof, to a subject, followed by monitoring the subject after a suitable period of time in order to ascertain whether the compound has localised in a particular area. For example, the method can be used to detect the presence or absence of a cancer, as evidenced by localisation of a radiolabelled complex at a particular site in the subject. Typically, the monitoring step provides information regarding the location of any cancer if it is present. The effective amount or dosage of the radiolabelled complex will depend upon the desired amount of radioactivity required for the diagnostic application, balanced with the safety requirement of not exposing the subject, in particular their organs and tissues, to harmful amounts of radiation. Appropriate dosages for any given application may be determined by persons skilled in the relevant art.

For example, in one embodiment, the radioimaging is fluorescence imaging and the imaging compound is:

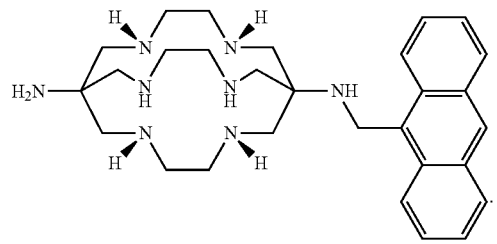

Incorporation of a metal ion into the cryptand ligand may enable a bi-modal system where the fluorescent properties and properties of the metal ion (e.g. radioactivity or unpaired electrons) are both utilised in imaging, diagnosis or treatment.

Compounds of the present invention may also be useful as biomarkers. Biomarkers have been designed for use in cardiovascular diseases, neurology, autoimmune diseases, infectious diseases and oncology. Biomarkers can be used to predict a patient's response to specific therapy, to enable the early detection or screening of a marker, to assess the response to disease during treatment and the likelihood of outcome (regardless of therapeutic), or predict the clinical benefit or lack thereof.

Biomarkers can be used to streamline decision during drug discovery-development process and could reduce attrition of drugs. They can be used during the following stages of drug development:
  Screening of compounds
  Target discovery
  Understanding mechanism of action
  Toxicity safety and safety evaluation
  Incorporation into preclinical and clinical screening
  Follow up on drug effects routinely.

The compounds of the present invention also have application in other fields. For example, they can be attached to solid surfaces, such as polymers, and used for the concentration of metal ions or purification of water. Alternatively, they can be attached to an electrode surface and used for the detection of specific metal ions.

As will be appreciated from the description set out above, the present invention relates to the production of sarcophagines or cryptand/cryptate-type compounds for diagnosis, prognosis and therapy of disease. The cryptand/cryptate compounds can be conjugated to a range of carrier agents such as molecular recognition units and/or radiolabelled with a suitable radioisotope to form a radiopharmaceutical. The synthesis of these functionalised cryptand/cryptates is via a new method which is more cost effective and higher yielding. The method also enables the synthesis of a new range of cryptand- and cryptate-type compounds not previously prepared. The methods of treatment and/or diagnosis described above may be applied to human subjects. They may be applied to non-human subjects, e.g. non-human mammals, non-human vertebrates etc.

Other advantages of at least preferred embodiments of the invention include:
- An identifiable reduction in cost in consumables, time and equipment for the production of sarcophagines (the time required to produce 100 g of desired sarcophagine derivative may be improved by ~40%, and the cost reduced by >30%).
- No protective groups are required for the synthesis so the yields of final products are maximised.
- Synthesis can be controlled to produce mainly mono-substituted species and therefore the precursor cages can be recycled for reuse.

Definitions of Chemical Terms

The optional substituents referred to herein may be selected from the group consisting of amino, halogen, hydroxy, mercapto, nitro, cyano, thiocyano, alkyl, alkoxy, halogenoalkyl, acyl, acylamino, acyloxy, carboxyl, alkoxycarboxyl, carbamoyl, pyridoylamino, carboxyalkyl-carbamoyl, N-carboxylalkylcarbamoyl, sulfo, sulfamoyl, mono- or di-alkylated or phenylated sulfamoyl optionally having one or more alkyl substituents, alkylsulfonyl, alkoxysulfonyl, optionally hydroxyl-containing phenylsulfonyl and phenoxy sulfonyl.

The term "alkyl" refers to linear or branched alkyl groups or cyclic alkyl groups, comprising between 1 and 20 carbon atoms (preferably between 1 and 7 carbon atoms). Examples of linear alkyl groups include methyl, propyl or decyl, and examples of branched alkyl groups include iso-butyl, tert-butyl or 3-methyl-hexyl. Examples of cyclic alkyl groups include cyclohexyl and fused alkyl cyclic ring systems.

The term "aryl" or "aryl group" refers to any aromatic substituent. The aromatic substituent preferably contains from 1 aromatic ring, up to 4 fused aromatic rings, and between 5 and 50 ring atoms. Aromatic groups are cyclically conjugated molecular entities, containing 4n+2 delocalised n electrons, where n=0 or a positive integer (Hickel 4n+2-rule). Any aromatic groups conforming to this rule are within the definition of aryl. The aryl group may be carbocyclic (i.e. contain carbon and hydrogen only) or may be heteroaromatic (i.e. contain carbon, hydrogen, and at least one heteroatom). The aryl group may be monocyclic such as a phenyl, or a polycyclic aryl group such as naphthyl or anthryl. Examples of aryl groups include a phenyl group, biphenyl group, terphenyl group, naphthyl group, anthryl group, pyrenyl group, etc. The term "aryl" is also used to describe an aromatic ring with any degree of substitution.

The term "aralkyl" refers to alkyl groups substituted with one or more aryl groups. Examples of such groups are benzyl, 2-phenylethyl and 1-phenylethyl.

The term "heterocycle", "heterocyclic" or "heterocyclic group" refers to any cyclic groups having between one and five rings, and between 3 to 50 (preferably 5 to 7) ring atoms, of which at least one atom is a heteroatom. The heteroatoms may be selected from one or more of O, N, S, Si and P. In certain embodiments, the heterocyclic group is a 5-membered, 6-membered or 7-membered heterocyclic group (a single-ring heterocyclic group). One subclass of heterocyclic groups are the heteroaromatic (or heteroaryl) groups, which are aromatic groups containing one or more heteroatoms selected from one or more of O, N and S. Such heteroaromatic groups also fall within the definition of aryl group. Some specific examples of "heterocyclic groups", "heteroaromatic groups", or "heteroaryl groups" include moieties of imidazole, benzimidazole, pyrrole, furan, thiophene, benzothiophene, oxadiazoline, indoline, carbazole, pyridine, quinoline, isoquinoline, benzoquinone, pyrazoline, imidazolidine, piperidine, etc.

The term "cyclic" is used in its broadest sense to refer to cyclic groups and linked or fused ring systems having between 3 and 50 ring atoms, which may be carbocyclic (containing carbon ring-atoms only) or heterocyclic (containing carbon atoms and at least one heteroatom), and may be saturated or unsaturated. The number of rings is suitably between 1 and 5, preferably 1 or 2 and, if more than one ring is present, any two may be linked or may be fused or may be coupled through a separate group.

The term "cryptand" refers to a molecular entity comprising a cyclic or polycyclic assembly of binding sites that contains three or more binding sites held together by covalent bonds, and which defines a molecular cavity in such a way as to bind (and thus "hide" in the cavity) another molecular entity, the guest (a cation, an anion or a neutral species), more strongly than do the separate parts of the assembly (at the same total concentration of binding sites). The adduct thus formed is called a "cryptate" (http://www-.chemicool.com/definition/cryptand.html). A representative cryptand group used in the present invention is:

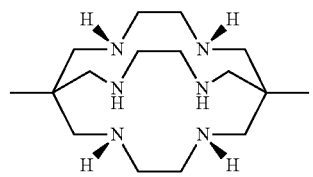

and a corresponding cryptate group is:

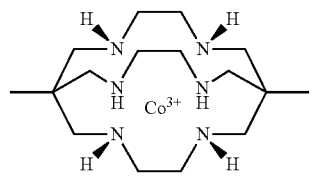

The term amide refers to substituents containing the group —C(O)NRR', wherein R and R' are selected from H, alkyl, aryl or alkyl-aryl groups, which have been defined previously. The term "imide" refers to substituents containing the group —C(O)NRC(O)R', wherein R and R' are selected from H, alkyl, aryl or alkyl-aryl groups. The term "imine" refers to substituents containing the group —C(=NR)R', wherein R and R' are selected from H, alkyl, aryl or alkyl-aryl groups. The term "amidine" refers to substituents containing the group —C(=NR)NR'R", wherein R, R' and R" are selected from H, alkyl, aryl or alkyl-aryl groups.

The term "amine" refers to the amino group —NH$_2$, and also to secondary and tertiary alkylamino, arylamino and alkylarylamino groups. Examples of an "arylamino group" include a diphenylamino group, ditolylamino group, isopropyldiphenylamino group, t-butyldiphenylamino group, diisopropyldiphenylamino group, di-t-butyl diphenylamino group, dinaphthylamino group, naphthylphenylamino group, etc. Examples of an "alkylamino group" include dimethylamino group, diethylamino group, dihexylamino group, etc.

"Nitro" refers to —NO$_2$. "Cyano" refers to —C≡N. "Hydroxy" refers to —OH. "Halogen" or "halo" refers to fluorine, chlorine, bromine and iodine.

"Ether" refers to groups containing an ether group R—O—R', wherein R and R' are selected from H, alkyl, aryl or alkyl-aryl groups, which have been defined previously.

"Carbonyl group" refers to substituents containing a carbonyl group C=O. Such groups include ketones (—C(O)R), aldehydes (—CHO), enones (—C(O)—CR'=CR'R"), acyl halides (—C(O)-halogen), carbonates (R—O—C(=O)—O—R') and acid anhydrides (—C(O)—O—C(O)—R') as examples, where each of R, R' and R" is an alkyl or aryl group. Other examples include esters (—CO$_2$R), carboxylic acids (—CO$_2$H) and amides (—CONRR'). Also, as will be understood by a person skilled in the art, the term "carbonyl group" will also encompass functional equivalents of carbonyl containing functional groups which include, but are not limited to acetals and thioketones.

"Carboxyl" refers to substituents containing a carboxylate group (RCO$_2$), where R is alkyl or aryl, as examples. "Carbamate" refers to substituents containing a carbamate group —O—C(=O)—NRR', where R and R are typically alkyl or aryl, or may together form a ring.

"Sulphide" refers to —SR where R is H, alkyl or aryl, as an example. "Sulpho" refers to groups containing the unit —S(=O)$_2$—, such as —S(=O)$_2$—R where R is alkyl or aryl, as examples. "Sulphoxide" refers to groups containing the unit —S(=O)—, such as —S(=O)—R where R is alkyl or aryl, as examples.

EXAMPLES

Example 1—Synthesis of Sarar-NO$_2$ and Sar(Ar—NO$_2$)$_2$

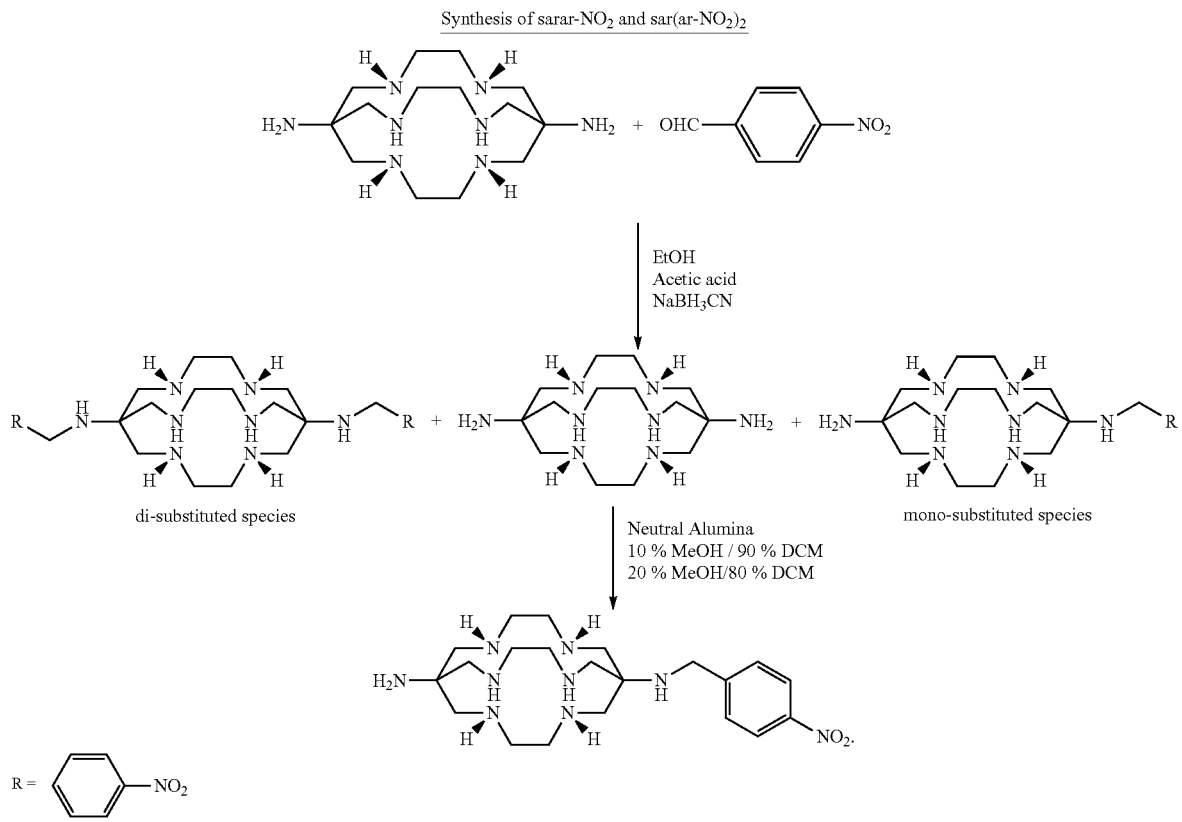

This scheme summarizes synthesis of sarar-NO$_2$ [1-N-(4-nitrobenzyl)-3,6,10,13,16,19-hexaazabicyclo[6.6.6]eicosane-1,8-diamine] and sar(ar-NO$_2$)$_2$ [1,13-N,N-bis-(4-nitrobenzyl)-3,6,10,13,16,19-hexaazabicyclo[6.6.6]eicosane-1,8-diamine].

Diamsar (200 mg) was dissolved in ethanol (10 mL) and the pH adjusted to 4.5 using acetic acid (note: hydrochloric acid cannot be used in place of acetic acid because it causes the diamsar to precipitate from solution). To this solution was added a mixture of p-aminobenzaldehyde (100 mg) in ethanol (10 mL) drop wise over 15 minutes at room temperature. The resulting solution was left to stir for one hour. After this time a solution of sodium cyanoborohydride (40 mg) in ethanol (10 mL) was added drop wise over 15 minutes. The resulting solution was left to stir for 18 hours, before the solvent was removed on a rotary evaporator with a 30° C. water bath. This was followed by high vacuum for one hour. The residue was then extracted with acetonitrile (2×10 mL) and filtered through a 0.45 μm filter. The solvent was again removed by a rotary evaporator with a 30° C. water bath, followed by high vacuum for one hour. The residue was again extracted with acetonitrile and a spoon full of neutral alumina was added before the solvent was again removed by a rotary evaporator with a 30° C. water bath followed by high vacuum for two hours. The dried alumina was then place on top of a 25 cm neutral alumina column. Using a mobile phase of 10% methanol 90% dichloromethane (300 mL) followed by 20% methanol 80% dichloromethane removed band one as SarAr—(NO$_2$)$_2$ with band 2 being the desired product of SarAr-NO$_2$ 95 mg (34%) and band 3 being unreacted diamsar.

SarAr-NO$_2$ $^1$H NMR (D$_2$O): 3.00 (s, 12H, NCH$_2$CH$_2$N); 3.10 (s, 6H, NCCH$_2$N); 3.20 (s, 6H, NCCH$_2$NCCH$_2$); 3.90 (s, 2H, ArCH$_2$); 7.60-7.57 (d, 2H, Ar—H); 8.30-8.20 (d, 2H, Ar—H). $^{13}$C NMR (D$_2$O): δ 147.0, 146.8, 129.3, 123.8, 57.5, 54.9, 54.7, 50.8, 47.9, 44.7. Mass Spec: ESI/MS, m/z=450 [M+H]$^+$.

SarAr—(NO$_2$)$_2$ $^1$H NMR (D$_2$O): 3.00 (s, 12H, NCH$_2$CH$_2$N); 3.20 (s, 6H, NCCH$_2$N); 3.20 (s, 6H, NCCH$_2$NCCH$_2$); 3.90 (s, 4H, ArCH$_2$); 7.60-7.50 (d, 4H, Ar—H); 8.30-8.20 (d, 4H, Ar—H). Mass Spec: ESI/MS, m/z=585[M+H]$^+$.

Example 2—Synthesis of Sarar-Maleimide and Sarar-(Maleimide)$_2$

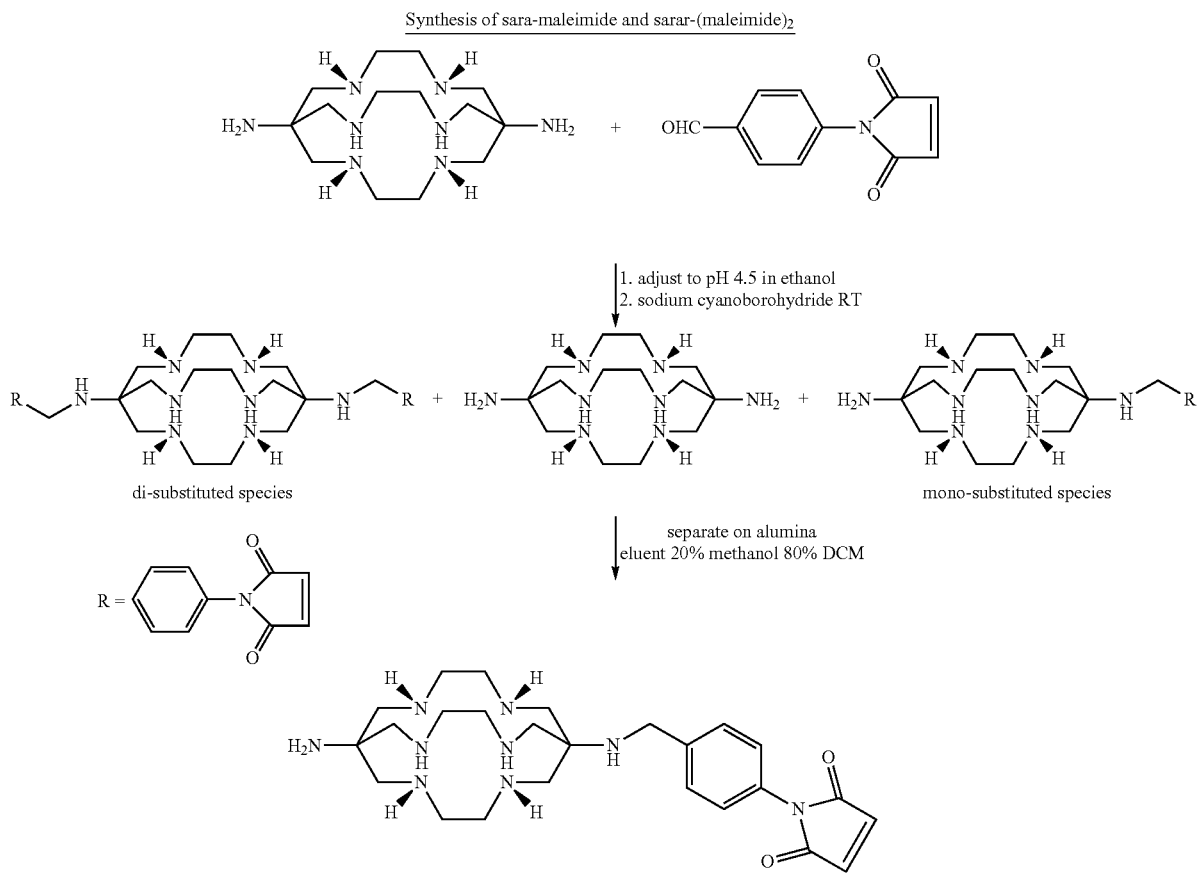

This scheme summarizes the synthesis of sarar-maleimide [1-N-(benzyl-maleimide)-3,6,10,13,16,19-hexaazabicyclo[6.6.6]eicosane-1,8-diamine] and sarar-(maleimide)$_2$ [1,13-N,N-bis(benzyl-maleimide)-3,6,10,13,16,19-hexaazabicyclo[6.6.6]eicosane-1,8-diamine].

SarAr-Maleimide and SarAr-(Maleimide)$_2$ were produced by adding a diamsar (200 mg) to ethanol 10 mL and then adjusting the pH to 4.5 using acetic acid (note: hydrochloric acid can not be used in place of acetic acid because it causes the diamsar to precipitate from solution). To this solution is added a mixture of p-maleimidobenzaldehyde (120 mg) in 10 mL ethanol drop wise over 15 minutes. This solution is left to stir for one hour. After this time a solution of sodium cyanoborohydride (40 mg) in ethanol 10 mL is added drop wise over 15 minutes. This solution is left to stir for 18 hours before removing the solvent on a rotary evaporator with a 30° C. water bath followed by high vacuum for one hour. The residue was extracted with acetonitrile (2×10 mL) and filtered through a 0.45 m filter. The solvent was again removed by a rotary evaporator with a 30° C. water bath followed by high vacuum for one hour. The residue was again extracted with acetonitrile and a spoon full of neutral alumina added before again removing the solvent by a rotary evaporator with a 30° C. water bath followed by high vacuum for two hours. The dried alumina was then place on top of a 25 cm neutral alumina column. Using a mobile phase of 10% methanol 90% dichloromethane (300 mL) followed by 20% methanol 80% dichloromethane removed both SarAr-Maleimide and SarAr-(Maleimide)$_2$ as a mixture.

SarAr-Maleimide $^1$H NMR (D$_2$O): 2.90 (s, 12H, NCH$_2$CH$_2$N); 3.30 (s, 6H, NCCH$_2$N); 3.40 (s, 6H, NCCH$_2$NCCH$_2$); 4.10 (s, 2H, ArCH$_2$); 7.10 (s, 2H, —HC=CH—); 7.40-7.30 (d, 2H, Ar—H); 7.60-7.50 (d, 2H, Ar—H). Mass Spec: ESI/MS, m/z=500[M+H]$^+$. SarAr-(Maleimide)$_2$ $^1$H NMR (D$_2$O): 2.90 (s, 12H, NCH$_2$CH$_2$N); 3.40 (s, 12H, NCCH$_2$N); 4.10 (s, 4H, ArCH$_2$); 7.10 (s, 4H, —HC=CH—); 7.40-7.30 (d, 4H, Ar—H); 7.60-7.50 (d, 4H, Ar—H). Mass Spec: ESI/MS, m/z=685[M+H]$^+$.

Example 3—Synthesis of Sarar-Oxy-Proplyamine

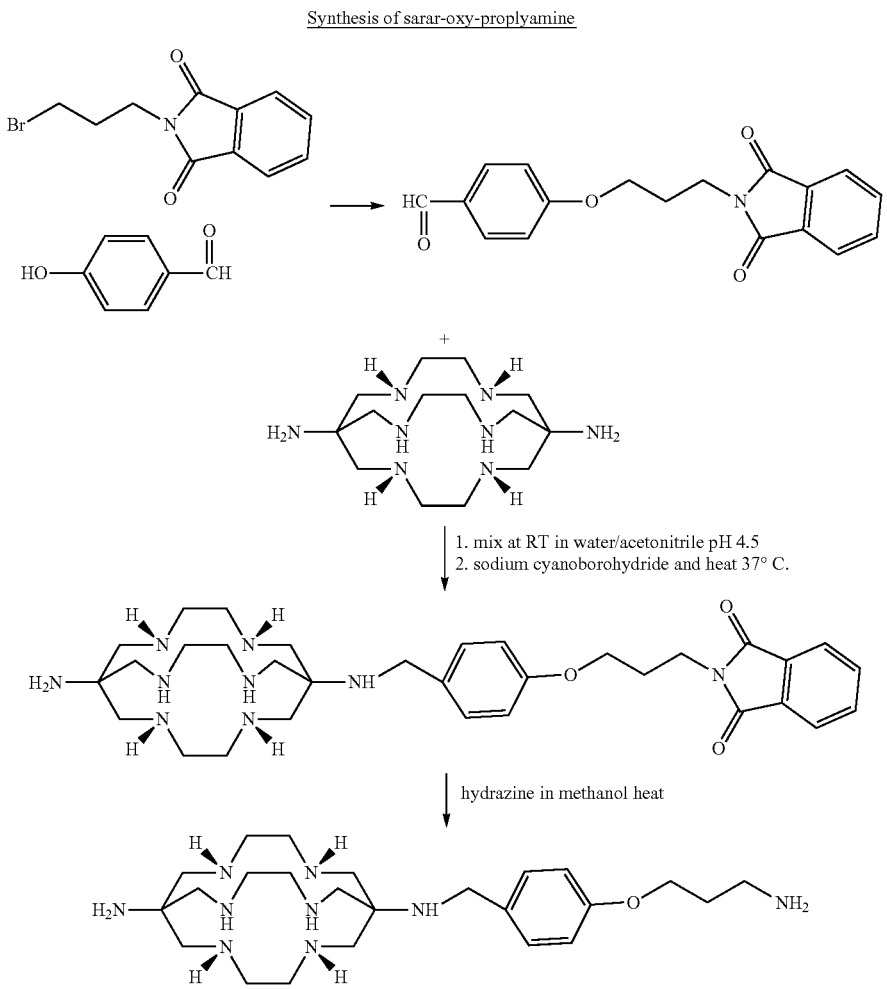

This scheme summarizes the synthesis of sarar-oxy-proplyamine [1N-(oxyproplyamine)-3,6,10,13,16,19-hexaazabicyclo[6.6.6]eicosane-1,8-diamine].

Diamsar (156 mg) was dissolved in 6 mL water and the pH was adjusted to 4.0 using 5 M HCl (~286 μL). To this solution was added 154 mg 4-(3-(1,3-dioxoisoindolin-2-yl)proproxy)benzaldehyde in 10 mL THF. This solution was left to stir for 2 mins. after which time a solution of sodium cyanoborohydride (312 mg) in water 1 mL was added.

The resulting solution was left to stir for 1 hour at 37° C., before the solvent was removed on a rotary evaporator with a 30° C. water bath. The residue was taken up with 50 mL water and extracted with dichloromethane (4×20 mL). The organic phase was evaporated. 30 mL of acetonitrile was added to the residue and heated at 60° C. for 10 mins. The acetonitrile solution was filtered through a 0.22 m filter unit. The acetonitrile solutions that contained the desired product were evaporated. The phthalimide-containing product was purified by reverse-phase HPLC using a water:methanol gradient [10 mins 100% water, 0.1% formic acid; followed 40% methanol, 0.1% formic acid for water]. The desired compound was eluted from the column at 24.5 mins. The solvent was evaporated under reduced pressure. The white residue was analysed by NMR and MS.

$^1$H NMR (D$_2$O): 2.15 (m, 2H, OCH$_2$CH$_2$CH$_2$N); 3.08 (s, 12H, NCH$_2$CH$_2$N); 3.26 (s, 12H, NCCH$_2$N); 3.90 (s, 2H, ArCH$_2$); 3.95 (t, 2H, OCH$_2$CH$_2$CH$_2$N); 4.20 (t, 2H, OCH$_2$CH$_2$CH$_2$N); 6.76 (d, 2H, Ar—H); 7.25 (d, 2H, Ar—H); 7.88 (s, 4H, Ar—H); Mass Spec: ESI/MS, m/z=608.5 [M+H]$^+$.

The phthalimide-containing product (11 mg) was dissolved in methanol (10 mL) and hydrazine monohydrate (13

µL) was added to the solution. The resulting solution was left to stir at reflux overnight before the solvent was removed on a rotary evaporator with a 30° C. water bath. The desired compound was purified by reverse-phase HPLC using a water:methanol gradient [10 mins 100% water, 0.1% formic acid; followed 40% methanol, 0.1% formic acid for water]. The desired compound was eluted from the column at 7.6 mins. The solvent was evaporated under reduced pressure. The white residue was analysed by MS. Mass Spec: ESI/MS, m/z=478.3 [M+H]$^+$.

Example 4—Synthesis of Diamsar-CH$_3$ and Diamsar-(CH$_3$)$_2$

Diamsar-CH$_3$ [1-N-methyl)-3,6,10,13,16,19-hexaazabicyclo[6.6.6]eicosane-1,8-diamine] and Diamsar-(CH$_3$)$_2$ [1,13-N,N-Bis-(methyl)-3,6,10,13,16,19-hexaazabicyclo[6.6.6]eicosane-1,8-diamine] were synthesised in the following manner.

Diamsar (50.0 mg; 0.16 mmol) was dissolved in water (1 mL). The pH of the solution was adjusted to 4.5 by the addition of 1M HCl solution. Then 10 µL of the formaldehyde in water was added to the mixture. The reaction was left at room temperature for 1-60 min. MS analysis shows predominantly mono substituted diamsar and some diamsar are present. The imine is then dissolved in water with 10 equivalents of sodium borohydride and the reaction mixture heated at 70° C. for approx 4 hours (or alternatively at 1.5 hour at 80° C.). The resulting crude product was purified by flash chromatography (CH$_2$Cl$_2$/MeOH, 9:1, as the mobile phase) to afford diamsar-CH$_3$. Mass Spec: ESI/MS, m/z=327 [M+H]$^+$ for mono substituted imine of and after reduction m/z=329 [M+H]$^+$. Mass Spec: ESI/MS, m/z=339 [M+H]$^+$ for di-substituted substituted imine of and after reduction m/z=341 [M+H]$^+$.

Example 5—Synthesis of Sarar-DOP

Sarar-DOP (N-(4-((8-amino-3,6,10,13,16,19-hexaaza-bicyclo[6,6,6]icosan-1-ylamino)methyl)phenyl)-2-(3,4-dihydroxyphenyl)acetamide) can be synthesised in the following manner.

To SarAr (54.9 mg; 0.13 mmol) in water (1 mL) was added a solution of 3,4-dihydroxyphenylacetic acid (21.9 mg; 0.13 mmol; in 200 µL water) and N-(3-dimethylaminopropyl)-N'-ethylcarbodiimide hydrochloride (EDC) (75.4 mg; 0.39 mmol in 200 µL water). The mixture was left to stir for 1 hour at 37° C. The desired compound was purified from unreacted reagent by reverse-phase HPLC using a water:methanol gradient [20 min 100% water; followed 70% methanol for water]. The desired compound was eluted from the column at 47 mins. The methanol was evaporated under reduced pressure and the aqueous phase containing the product was lyophilised overnight. The white residue was analysed by NMR and MS. $^1$H NMR (D$_2$O): 3.02 (s, 12H, NCH$_2$CH$_2$N); 3.22 (s, 6H, NCCH$_2$N); 3.24 (s, 6H, NCCH$_2$NCCH$_2$); 3.64 (s, 2H, ArCH$_2$); 3.80 (s, 2H, ArCH$_2$—CO); 6.81 (m, 1H, Ar—H); 6.91 (m, 2H, Ar—H); 7.34 (d, 2H, Ar—H); 7.39 (d, 2H, Ar—H). ESI/MS, m/z=570.4 [M+H]$^+$.

It will be understood to persons skilled in the art of the invention that many modifications may be made without departing from the spirit and scope of the invention.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

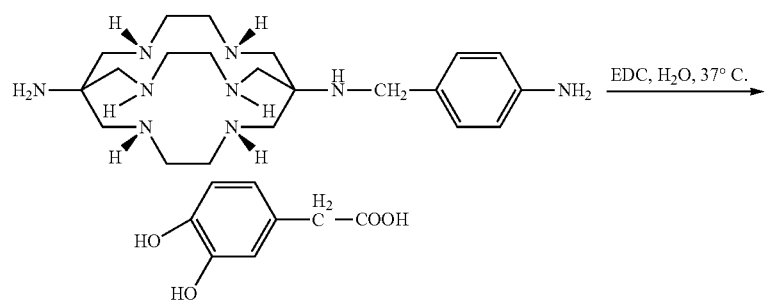

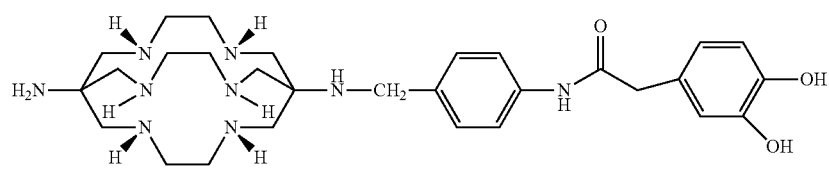

Experiment 6—Synthesis of Benzyldiamsar and Bis-Benzyldiamsar

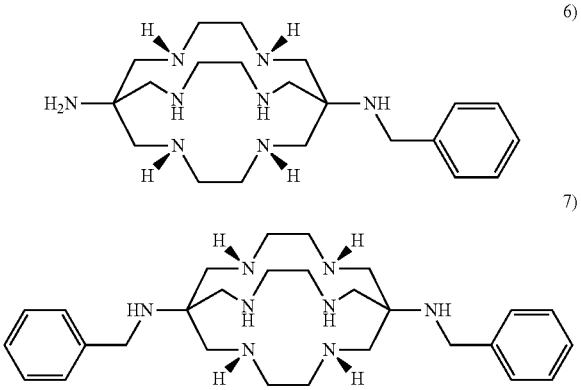

Benzyldiamsar and Bis-benzyldiamsar were produced by adding a diamsar (300 mg) to water 30 mL and then adjusting the pH to 4.0 using 5 M HCl (~550 μL). To this solution was added 75 μL benzaldehyde. This solution was left to stir for 2 mins, after which time a solution of sodium cyanoborohydride (361 mg) in water 10 mL was added. This solution was left to stir for 1 hour before removing the solvent on a rotary evaporator with a 37° C. water bath. The residue was taken up with 50 mL water and extracted with dichloromethane (2×20 mL). The aqueous phase was evaporated. 30 mL of ethanol was added to the residue and heated at 90° C. for 10 mins. The ethanol solution was decanted from the white solid and filtered through a 0.22 m filter unit. The ethanol solutions that contain the desired product were evaporated. The compounds (6, 7) were purified by reverse-phase HPLC using a water:methanol gradient [20 min 100% water, 0.1% formic acid followed 40% methanol, 0.1% formic acid for water]. The desired compounds 6 and 7 were eluted from the column at 7.3 and 27.6 mins respectively. The methanol was evaporated under reduced pressure and the aqueous phase containing the product was lyophilised overnight. The white residue was analysed by NMR and MS.

Benzyldiamsar $^1$H NMR (D$_2$O): 3.00 (s, 12H, NCH$_2$CH$_2$N); 3.19 (s, 6H, NCCH$_2$N); 3.33 (s, 6H, NCCH$_2$NCCH$_2$); 3.99 (s, 2H, ArCH$_2$); 7.55-7.43 (m, 5H, Ar—H). $^{13}$C NMR (D$_2$O): δ 129.1, 128.9, 128.5, 66.6, 55.7, 53.8, 52.8, 52.1, 47.5, 47.4, 45.4. Mass Spec: ESI/MS, m/z=405.5 [M+H]$^+$.

Bis-benzyldiamsar $^1$H NMR (D$_2$O): 3.01 (s, 12H, NCH$_2$CH$_2$N); 3.28 (s, 12H, NCCH$_2$N); 3.84 (s, 4H, ArCH$_2$); 7.50-7.40 (m, 10H, Ar—H); Mass Spec: ESI/MS, m/z=495.5 [M+H]$^+$

Example 7—Synthesis of Ethynyl-Benzyldiamsar

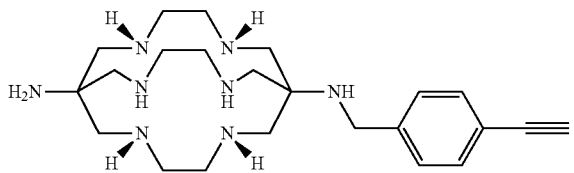

Ethynyl-benzyldiamsar was produced by adding a diamsar (300 mg) to water 60 mL and then adjusting the pH to 4.0 using 5 M HCl (~550 μL). To this solution was added 249 mg 4-Ethynyl-benzaldehyde in 40 mL ethanol. This solution was left to stir for 2 mins, after which time a solution of sodium cyanoborohydride (361 mg) in water 10 mL was added. This solution was left to stir for 1 hour before the residue was filtered through cotton and removing the solvent on a rotary evaporator with a 37° C. water bath. The residue was taken up with 50 mL water and extracted with dichloromethane (1×10 mL). The aqueous phase was evaporated. 30 mL of ethanol was added to the residue and heated at 90° C. for 10 mins. The ethanol solution was decanted from the white solid and filtered through a 0.22 m filter unit. The ethanol solutions that contain the desired product were evaporated. The desired compound was purified by reverse-phase HPLC using a water:methanol gradient [20 min 100% water, 0.1% formic acid; followed 40% methanol, 0.1% formic acid for water]. The desired compound was eluted from the column at 27.5 mins. The solvent was evaporated under reduced pressure. The white residue was analysed by NMR and MS.

Ethynyl-Benzyldiamsar $^1$H NMR (D$_2$O): 2.90 (s, 12H, NCH$_2$CH$_2$N); 3.29 (s, 6H, NCCH$_2$N); 3.57 (s, 6H, NCCH$_2$NCCH$_2$); 3.92 (s, 1H, ArC≡CH); 4.19 (s, 2H, ArCH$_2$); 7.51 (d, 2H, Ar—H); 8.13 (d, 2H, Ar—H). $^{13}$C NMR (D$_2$O): δ 134.9, 132.5, 122.0, 83.2, 79.1, 56.2, 52.9, 52.7, 52.0, 47.5, 47.1, 45.0. Mass Spec: ESI/MS, m/z=429.4 [M+H]$^+$.

The invention claimed is:

1. A method for radioimaging cancer in a subject, comprising administering to the subject an effective amount of a radiolabelled complex of a compound consisting of Formula:

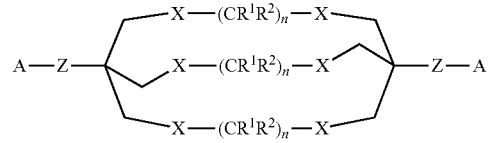

wherein:
each $R^1$ and $R^2$ is hydrogen;
n=2;
each X is NH;
each Z is an optional spacing group which, when present, is independently selected from the group consisting of an optionally substituted $C_1$-$C_{10}$ alkyl, optionally substituted aryl and optionally substituted heterocycle;
each A is independently selected from the group consisting of hydrogen, halogen, hydroxyl, nitro, optionally substituted amino, optionally substituted alkyl, optionally substituted aryl, optionally substituted aralkyl, optionally substituted heterocycle, isothiocyanate, cyano, —NH—COCH$_2$Br, —COOR', —NHCR$^3$R$^4$R$^5$ and —NH—COCH═CH—COOR', provided that at least one A is or contains —NHCR$^3$R$^4$R$^5$;
R' is selected from the group consisting of hydrogen, optionally substituted alkyl and optionally substituted aryl;
$R^3$ and $R^4$ are independently selected from the group consisting of H, alkyl and aryl; and
$R^5$ is a substituted alkyl, substituted aryl or substituted heterocycle, wherein the substituted alkyl, substituted aryl or substituted heterocycle contains an alkene, alkyne, maleimido, or phthalimido functional group, or contains a functional group that is selected from the group consisting of:

—N$_3$, —C≡CH, —C≡N,

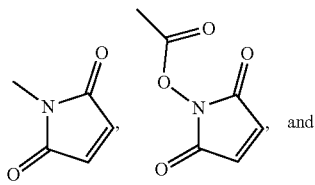 and

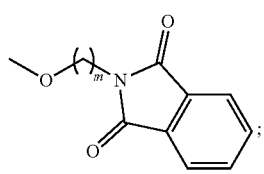

wherein m is 1 to 8;

or a pharmaceutically acceptable salt thereof;

wherein the complex is radiolabelled with a radionuclide selected from the group consisting of $^{48}$V, $^{52}$Fe, $^{52m}$Mn, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{81}$Rb, $^{83}$Sr, $^{89}$Zr, $^{94m}$Tc, $^{94}$Tc, $^{110}$In, $^{67}$Cu, $^{67}$Ga, $^{188}$Re, $^{186}$Re, $^{195m}$Pt, $^{191}$Pt, and $^{105}$Rh; and detecting a localised concentration of the compound;

wherein the cancer is selected from the group consisting of lung cancer, lymphoma, colorectal cancer, breast cancer, liver cancer, neuroblastoma, prostate cancer, bladder cancer, cervical cancer, and ovarian cancer.

2. The method according to claim 1, wherein the radionuclide is $^{60}$Cu, $^{61}$Cu, $^{62}$Cu, $^{64}$Cu, or $^{67}$Cu.

3. The method according to claim 1, wherein the cancer is selected from the group consisting of colon cancer, ovarian cancer, lymphoma, breast cancer and bladder cancer.

4. A method for radiotherapy of cancer, in a subject, comprising administering to the subject an effective amount of a radiolabelled complex of a compound consisting of Formula:

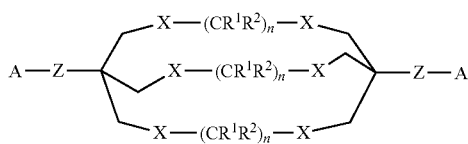

wherein:

each R$^1$ and R$^2$ is hydrogen;

n=2;

each X is NH;

each Z is an optional spacing group which, when present, is independently selected from the group consisting of an optionally substituted C$_1$-C$_{10}$ alkyl, optionally substituted aryl and optionally substituted heterocycle;

each A is independently selected from the group consisting of hydrogen, halogen, hydroxyl, nitro, optionally substituted amino, optionally substituted alkyl, optionally substituted aryl, optionally substituted aralkyl, optionally substituted heterocycle, isothiocyanate, cyano, —NH—COCH$_2$Br, —COOR', —NHCR$^3$R$^4$R$^5$ and —NH—COCH=CH—COOR', provided that at least one A is or contains —NHCR$^3$R$^4$R$^5$;

R' is selected from the group consisting of hydrogen, optionally substituted alkyl and optionally substituted aryl;

R$^3$ and R$^4$ are independently selected from the group consisting of H, alkyl and aryl; and R$^5$ is a substituted alkyl, substituted aryl or substituted heterocycle, wherein the substituted alkyl, substituted aryl or substituted heterocycle contains an alkene, alkyne, maleimido, or phthalimido functional group, or contains a functional group that is selected from the group consisting of:

—N$_3$, —C≡CH, —C≡N,

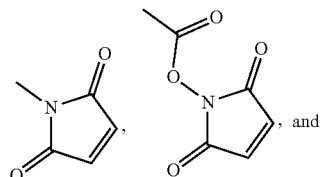, and

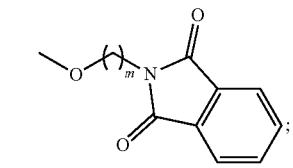;

wherein m is 1 to 8;

or a pharmaceutically acceptable salt thereof;

wherein the complex is radiolabelled with a radionuclide selected from the group consisting of $^{48}$V, $^{52}$Fe, $^{52m}$Mn, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{81}$Rb, $^{83}$Sr, $^{89}$Zr, $^{94m}$Tc, $^{94}$Tc, $^{110}$In, $^{67}$Cu, $^{67}$Ga, $^{188}$Re, $^{186}$Re, $^{195m}$Pt, $^{191}$Pt, and $^{105}$Rh;

wherein the cancer is selected from the group consisting of lung cancer, lymphoma, colorectal cancer, breast cancer, liver cancer, neuroblastoma, prostate cancer, bladder cancer, cervical cancer, and ovarian cancer.

5. The method according to claim 1, wherein the radioimaging is by positron emission tomography (PET), single photon emission computed tomography (SPECT) or fluorescence imaging.

6. The method according to claim 1, wherein the compound is conjugated to a molecular recognition unit, wherein the molecular recognition unit is selected from the group consisting of an antibody, protein, peptide, carbohydrate, nucleic acid, oligonucleotide, oligosaccharide, liposome, siRNA, RNA, DNA, ssDNA, nucleotide, dendrimer, polysaccharide, amino acid, enzyme, oligopeptide, and steroid.

7. The method according to claim 1, wherein the compound is one of:
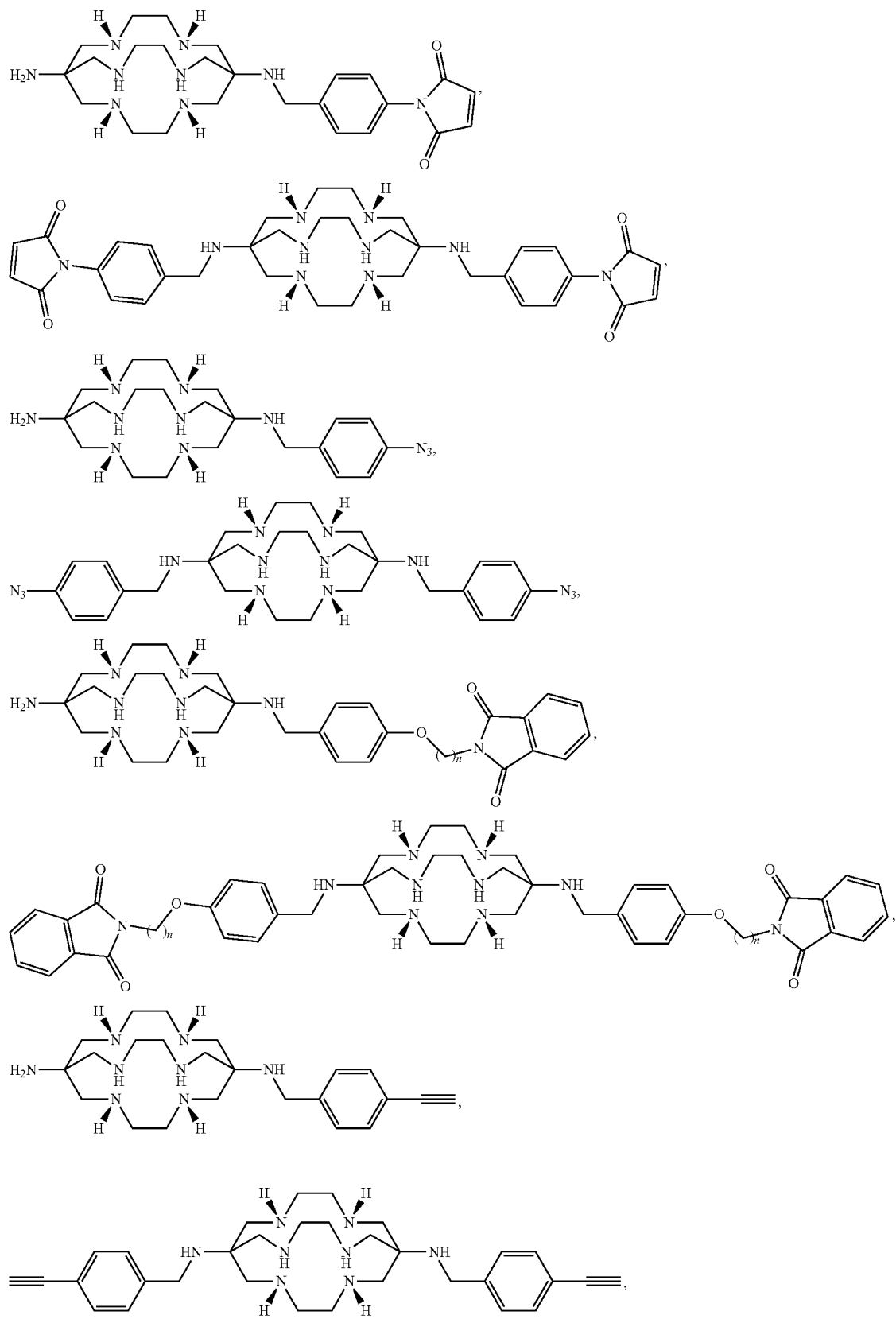

-continued
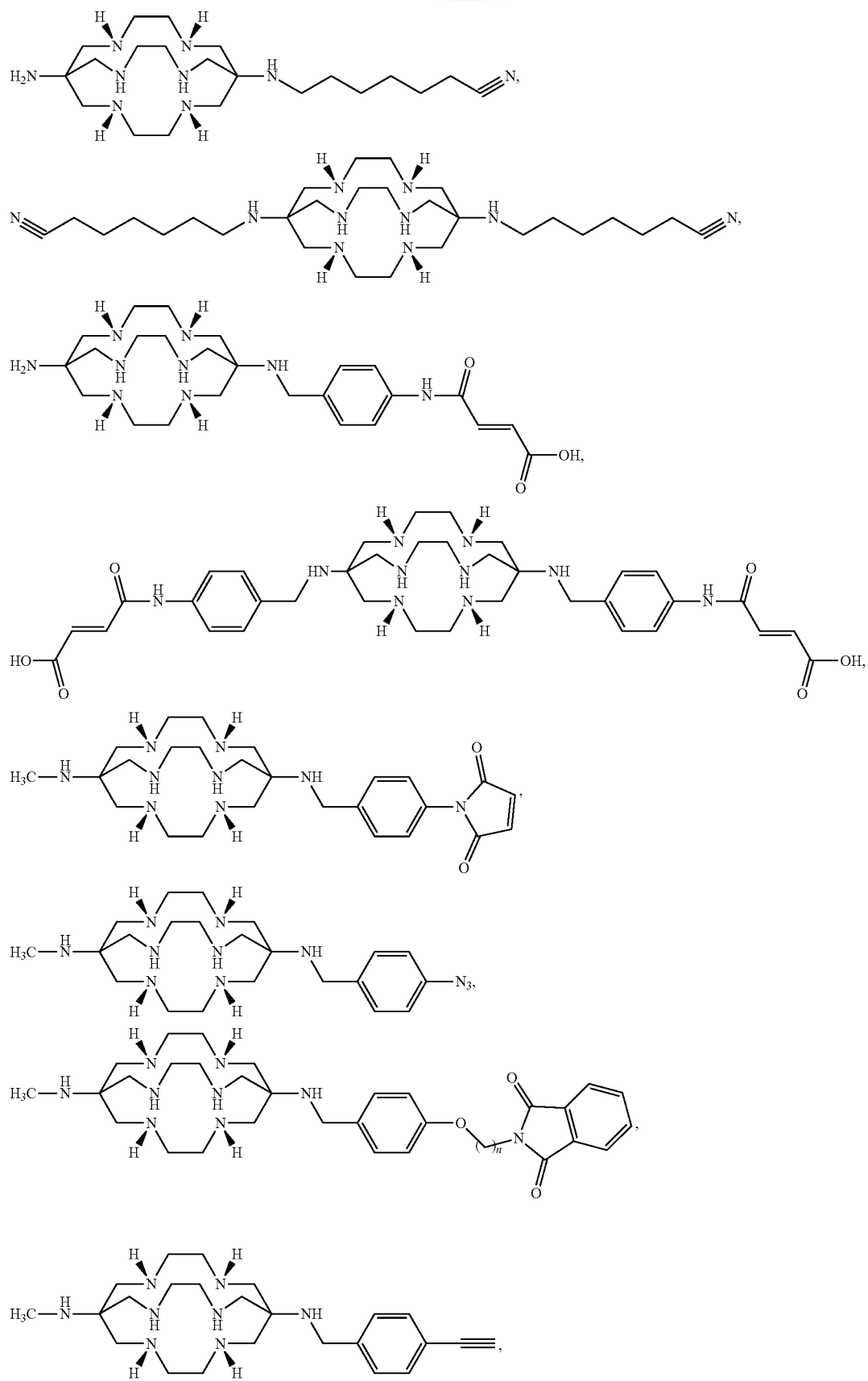

-continued
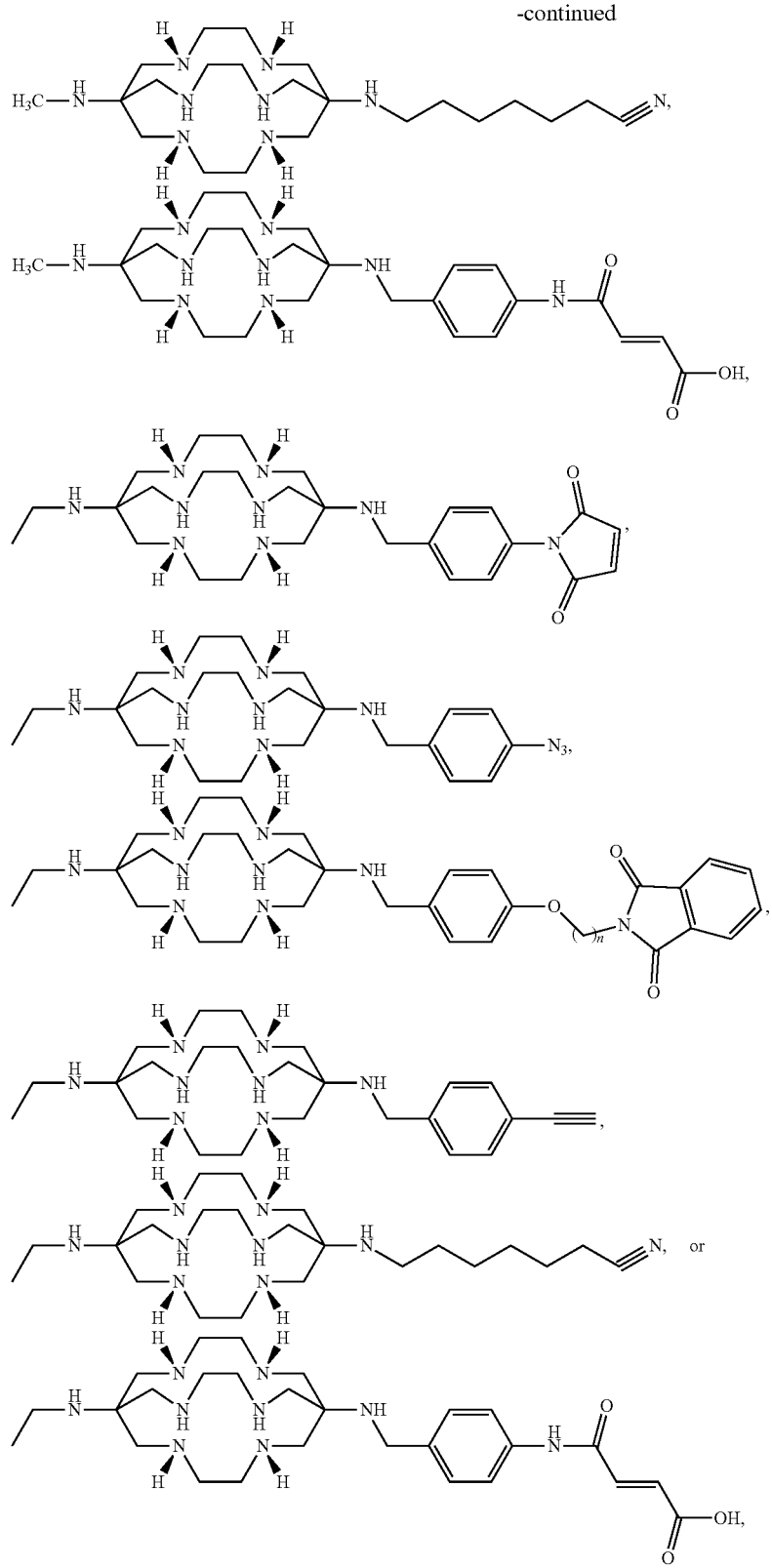
wherein n is an integer of from 1 to 5.
8. The method according to claim 4, wherein the radionuclide is $^{60}$Cu $^{61}$Cu, $^{62}$Cu, $^{64}$Cu, $^{67}$Cu, or $^{195m}$Pt.
9. The method according to claim 4, wherein the compound is conjugated to a molecular recognition unit, wherein the molecular recognition unit is selected from the group consisting of an antibody, protein, peptide, carbohydrate, nucleic acid, oligonucleotide, oligosaccharide, liposome, siRNA, RNA, DNA, ssDNA, nucleotide, dendrimer, polysaccharide, amino acid, enzyme, oligopeptide, and steroid.
10. The method according to claim 4, wherein the compound is one of:
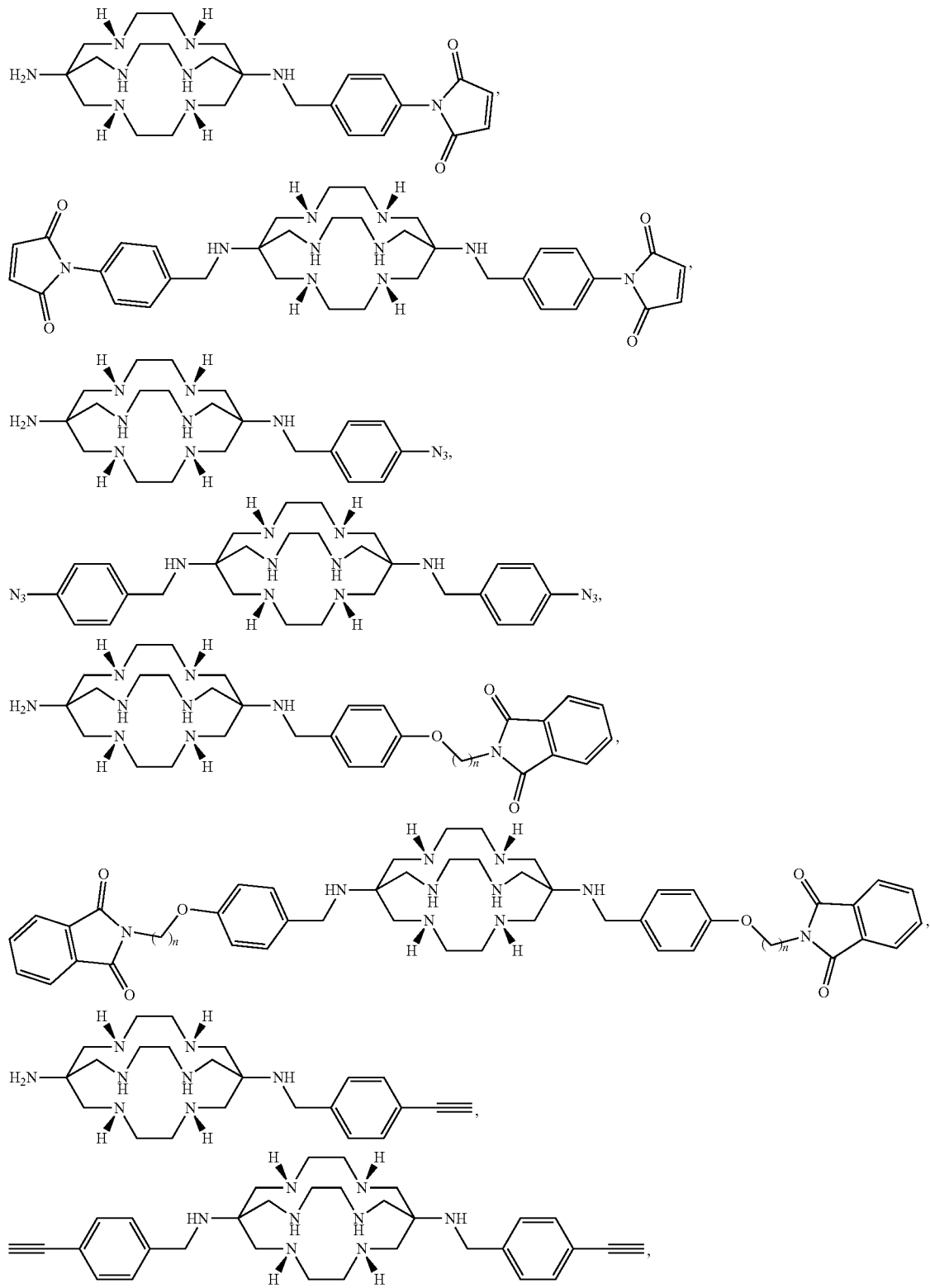

-continued
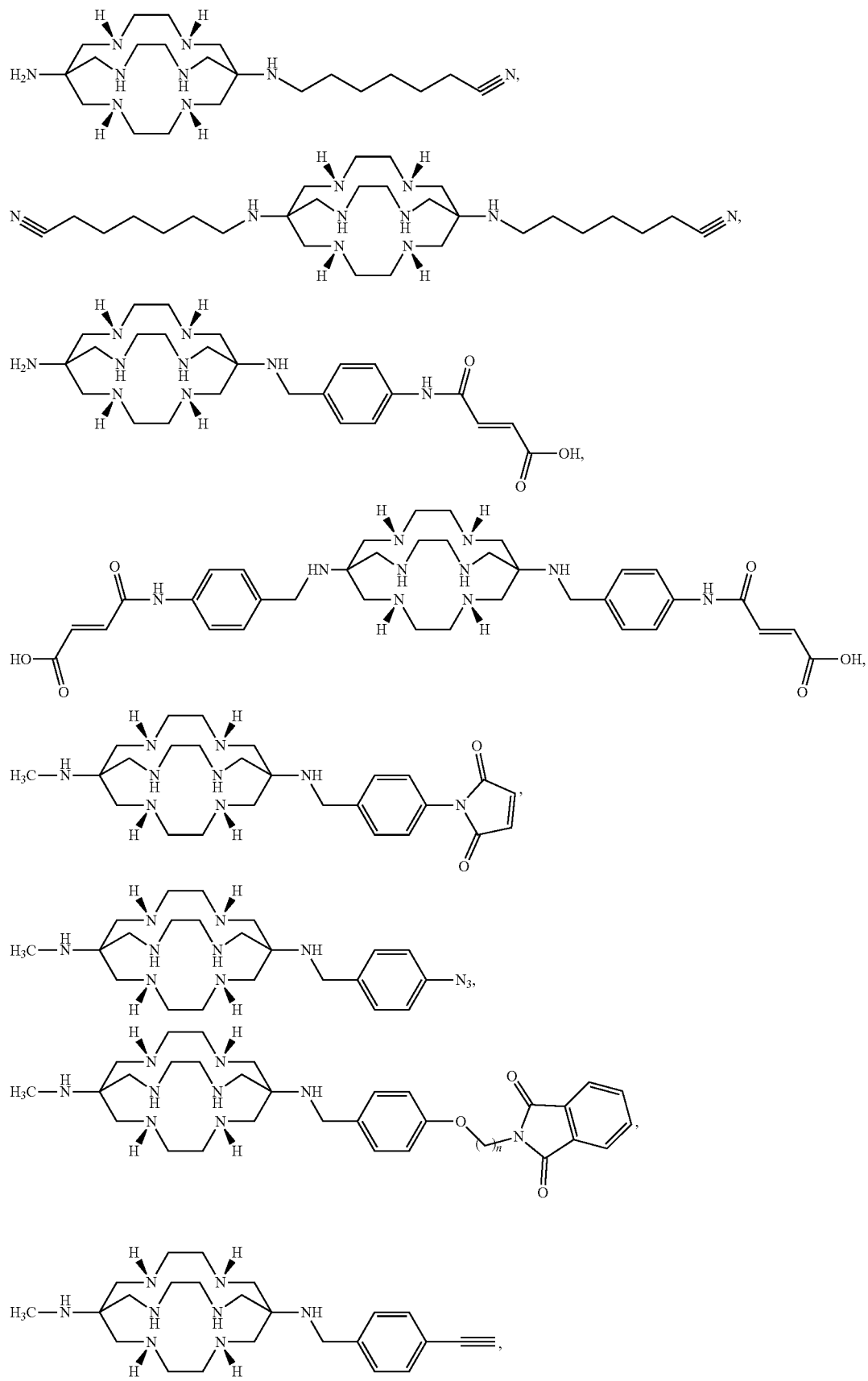

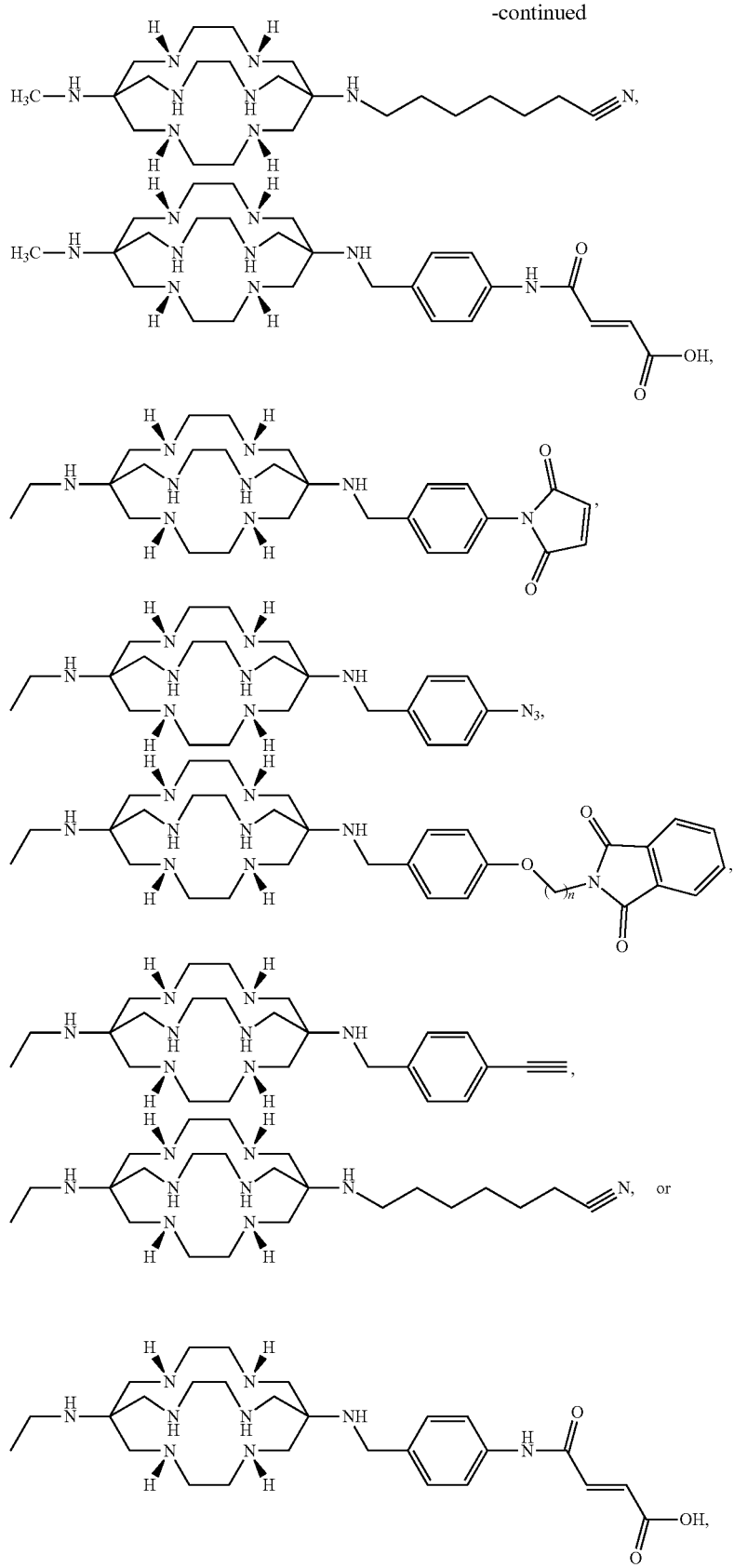
wherein n is an integer of from 1 to 5.

11. A method for radioimaging an autoimmune disease in a subject, comprising administering to the subject an effective amount of a radiolabelled complex of a compound consisting of Formula:

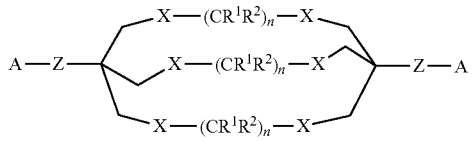

wherein:

each $R^1$ and $R^2$ is hydrogen;

n=2;

each X is NH;

each Z is an optional spacing group which, when present, is independently selected from the group consisting of an optionally substituted $C_1$-$C_{10}$ alkyl, optionally substituted aryl and optionally substituted heterocycle;

each A is independently selected from the group consisting of hydrogen, halogen, hydroxyl, nitro, optionally substituted amino, optionally substituted alkyl, optionally substituted aryl, optionally substituted aralkyl, optionally substituted heterocycle, isothiocyanate, cyano, —NH—COCH$_2$Br, —COOR', —NHCR$^3$R$^4$R$^5$ and —NH—COCH=CH—COOR', provided that at least one A is or contains —NHCR$^3$R$^4$R$^5$;

R' is selected from the group consisting of hydrogen, optionally substituted alkyl and optionally substituted aryl;

$R^3$ and $R^4$ are independently selected from the group consisting of H, alkyl and aryl; and $R^5$ is a substituted alkyl, substituted aryl or substituted heterocycle, wherein the substituted alkyl, substituted aryl or substituted heterocycle contains an alkene, alkyne, maleimido, or phthalimido functional group, or contains a functional group that is selected from the group consisting of:

—N$_3$, —C≡CH, —C≡N,

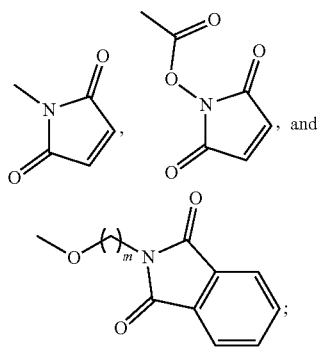

wherein m is 1 to 8;

or a pharmaceutically acceptable salt thereof;

wherein the complex is radiolabelled with a radionuclide selected from the group consisting of $^{48}$V, $^{52}$Fe, $^{52m}$Mn, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{81}$Rb, $^{83}$Sr, $^{89}$Zr, $^{94m}$Tc, $^{94}$Tc, $^{110}$In, $^{67}$Cu, $^{67}$Ga, $^{188}$Re, $^{186}$Re, $^{195m}$Pt, $^{191}$Pt, and $^{105}$Rh; and detecting a localised concentration of the compound;

wherein the autoimmune disease is selected from the group consisting of rheumatoid arthritis, multiple sclerosis, and psoriasis.

12. The method according to claim 11, wherein the radionuclide is $^{60}$Cu, $^{61}$Cu, $^{62}$Cu, $^{64}$Cu or $^{67}$Cu.

13. The method according to claim 11, wherein the compound is conjugated to a molecular recognition unit, wherein the molecular recognition unit is selected from the group consisting of an antibody, protein, peptide, carbohydrate, nucleic acid, oligonucleotide, oligosaccharide, liposome, siRNA, RNA, DNA, ssDNA, nucleotide, dendrimer, polysaccharide, amino acid, enzyme, oligopeptide, and steroid.

14. The method according to claim 11, wherein the radioimaging is by positron emission tomography (PET), single photon emission computed tomography (SPECT) or fluorescence imaging.

15. The method according to claim 11, wherein the compound is one of:

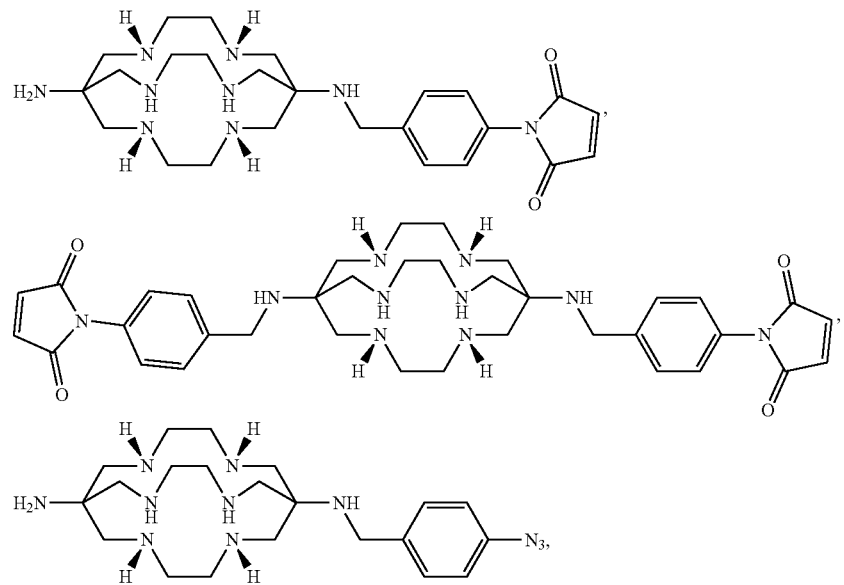

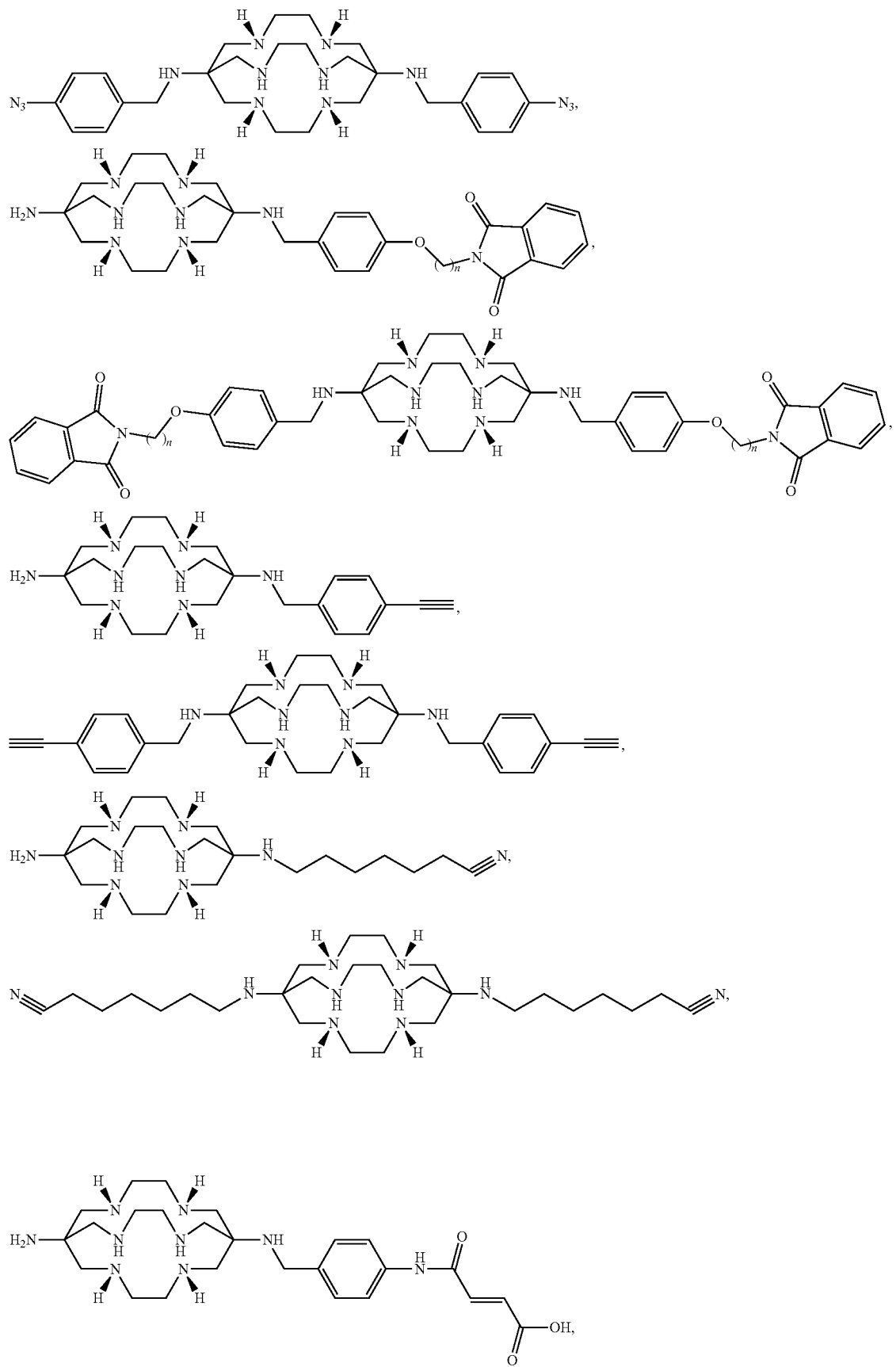

-continued
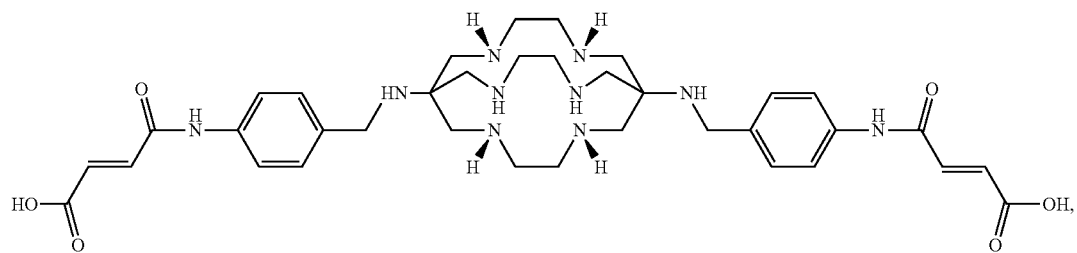
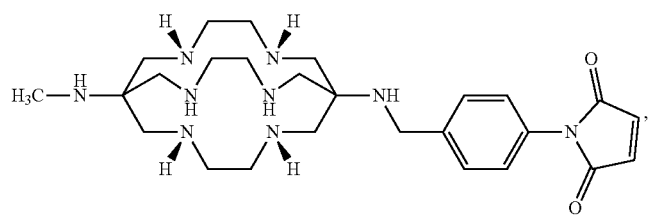
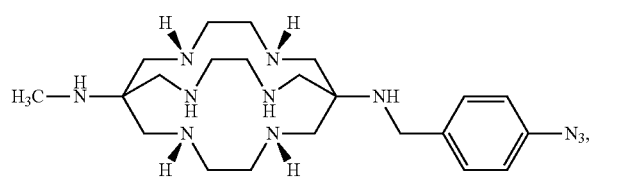
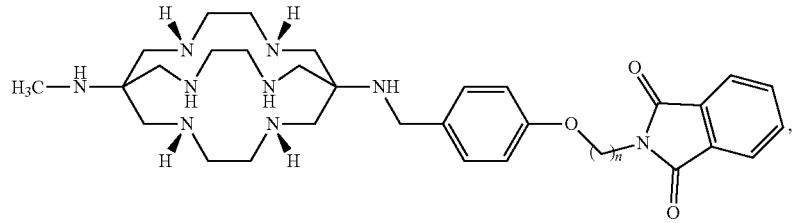
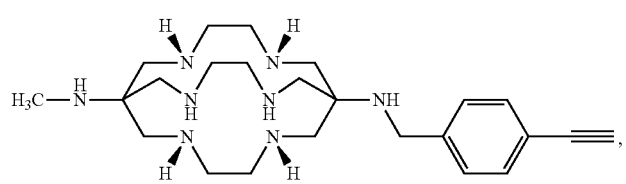
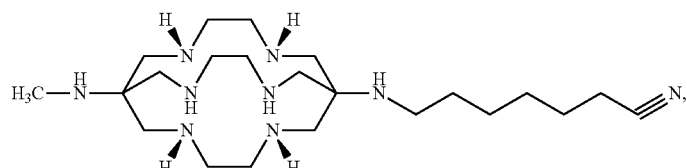
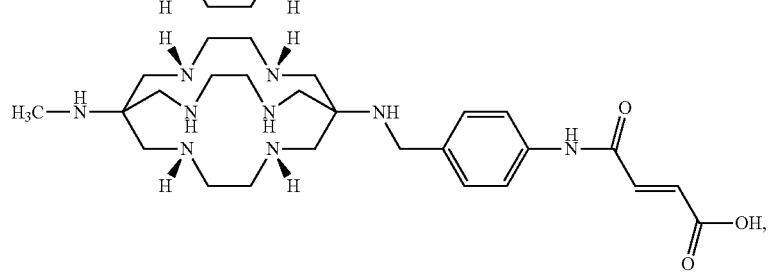
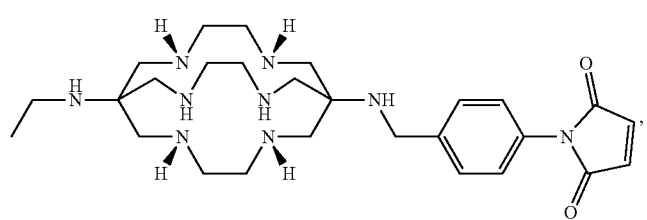

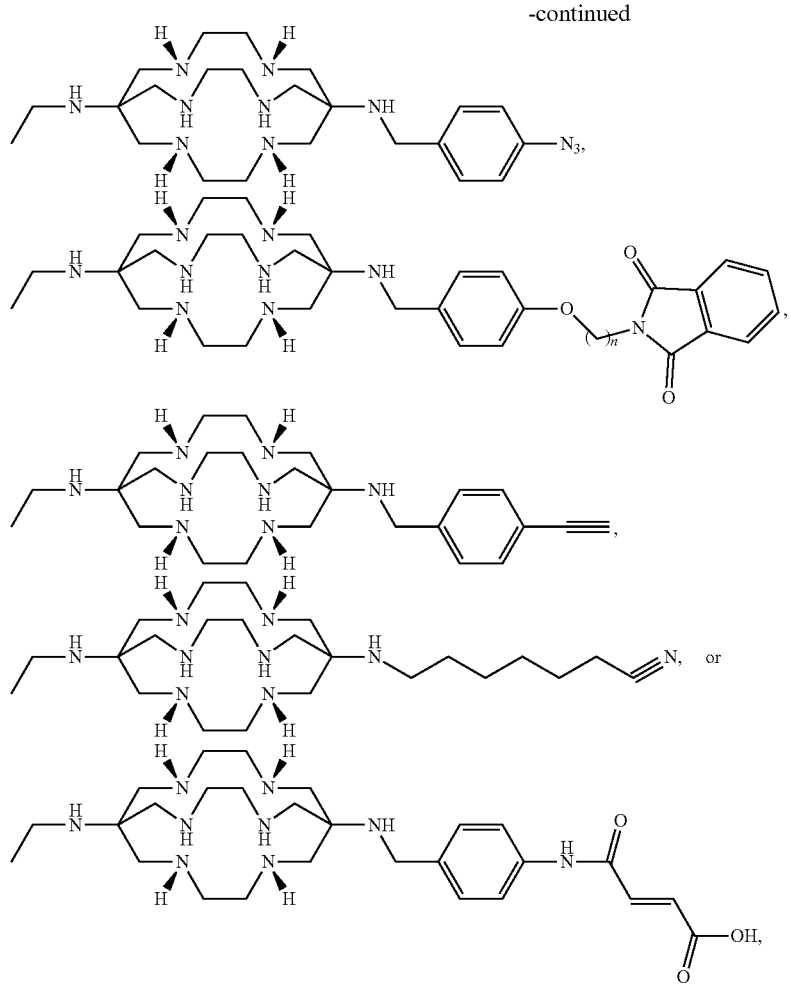

wherein n is an integer of from 1 to 5.

16. A method for radiotherapy of an autoimmune disease in a subject, comprising administering to the subject an effective amount of a radiolabelled complex of a compound consisting of Formula:

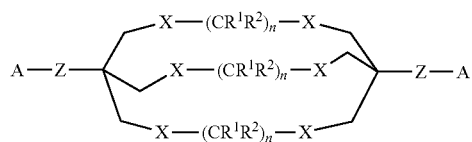

wherein:
each $R^1$ and $R^2$ is hydrogen;
n=2;
each X is NH;
each Z is an optional spacing group which, when present, is independently selected from the group consisting of an optionally substituted $C_1$-$C_{10}$ alkyl, optionally substituted aryl and optionally substituted heterocycle;
each A is independently selected from the group consisting of hydrogen, halogen, hydroxyl, nitro, optionally substituted amino, optionally substituted alkyl, optionally substituted aryl, optionally substituted aralkyl, optionally substituted heterocycle, isothiocyanate, cyano, —NH—COCH$_2$Br, —COOR', —NHCR$^3$R$^4$R$^5$ and —NH—COCH=CH—COOR', provided that at least one A is or contains —NHCR$^3$R$^4$R$^5$;

R' is selected from the group consisting of hydrogen, optionally substituted alkyl and optionally substituted aryl;

$R^3$ and $R^4$ are independently selected from the group consisting of H, alkyl and aryl; and $R^5$ is a substituted alkyl, substituted aryl or substituted heterocycle, wherein the substituted alkyl, substituted aryl or substituted heterocycle contains an alkene, alkyne, maleimido, or phthalimido functional group, or contains a functional group that is selected from the group consisting of:

—N$_3$, —C≡CH, —C≡N,

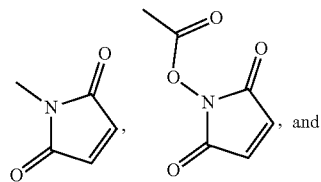

, and

-continued

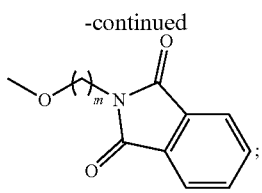

wherein m is 1 to 8;
or a pharmaceutically acceptable salt thereof;
wherein the complex is radiolabelled with a radionuclide selected from the group consisting of $^{48}$V, $^{52}$Fe, $^{52m}$Mn, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{81}$Rb, $^{83}$Sr, $^{89}$Zr, $^{94m}$Tc, $^{94}$Tc, $^{110}$In, $^{67}$Cu, $^{67}$Ga, $^{188}$Re, $^{186}$Re, $^{195m}$Pt, $^{191}$Pt, and $^{105}$Rh; and wherein the autoimmune disease is selected from the group consisting of rheumatoid arthritis, multiple sclerosis, and psoriasis.

17. The method according to claim 16, wherein the radionuclide is $^{60}$Cu, $^{61}$Cu, $^{62}$Cu, $^{64}$Cu, $^{67}$Cu, or $^{195m}$Pt.

18. The method according to claim 16, wherein the compound is conjugated to a molecular recognition unit, wherein the molecular recognition unit is selected from the group consisting of an antibody, protein, peptide, carbohydrate, nucleic acid, oligonucleotide, oligosaccharide, liposome, siRNA, RNA, DNA, ssDNA, nucleotide, dendrimer, polysaccharide, amino acid, enzyme, oligopeptide, and steroid.

19. The method according to claim 16, wherein the compound is one of:

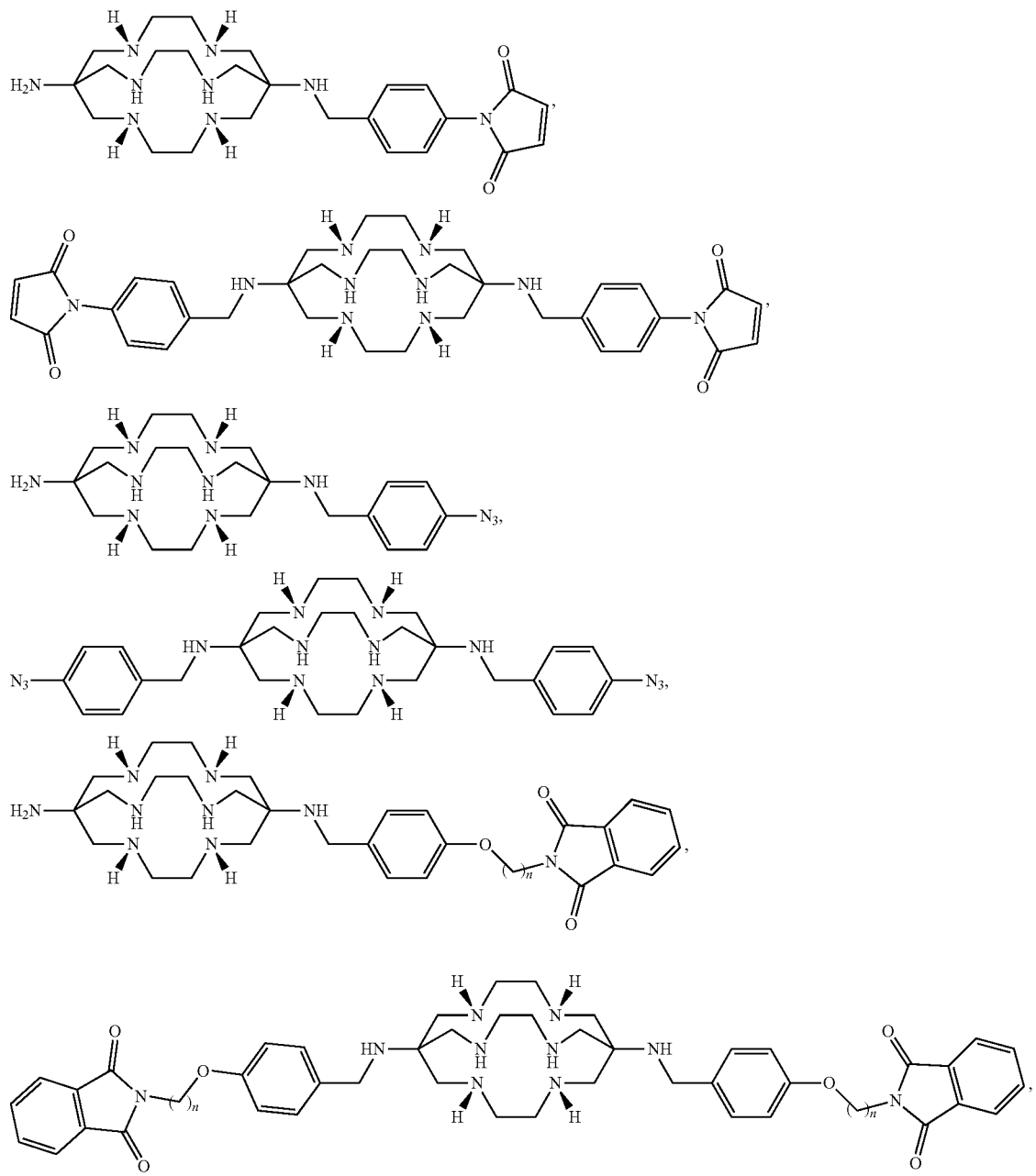

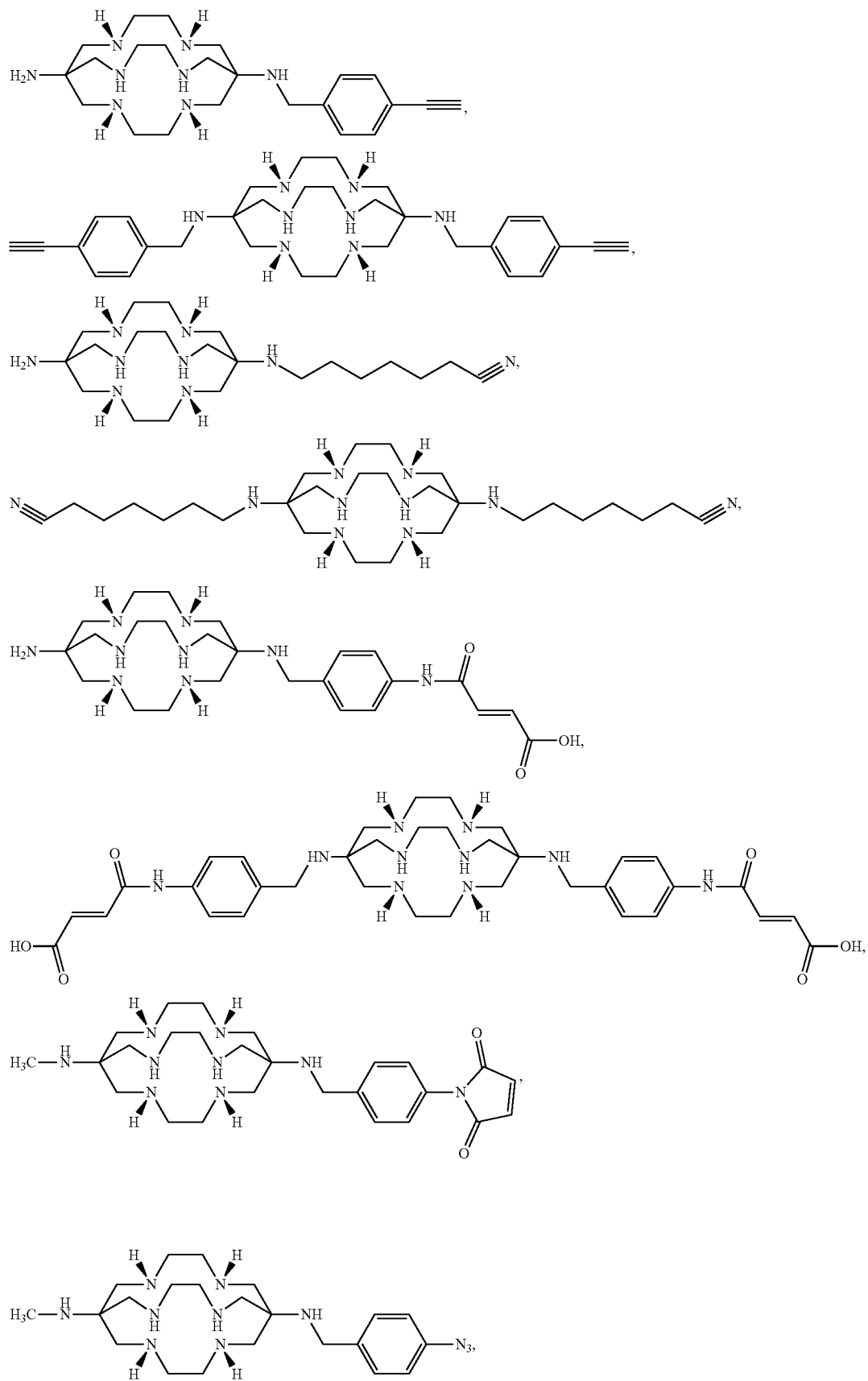

-continued
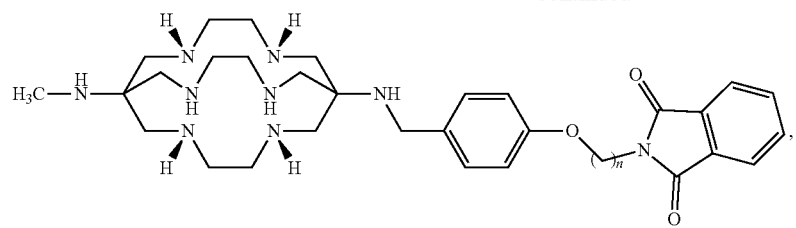
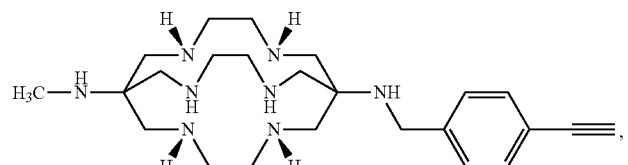
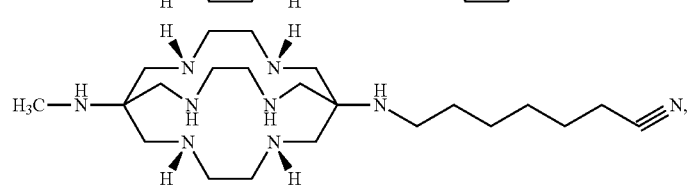
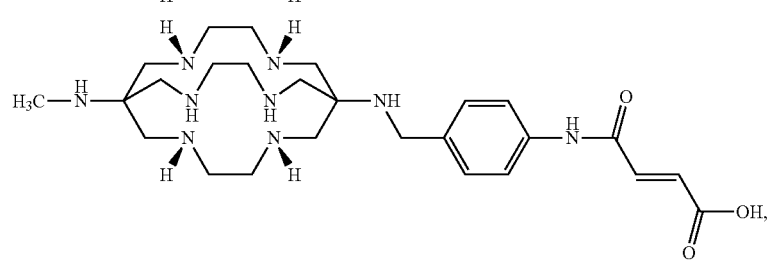
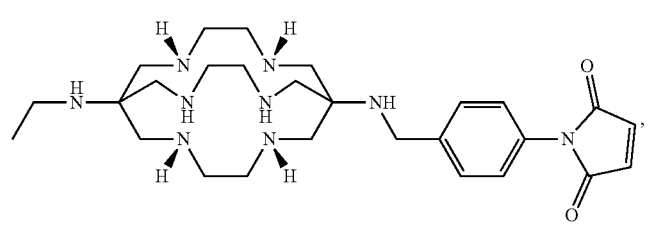
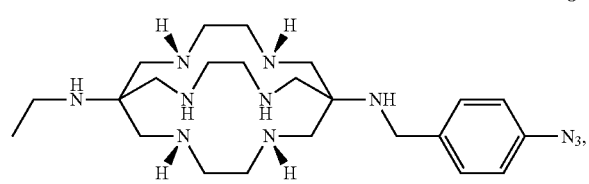
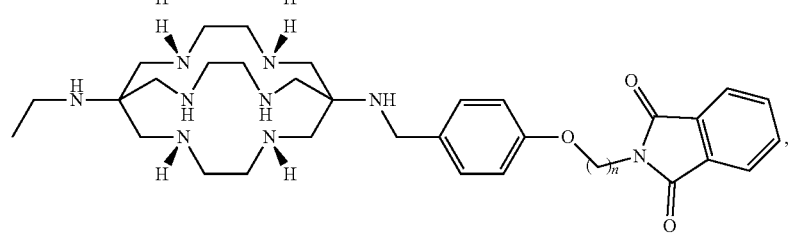

-continued

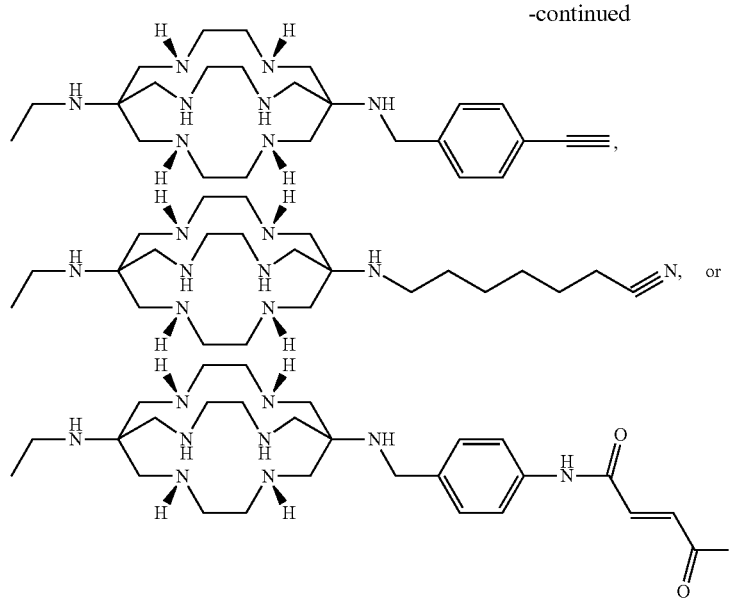

wherein n is an integer of from 1 to 5.

20. A method for radioimaging a respiratory syncytial virus infection in a subject, comprising administering to the subject an effective amount of a radiolabelled complex of a compound consisting of Formula:

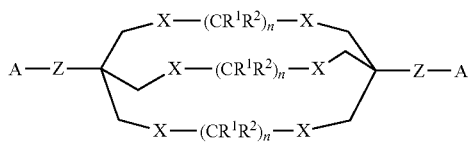

wherein:
each $R^1$ and $R^2$ is hydrogen;
n=2;
each X is NH;
each Z is an optional spacing group which, when present, is independently selected from the group consisting of an optionally substituted $C_1$-$C_{10}$ alkyl, optionally substituted aryl and optionally substituted heterocycle;
each A is independently selected from the group consisting of hydrogen, halogen, hydroxyl, nitro, optionally substituted amino, optionally substituted alkyl, optionally substituted aryl, optionally substituted aralkyl, optionally substituted heterocycle, isothiocyanate, cyano, —NH—COCH$_2$Br, —COOR', —NHCR$^3$R$^4$R$^5$ and —NH—COCH=CH—COOR', provided that at least one A is or contains —NHCR$^3$R$^4$R$^5$;
R' is selected from the group consisting of hydrogen, optionally substituted alkyl and optionally substituted aryl;
$R^3$ and $R^4$ are independently selected from the group consisting of H, alkyl and aryl; and
$R^5$ is a substituted alkyl, substituted aryl or substituted heterocycle, wherein the substituted alkyl, substituted aryl or substituted heterocycle contains an alkene, alkyne, maleimido, or phthalimido functional group, or contains a functional group that is selected from the group consisting of:

—N$_3$, —C≡CH, —C≡N,

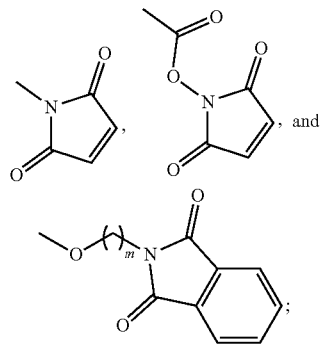

wherein m is 1 to 8;
or a pharmaceutically acceptable salt thereof;
wherein the complex is radiolabelled with a radionuclide selected from the group consisting of $^{48}$V, $^{52}$Fe, $^{52m}$Mn, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{81}$Rb, $^{83}$Sr, $^{89}$Zr, $^{94m}$Tc, $^{94}$Tc, $^{110}$In, $^{67}$Cu, $^{67}$Ga, $^{188}$Re, $^{186}$Re, $^{195m}$Pt, $^{191}$Pt, and $^{105}$Rh; and
detecting a localised concentration of the compound;
wherein the autoimmune disease is selected from the group consisting of rheumatoid arthritis, multiple sclerosis, and psoriasis.

21. The method according to claim 20, wherein the radionuclide is $^{60}$Cu, $^{61}$Cu, $^{62}$Cu, $^{64}$Cu or $^{67}$Cu.

22. The method according to claim 20, wherein the compound is conjugated to a molecular recognition unit, wherein the molecular recognition unit is selected from the group consisting of an antibody, protein, peptide, carbohydrate, nucleic acid, oligonucleotide, oligosaccharide, liposome, siRNA, RNA, DNA, ssDNA, nucleotide, dendrimer, polysaccharide, amino acid, enzyme, oligopeptide, and steroid.

23. The method according to claim 20, wherein the radioimaging is by positron emission tomography (PET), single photon emission computed tomography (SPECT) or fluorescence imaging.

24. The method according to claim 20, wherein the compound is one of:
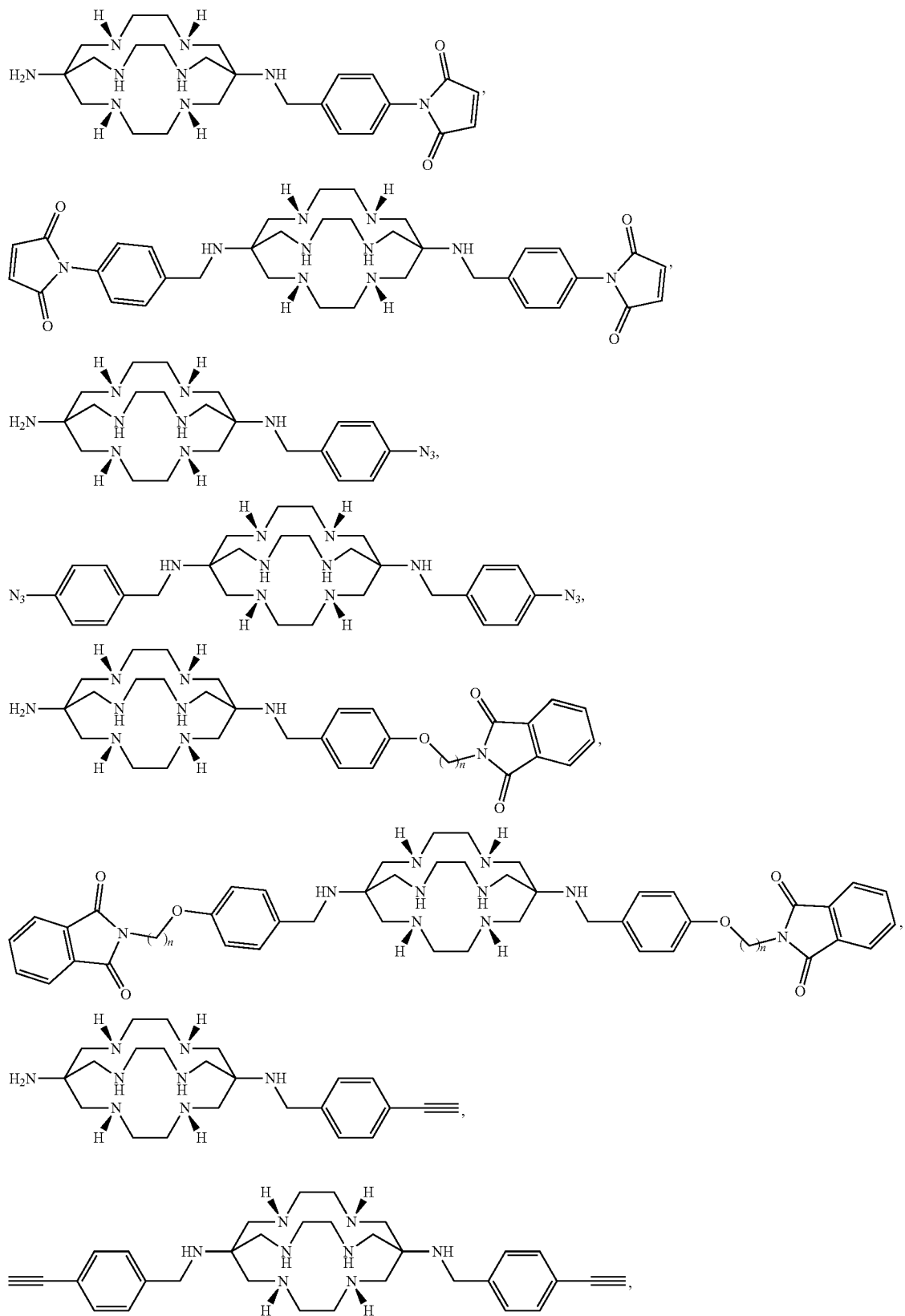

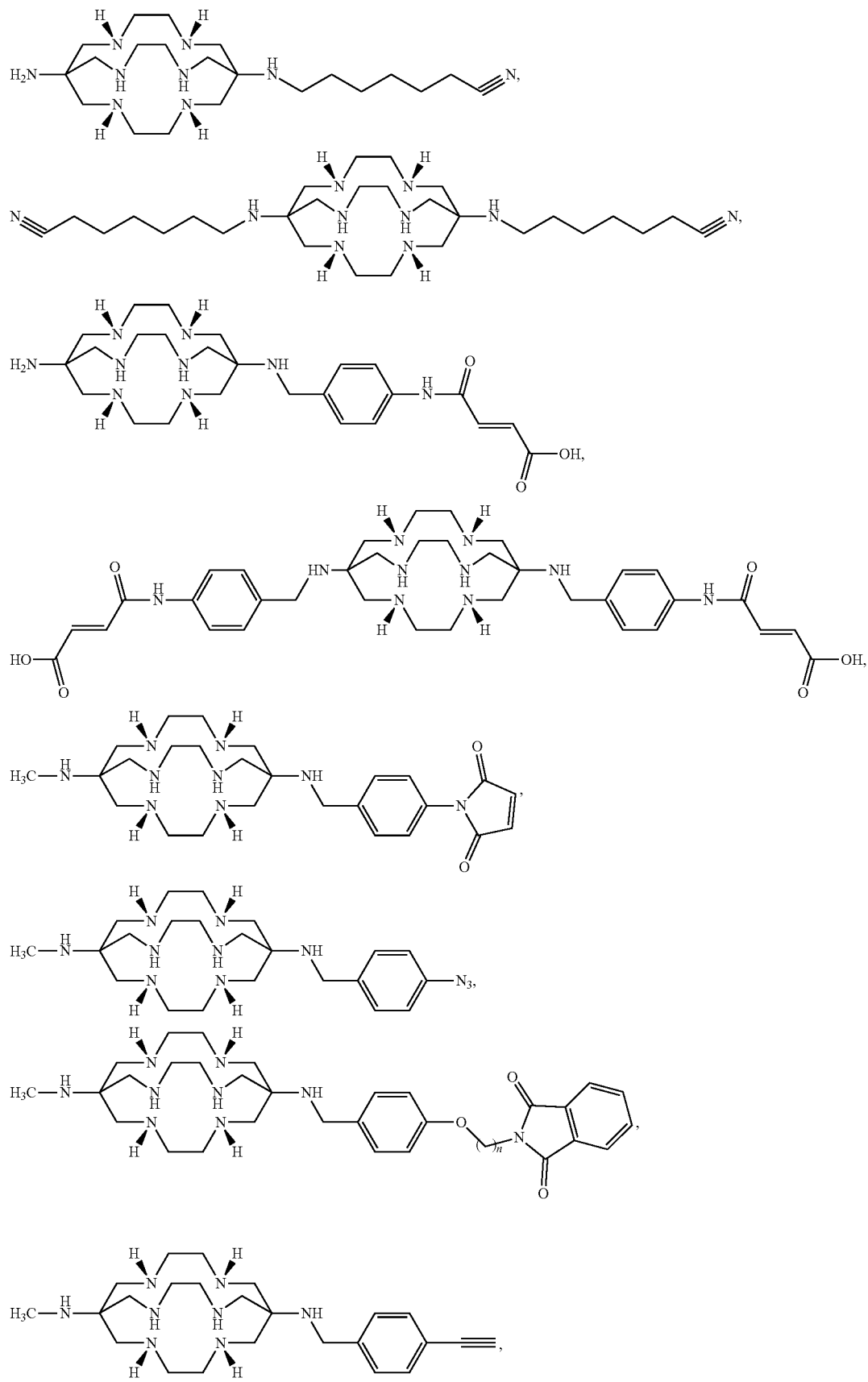

-continued
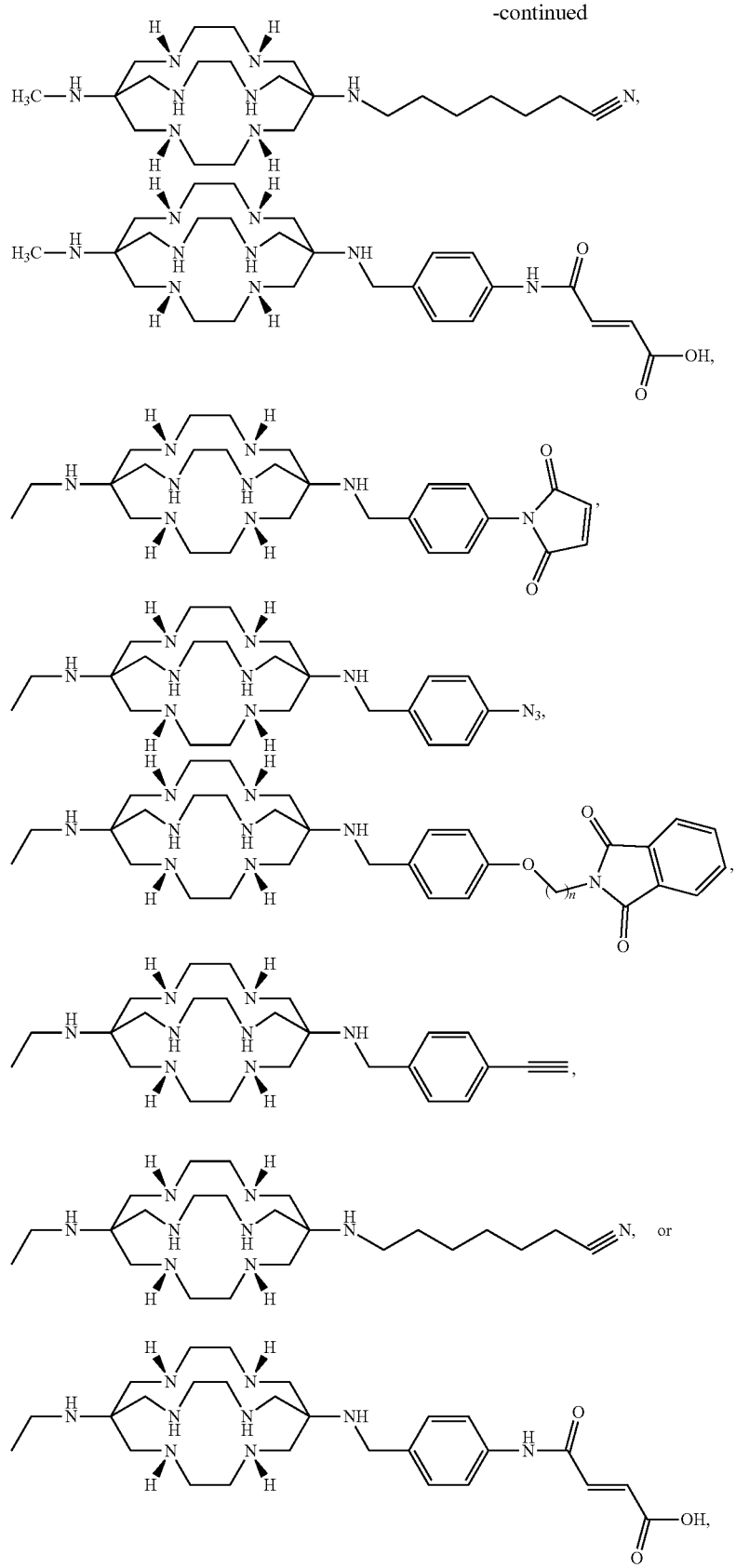
wherein n is an integer of from 1 to 5.

25. A method for radiotherapy of a respiratory syncytial virus in a subject, comprising administering to the subject an effective amount of a radiolabelled complex of a compound consisting of Formula:

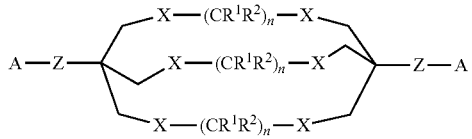

wherein:
each $R^1$ and $R^2$ is hydrogen;
n=2;
each X is NH;
each Z is an optional spacing group which, when present, is independently selected from the group consisting of an optionally substituted $C_1$-$C_{10}$ alkyl, optionally substituted aryl and optionally substituted heterocycle;
each A is independently selected from the group consisting of hydrogen, halogen, hydroxyl, nitro, optionally substituted amino, optionally substituted alkyl, optionally substituted aryl, optionally substituted aralkyl, optionally substituted heterocycle, isothiocyanate, cyano, —NH—COCH$_2$Br, —COOR', —NHCR$^3$R$^4$R$^5$ and —NH—COCH=CH—COOR', provided that at least one A is or contains —NHCR$^3$R$^4$R$^5$;
R' is selected from the group consisting of hydrogen, optionally substituted alkyl and optionally substituted aryl;
$R^3$ and $R^4$ are independently selected from the group consisting of H, alkyl and aryl; and
$R^5$ is a substituted alkyl, substituted aryl or substituted heterocycle, wherein the substituted alkyl, substituted aryl or substituted heterocycle contains an alkene, alkyne, maleimido, or phthalimido functional group, or contains a functional group that is selected from the group consisting of:

—N$_3$, —C≡CH, —C≡N,

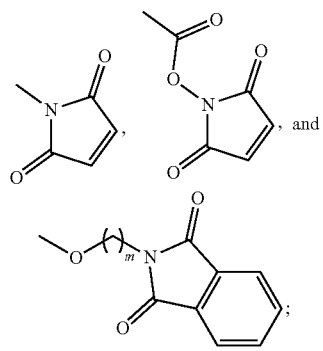

wherein m is 1 to 8;
or a pharmaceutically acceptable salt thereof;
wherein the complex is radiolabelled with a radionuclide selected from the group consisting of $^{48}$V, $^{52}$Fe, $^{52m}$Mn, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{81}$Rb, $^{83}$Sr, $^{89}$Zr, $^{94m}$Tc, $^{94}$Tc, $^{110}$In, $^{67}$Cu, $^{67}$Ga, $^{188}$Re, $^{186}$Re, $^{195m}$Pt, $^{191}$Pt, and $^{105}$Rh; and
wherein the autoimmune disease is selected from the group consisting of rheumatoid arthritis, multiple sclerosis, and psoriasis.

26. The method according to claim 25, wherein the radionuclide is $^{60}$Cu, $^{61}$Cu, $^{62}$Cu, $^{64}$Cu, $^{67}$Cu, or $^{195m}$Pt.

27. The method according to claim 25, wherein the compound is conjugated to a molecular recognition unit, wherein the molecular recognition unit is selected from the group consisting of an antibody, protein, peptide, carbohydrate, nucleic acid, oligonucleotide, oligosaccharide, liposome, siRNA, RNA, DNA, ssDNA, nucleotide, dendrimer, polysaccharide, amino acid, enzyme, oligopeptide, and steroid.

28. The method according to claim 25, wherein the compound is one of:

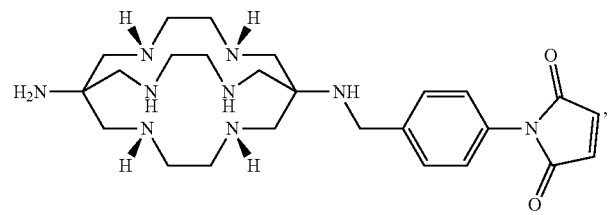

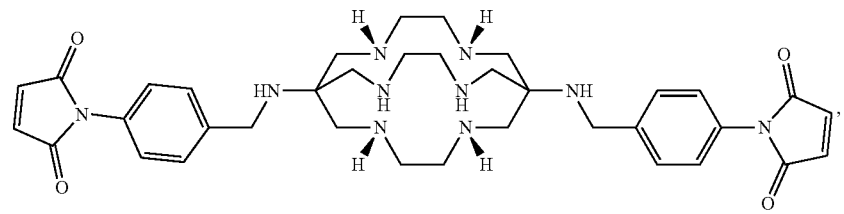

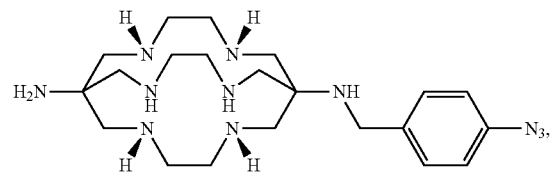

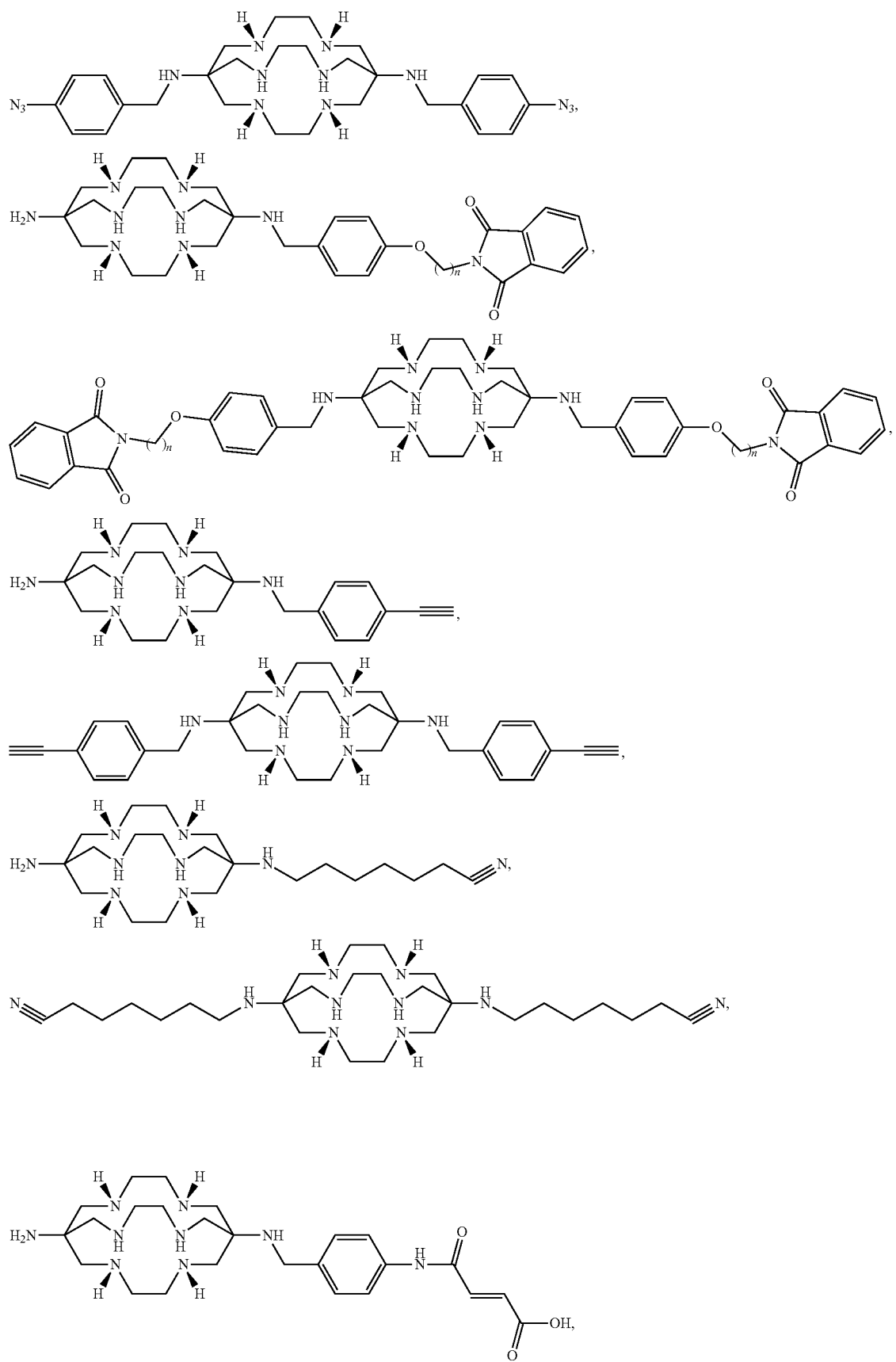

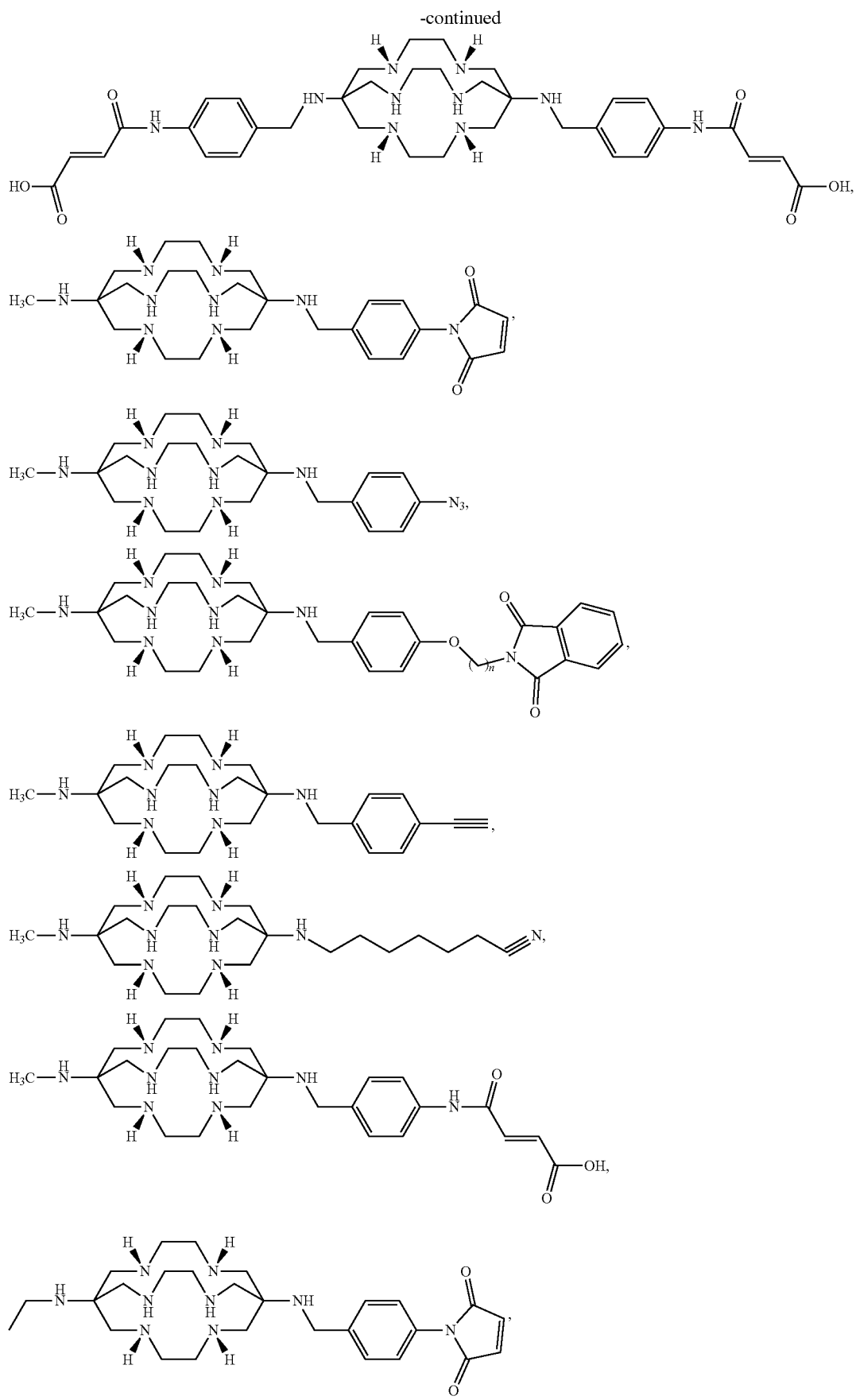

-continued
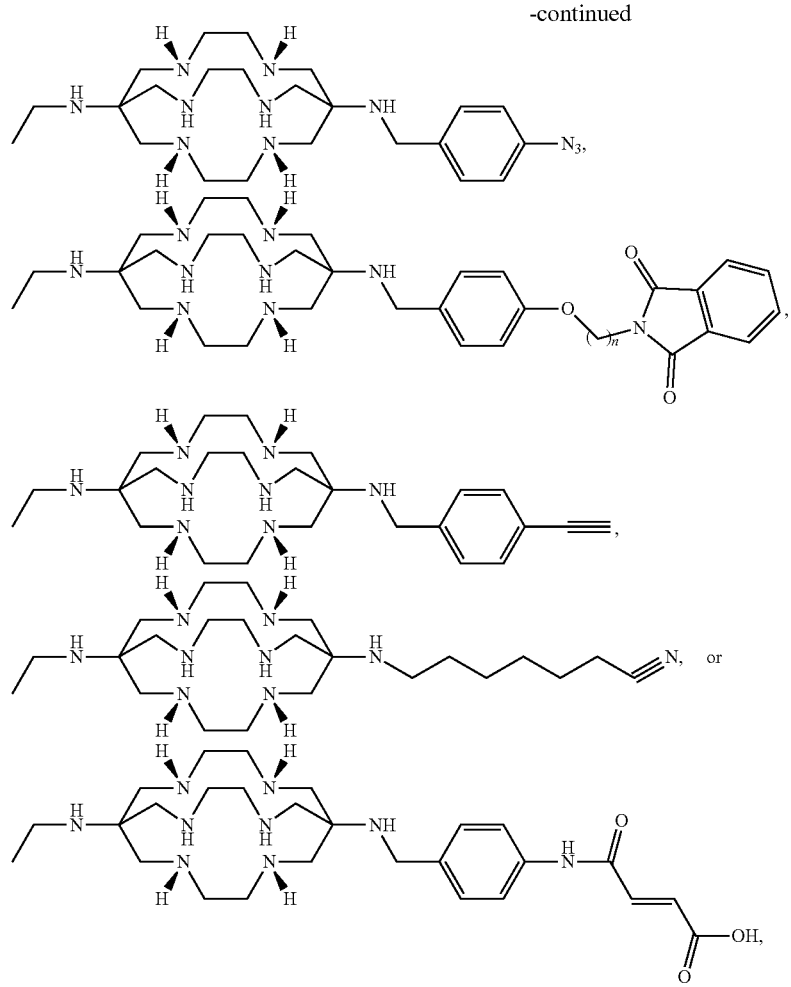
wherein n is an integer of from 1 to 5.
* * * * *